US010745354B2

(12) United States Patent
Stoltz et al.

(10) Patent No.: US 10,745,354 B2
(45) Date of Patent: Aug. 18, 2020

(54) METHODS FOR ENANTIOSELECTIVE ALLYLIC ALKYLATION OF ESTERS, LACTONES, AND LACTAMS WITH UNACTIVATED ALLYLIC ALCOHOLS

(71) Applicant: California Institute of Technology, Pasadena, CA (US)

(72) Inventors: Brian M. Stoltz, San Marino, CA (US); Aurapat Ngamnithiporn, Pasadena, CA (US); Carina I. Jette, Pasadena, CA (US); Shoshana Bachman, Las Vegas, NV (US); Scott C. Virgil, Pasadena, CA (US); Sebastian Lackner, Hamburg (DE)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 16/511,138

(22) Filed: Jul. 15, 2019

(65) Prior Publication Data

US 2020/0048201 A1 Feb. 13, 2020

Related U.S. Application Data

(62) Division of application No. 16/177,926, filed on Nov. 1, 2018, now Pat. No. 10,358,422.

(60) Provisional application No. 62/580,091, filed on Nov. 1, 2017.

(51) Int. Cl.

| | | |
|---|---|---|
| *C07C 69/75* | (2006.01) | |
| *C07D 211/86* | (2006.01) | |
| *C07D 407/06* | (2006.01) | |
| *C07D 409/06* | (2006.01) | |
| *C07D 309/30* | (2006.01) | |
| *C07D 211/76* | (2006.01) | |
| *B01J 31/24* | (2006.01) | |
| *C07D 309/32* | (2006.01) | |
| *C07B 37/04* | (2006.01) | |

(52) U.S. Cl.
CPC ......... *C07D 211/86* (2013.01); *B01J 31/2409* (2013.01); *C07D 211/76* (2013.01); *C07D 309/30* (2013.01); *C07D 309/32* (2013.01); *C07D 407/06* (2013.01); *C07D 409/06* (2013.01); *B01J 2231/4272* (2013.01); *B01J 2531/004* (2013.01); *B01J 2531/847* (2013.01); *C07B 37/04* (2013.01); *C07B 2200/07* (2013.01)

(58) Field of Classification Search
CPC ............................ C07C 69/75; C07C 69/757
USPC ................................................. 560/126, 128
See application file for complete search history.

(56) References Cited

U.S. PATENT DOCUMENTS

| | | |
|---|---|---|
| 2,886,487 A | 5/1959 | Kupferberg |
| 4,639,462 A | 1/1987 | Kramer et al. |
| 5,591,769 A | 1/1997 | Himmelsbach et al. |
| 7,235,698 B2 | 6/2007 | Behenna et al. |
| 8,822,679 B2 | 9/2014 | Stoltz et al. |
| 9,518,034 B2 | 12/2016 | Stoltz et al. |
| 10,035,769 B2 | 7/2018 | Stoltz et al. |
| 10,040,784 B2 | 8/2018 | Stoltz et al. |
| 10,106,479 B2 | 10/2018 | Stoltz et al. |
| 10,343,996 B2 | 7/2019 | Stoltz et al. |
| 10,358,422 B2 | 7/2019 | Stoltz et al. |
| 10,421,696 B2 | 9/2019 | Stoltz et al. |
| 2006/0084820 A1 | 4/2006 | Behenna et al. |
| 2010/0298293 A1 | 11/2010 | Allerheiligen et al. |
| 2013/0267699 A1 | 10/2013 | Stoltz et al. |
| 2015/0105552 A1 | 4/2015 | Stoltz et al. |
| 2016/0096810 A1 | 4/2016 | Stoltz et al. |
| 2016/0176773 A1 | 6/2016 | Stoltz et al. |
| 2016/0280623 A1 | 9/2016 | Stoltz et al. |
| 2020/0048201 A1 | 2/2020 | Stoltz et al. |

FOREIGN PATENT DOCUMENTS

| | | |
|---|---|---|
| DE | 668489 C | 12/1938 |
| WO | WO-9525088 A1 | 9/1995 |
| WO | WO-2003/062265 | 7/2003 |
| WO | WO-2005/012320 A2 | 2/2005 |
| WO | WO-2009/013390 A1 | 1/2009 |
| WO | WO-2009/153178 A2 | 12/2009 |
| WO | WO-2011/153509 A1 | 12/2011 |
| WO | WO-2012/178129 A2 | 12/2012 |

OTHER PUBLICATIONS

Zhang, Q. et al.: Asymmetric induction in Mn(III)-based oxidative free-radical cyclizations of phenylmethyl acetoacetates and 2,5-dimethylpyrrolidine acetoacetamides. J. Org. Chem., vol. 58, pp. 7640-7651, 1993.*
Amat, et al., "Enantioselective Synthesis of 3,3-Disubstituted Piperidine Derivatives by Enolate Dialkylation of Phenylglycinol-derived oxazolopiperidone Lactams," J Org Chem, 72(12): 4431-4439 (2007).
Bach, et al., "Regioselective Reducing Ring Opening of 2-(2-Hydroxyphenyl)-3-[(trimethylsilyl)oxy]oxetanes at the More Substituted C-2-Position," Liebigs Annalen, 1997(7): 1529-1536 (1997).
Badillo, et al., "Enantioselective synthesis of substituted oxindoles and spirooxindoles with applications in drug discovery," Curr Opin Drug Discov Devel, 13(6): 758-776 (2010).
Baussanne, et al., "Diastereoselective Bis-Alkylation of Chiral Non-Racemic α,β-Unsaturated γ-Lactams," Tetrahedron Lett, 35(23): 3931-3934 (1994).
Behenna, et al., "Enantioselective construction of quaternary N-heterocycles by palladium-catalysed decarboxylative allylic alkylation of lactams," Nat Chem, 4(2): 130-133 (2012).
Behenna, et al., "Enantioselective Decarboxylative Alkylation Reactions: Catalyst Development, Substrate Scope, and Mechanistic Studies," Chem Eur J, 17(50): 14199-14223 (2011).

(Continued)

*Primary Examiner* — Charanjit Aulakh
(74) *Attorney, Agent, or Firm* — Foley Hoag LLP; Janine S. Ladislaw; Jyoti R. Tibrewala

(57) ABSTRACT

The present disclosure provides methods for enantioselective synthesis of cyclic and acyclic α-quaternary carboxylic acid derivatives via nickel-catalyzed allylic alkylation.

8 Claims, No Drawings

(56) References Cited

OTHER PUBLICATIONS

Behenna, et al., "The Enantioselective Tsuji Allylation," J Am Chem Soc, 126(46): 15044-15045 (2004).
Bell, et al., "Organocatalytic asymmetric deconjugative Michael additions," J Org Chem, 71(14): 5407-5410 (2006).
Bennett, et al., "A Unified Approach to the Daucane and Sphenolobane Bicyclo[5.3.0]decane Core: Enantioselective Total Synthesis of Daucene, Daucenal, Epoxydaucenal B, and 14-para-Anisoyloxydauc-4,8-diene", Chem Eur J, 19(52): 17745-17750 (2013).
Bennett, et al., "Expanding Insight into Asymmetric Palladium-Catalyzed Allylic Alkylation of N-Heterocyclic Molecules and Cyclic Ketones," Chem Eur J, 19(14): 4414-4418 (2013).
Bennett, et al., "Synthesis of enantioenriched γ-quaternary cycloheptenones using a combined allylic alkylation/Stork-Danheiser approach: preparation of mono-, bi-, and tricyclic systems", Org Biomol Chem, 10(1): 56-59 (2012).
Bobranski, et al., "Hydration of Phenyldiallylacetamide," Bulletin de l'Academie Polonaise de Sciences, Serie des Sciences, Chimiques, Geologiques et Geographiques, 7: 399-401 (1959).
Bulman, et al., "Short and Versatile Route to a Key Intermediate for Lactacystin Synthesis," Org Lett, 5(3): 353-355 (2003).
CAS Registry No. 1823805-71-5, (Entered STN: Dec. 6, 2015).
Chattopadhyay et al., "Mechanistic Origin of the Stereodivergence in Decarboxylative Allylation," Org Lett, 12(13): 3042-3045 (2010).
Coates, et al., "Efficient synthesis of 3-substituted lactams using Meerwein Eschenmoser Claisen [3,3] sigmatropic rearrangements," Tetrahedron Lett, 32(33): 4199-4202 (1991).
Day, et al., "The Catalytic Enantioselective Total Synthesis of (+)-Liphagal," Angew Chem Int Ed, 50(30): 6814-6818 (2011).
Desmaele, et al., "Stereocontrolled Elaboration of Quaternary Carbon Centers through the Asymmetric Michael-Type Alkylation of Chiral Imines/Secondary Enamines: Enantioselective Synthesis of (+)-Vincamine," J Org Chem, 62(12): 3890-3901 (1997).
Enders, et al., "Asymmetric Electrophilic Substitutions at the α-Position of γ- and δ-Lactams," Eur J Org Chem, 2001(23): 4463-4477 (2001).
Enquist, et al., "The total synthesis of (−)-cyanthiwigin F by means of double catalytic enantioselective alkylation," Nature, 453(7199): 1228-1231 (2008).
Enquist, et al., "Total Syntheses of Cyanthiwigins B, F, and G," Chem Eur J, 17(36): 9957-9969 (2011).
Extended European Search Report for EP Application No. 18203943.8 dated Mar. 21, 2019.
Extended European Search Report for EP Application No. EP 17764072 dated Jul. 29, 2019.
Extended European Search Report received for EP Patent Application No. 16773845.9, dated Oct. 9, 2018.
Ezquerra, et al., "Stereoselective Double Alkylation of Ethyl N-Boc-pyroglutamate," J Org Chem, 59(15): 4327-4331 (1994).
Fuji, et al., "Addition-elimination strategy for asymmetric induction: a chiral sulfoxide as a leaving group," Tetrahedron Lett, 31(17): 2419-2422 (1990). (CAS abstract).
Gartshore, et al., "Enantioselective Palladium-Catalyzed Decarboxylative Allylation of Carbazolones and Indolones: Formal Synthesis of (+)-Kopsihainanine A," Angew Chem Int Ed, 52(15): 4113-4116 (2013).
Groaning, et al., "Chiral Non-Racemic Bicyclic Lactams. Auxiliary-Based Asymmetric Reactions," Tetrahedron, 56(51): 9843-9873 (2000).
Ha et al., "Enantioselective Phase-Transfer Catalytic [α]-Benzylation and [α]-Allylation of [α]-tert—Butoxycarbonyl-lactones," Advanced Synthesis & Catalysis, 355(4): 637-642 (2013).
Hayashi et al., "Ni-Catalyzed Enantioselective C-Acylation of a-Substituted Lactams," J Am Chem Soc, 138(29):8997-9000 (2016).
Heathcock et al., "Daphniphyllum alkaloids. 15. Total syntheses of (.+−.)-methyl homodaphniphyllate and (.+−.)-daphnilactone A," J Org Chem, 57(9):2585-2594 (1992).

Helmchen, et al., "Phosphinooxazolines—A New Class of Versatile, Modular P,N-Ligands for Asymmetric Catalysis," Acc Chem Res, 33(6): 336-345 (2000).
Hong, et al., "Biosynthesis and Chemical Synthesis of Presilphiperfolanol Natural Products," Angew Chem Int Ed, 53(21): 5248-5260 (2014).
Hong, et al., "Enantioselective Total Synthesis of the Reported Structures of (−)-9-epi-Presilphiperfolan-1-ol and (−)-Presilphiperfolan-1-ol: Structural Confirmation and Reassignment and Biosynthetic Insights," Angew Chem Int Ed, 51(38): 9674-9678 (2012).
Hong, et al., "Palladium-catalyzed asymmetric alkylation in the synthesis of cyclopentanoid and cycloheptanoid core structures bearing all-carbon quaternary stereocenters," Tetrahedron, 67(52): 10234-10248 (2011).
Hong, et al., "The Construction of All-Carbon Quaternary Stereocenters by Use of Pd-Catalyzed Asymmetric Allylic Alkylation Reactions in Total Synthesis," Eur J Org Chem, 2013(14): 2745-2759 (2013).
Imao, et al., "Easy Access to Esters with a Benzylic Quaternary Carbon Center from Diallyl Malonates by Palladium-Catalyzed Decarboxylative Allylation," J Org Chem, 72(5): 1652-1658 (2007).
International Search Report and Written Opinion for International Application No. PCT/US2012/043904 dated Feb. 1, 2013.
International Search Report and Written Opinion for International Application No. PCT/US2016/024238 dated Jul. 11, 2016.
International Search Report and Written Opinion for International Application No. PCT/US2017/021528 dated May 25, 2017.
Jakubec, et al., "Enantio- and diastereoselective Michael additions of C-succinimidyl esters to nitro olefins using cinchonine-derived bifunctional organocatalysts," Tetrahedron: Asymmetry, 22(11): 1147-1155 (2011).
Jing, et al., " Total Synthesis of (+)-Kopsihainanine A," Chem Eur J, 18(22): 6729-6732 (2012).
Johnson, et al., "Asymmetric carbon-carbon bond formations in conjugate additions of lithiated N-boc allylic and benzylic amines to nitroalkenes: Enantioselective synthesis of substituted piperidines, pyrrolidines, and pyrimidinones," J Am Chem Soc, 124(39): 11689-11698 (2002).
Juaristi, et al., "Enantioselective synthesis of β-amino acids. Part 9: Preparation of enantiopure α, α-disubstituted β-amino acids from 1-benzoyl-2(S)-tert-butyl-3-methylperhydropyrimidin-4-one[1,2]," Tetrahedron: Asymmetry, 9(21): 3881-3888 (1998).
Keith, et al., "The Reaction Mechanism of the Enantioselective Tsuji Allylation: Inner-Sphere and Outer-Sphere Pathways, Internal Rearrangements, and Asymmetric C—C Bond Formation," J Am Chem Soc, 134(46): 19050-19060 (2012).
Kim, et al., "An Asymmetric Synthesis of (+)-Isonitramine by 'Triple Allylic Strain-Controlled' Intramolecular SN2' Alkylation," Tetrahedron Lett, 37(9): 1433-1434 (1996).
Kita et al., "Asymmetric Allylic Alkylation of b-ketoesters with allylic alcohols by a nickel/diphosphine catalyst," Angewandte Chemie International Edition, 55:1098-1101 (2016).
Korch et al., "Enantioselective synthesis of a-secondary and a-tertiary piperazin-2-ones and piperazines by catalytic asymmetric allylic alkylation," Angew Chem Int Edit, 54(1): 179-183 (2015).
Lee et al., "Asymmetric synthesis and evaluation of [α]-quaternary chiral lactam derivatives as novel anticancer agents," Archives of Pharm Res, 37(10):1264-1270 (2013).
Li et al., "Synthesis of Mannich Bases of Meldrum's Acid and Its 5-Substituted Derivatives," Synthetic Commun, 30(13):2317-2323 (2000).
Li, et al., "Enantioselective Palladium-Catalyzed Decarboxylative Allylation of Carbazolones: Total Synthesis of (−)-Aspidospermidine and (+)-Kopsihainanine A," Angew Chem Int Ed, 52(15): 4117-4121 (2013).
Liu, et al., "Construction of Vicinal Tertiary and All-Carbon Quaternary Stereocenters via Ir-Catalyzed Regio-, Diastereo-, and Enantioselective Allylic Alkylation and Applications in Sequential Pd Catalysis," J Am Chem Soc, 135(29): 10626-10629 (2013).
Lu et al., "Metal-Catalyzed Enantioselective Allylation in Asymmetric Synthesis," Angew Chem Int Ed, 47(2): 258-297 (2008).
Ma, et al., "Palladium-catalyzed decarboxylative allylic alkylation of diastereomeric β-ketoesters," Tetrahedron, 70(27): 4208-4212 (2014).

(56) References Cited

OTHER PUBLICATIONS

Marziale et al., "An Efficient Protocol for the Palladium-Catalyzed Asymmetric Decarboxylative Allylic Alkylation Using Low Palladium Concentrations and a Palladium(II) Precatalyst," Adv Synth Catal, 357: 2238-2245 (2015).
McDougal, et al., "High-Throughput Screening of the Asymmetric Decarboxylative Alkylation Reaction of Enolate-Stabilized Enol Carbonates," Snylett, 2010(11): 1712-1716 (2010).
McDougal, et al., "Rapid synthesis of an electron-deficient t-BuPHOX ligand: cross-coupling of aryl bromides with secondary phosphine oxides," Tetrahedron Lett, 51(42): 5550-5554 (2010).
McFadden, et al., "The Catalytic Enantioselective, Protecting Group-Free Total Synthesis of (+)-Dichroanone," J Am Chem Soc, 128 (24): 7738-7739 (2006).
Melhado et al., "Gold(I)-Catalyzed Diastereo- and Enantioselective 1,3-Dipolar Cycloaddition and Mannich Reactions of Azlactones," J Am Chem Soc, 133(10):3517-3527 (2011).
Mertes, et al., "Glutarimides," J Am Pharm Assoc, 67: 882-885 (1958). (CAS Abstract).
Meyers, et al., "Stereoselective Alkylations in Rigid Systems. Effect of Remote Substituents on pi-Facial Additions to Lactam Enolates. Stereoelectronic and Steric Effects," J Am Chem Soc, 120(30): 7429-7438 (1998).
Mohr, et al., "Deracemization of Quaternary Stereocenters by Pd-Catalyzed Enantioconvergent Decarboxylative Allylation of Racemic β-Ketoesters," Angew Chem Int Ed, 44 (42): 6924-6927 (2005).
Mohr, et al., "Enantioselective Tsuji Allylations," Chem Asian J, 2(12): 1476-1491 (2007).
Moss, et al., "Catalytic Enantio- and Diastereoselective Alkylations with Cyclic Sulfamidates," Angew Chem Int Ed, 49(3): 568-571 (2010).
Ngamnithiporn et al., "Nickel-catalyzed enantioselective allylic alkylation of lactones and lactams with unactivated allylic alcohols," Chemical Science, 9:2547-2551 (2018).
Notice of Allowance and Fees Due for U.S. Appl. No. 15/081,157 dated Mar. 30, 2018.
Numajiri, et al., "Enantioselective synthesis of a-quaternary mannich adducts by palladium-catalyzed allylic alkylation: Total synthesis of (+)-sibirinine," J Am Chem Soc, 137(3): 1040-1043 (2015).
Numajiri, et al., "Enantioselective Synthesis of Dialkylated N-Heterocycles by Palladium-Catalyzed Allylic Alkylation," Organic Letters 1082-1085 (2015).
Ojima, et al., "Asymmetric Synthesis with Chiral β-Lactams. Highly Stereoselective Alkylation and Aldol Reaction of a Chiral 3-Amino-4-Styryl-β-Lactam," Tetrahedron Lett, 31(7): 977-980 (1990).
Padwa, et al., "A Novel Cycloaddition Reaction of α-Diazo-γ-amido Ketones Catalyzed by Rhodium (II) Acetate. Scope and Mechanistic Details of the Process," J Org Chem, 61(7): 2283-2292 (1996). (CAS Abstract).
Park et al., "Highly Enantioselective Total Synthesis of (+)-Isonitramine," Organic Letters, 14(3):852-854 (2012).
Park, et al., "Highly Enantioselective Phase-Transfer Catalytic α-Alkylation of α-tert-Butoxycarbonyllactams: Construction of β-Quaternary Chiral Pyrrolidine and Piperidine Systems," Adv Synth Catal, 353(18): 3313-3318 (2011).
Quirante et al., "Synthesis of Diazatricyclic Core of Madangamines from cis Perhydroisoquinolines," J Org Chem, 73(2): 768-771 (2008).
Reeves, et al., "Development of (Trimethylsilyl)ethyl Ester Protected Enolates and Applications in Palladium-Catalyzed Enantioselective Allylic Alkylation: Intermolecular Cross-Coupling of Functionalized Electrophiles," Org Lett, 16(9): 2314-2317 (2014).
Reeves, et al., "Enantioselective Construction of α-Quaternary Cyclobutanones by Catalytic Asymmetric Allylic Alkylation," Angew Chem Int Ed, 52(26): 6718-6721 (2013).
Rodriguez, et al., ""Carba" Peptide Bond Surrogates/Different Approaches to Gly-(CH2-CH2)-D,L-XAA Pseudodipeptide Units," Int J Peptide Protein Res, 39(3): 273-277 (1992).

Ruggeri et al., "Synthesis of polycyclic lactam and lactone ethers by intramolecular Reformatsky reactions. A model for construction of the daphnilactone A ring system," J Org Chem, 52(26):5745-5746 (1987).
Sato et al., "N-Heterocyclic carbenes as ligands in palladium-catalyzed Tsuji-Trost allylic substitution," Journal of Organometallic Chemistry, 690(24-25): 5753-5758 (2005).
Schwarz, et al., "Tandem α-Cyano Enamine/Enolate Alkylations on Bicyclic Lactams: Asymmetric Carbocycle and Heterocycle Synthesis," J Org Chem, 63(5): 1619-1629 (1998).
Seidel, et al., "Aldol and Claisen condensations with 1-(3,4-dichlorophenyl)-2-pyrrolidinone," J of Heterocyclic Chem, 3(3):311-314 (1966).
Seto, et al., "Catalytic Enantioselective Alkylation of Substituted Dioxanone Enol Ethers: Ready Access to C(α)-Tetrasubstituted Hydroxyketones, Acids, and Esters," Angew Chem Int Ed, 120(36): 6979-6982 (2008).
Sherden, "Mechanistic investigations into the palladium-catalyzed decarboxylative allylic alkylation of ketone enolates using the PHOX ligand architecture," Chapter 1, Dissertation, California Institute of Technology (2011). Retrieved from the Internet: <http://thesis.library.caltech.edu/6476/2/03-Chpt_1_Intro.pdf.>.
Shibuya, et al., "Enantioselective Synthesis of 5-6-7 Carbocyclic Core of the Gagunin Diterpenoids," Org Lett, 15(13): 3480-3483 (2013).
Sternativo, et al., "Synthesis of γ-lactams via a domino Michael addition/cyclization reaction of vinyl selenone with substituted amides." Tetrahedron Letters, 54(49):6755-6757 (2013).
Streuff, et al., "A palladium-catalysed enolate alkylation cascade for the formation of adjacent quaternary and tertiary sterocentres," Nat Chem, 2(3): 192-196 (2010).
Takahashi, et al., "Atropisomeric lactam chemistry: catalytic enantioselective synthesis, application to asymmetric enolate chemistry and synthesis of key intermediates for NET inhibitors," Tetrahedron, 66(1): 288-296 (2010).
Tani, et al., "A Facile and Modular Synthesis of Phosphinooxazoline Ligands," Org Lett, 9(13): 2529-2531 (2007).
Tari, et al., "Recoverable Cinchona ammonium salts as organocatalysts in the enantioselective Michael addition of β-Keto esters," Tetrahedron: Asymmetry, 21(23): 2872-2878 (2010).
Tasker et al., "Recent advances in homogeneous nickel catalysis," Nature, 509(7500): 299-309 (2014).
Trost, et al., "Asymmetric Allylic Alkylation, an Enabling Methodology," J Org Chem, 69(18): 5813-5837 (2004).
Trost, et al., "Asymmetric Synthesis of Oxindole and Indole Spirocyclic Alkaloid Natural Products," Synthesis, 2009(18): 3003-3025 (2009).
Trost, et al., "Enantioselective Synthesis of α-Tertiary Hydroxyaldehydes by Palladium-Catalyzed Asymmetric Allylic Alkylation of Enolates," J Am Chem Soc, 129(2): 282-283 (2007).
Tsuji et al., "Catalytic asymmetric synthesis of pentacyclic core of (−)-nakadomarin A via oxazolidine as an iminium cation equivalent," Org Biomol Chem, 12(40):7919-7922 (2014).
Varea, et al., "Asymmetric Synthesis. XXXV 1. Synthesis of 2-Methyl 5-Substituted Piperidines from Chiral Non-racemic Lactams," Tetrahedron Lett, 36(7): 1035-1038 (1995).
Vijin, et al., "Highly Enantioselective Synthesis of a 2,3-Dihydroindole Mediated by N-Methylephedrine," Angew Chem Int Ed, 23(2): 165-166 (1984).
Weaver, et al., "Transition Metal-Catalyzed Decarboxylative Allylation and Benzylation Reactions," Chem Rev, 111(3): 1846-1913 (2011).
White, et al., "The Catalytic Asymmetric Total Synthesis of Elatol," J Am Chem Soc, 130(3): 810-811 (2008).
Williams, et al., "Asymmetric synthesis of monosubstituted and α,α-disubstituted α-amino acids via diastereoselective glycine enolate alkylations," J Am Chem Soc, 113(24): 9276-9286 (1991).
Yamamoto et al., "Palladium-catalyzed asymmetric cyclization of methyl (E)-oxo-phenoxy-7-nonenoate and its analogs," Tetrahedron Letters, 23(30): 3089-3092 (1982).
Yang et al., "A new synthetic method for preparing Mannich bases of Meldrum's acid," Chinese J Org Chem, 22(7):525-527 (2002).

(56) References Cited

OTHER PUBLICATIONS

Yendapally, et al., "Design, synthesis, and evaluation of novel ethambutol analogues," Bioorg Med Chem Lett, 18(5):1607-1611 (2008).
Zawisza, et al., "An unexpected palladium-catalyzed cyclization of bis-hydroxy allylic alcohols to dioxabicyclo[2.2.2]octanes," Tetrahedron Lett, 47(19): 3271-3274 (2006).
Zawisza, et al., "Palladium-catalyzed formation of cyclic ethers—regio-, stereo- and enantioselectivity of the reaction," Eur J Org Chem, 2007(14): 2296-2309 (2007).
Zhang et al., "Direct N-Acylation of Lactams, Oxazolidinones, and Imidazolidinones with Aldehydes by Shvo's Catalyst," Org Lett, 14(17): 4646-4649 (2012).
Zhou, et al., "Catalytic Asymmetric Synthesis of Oxindoles Bearing a Tetrasubstituted Stereocenter at the C-3 Position," Adv Synth Catal, 352(9): 1381-1407 (2010).
Appeal Brief for U.S. Appl. No. 16/166,893 dated Feb. 11, 2020.
Dashkina et al., "Palladium-catalyzed allylation of salts of unsubstituted and substituted 5-nitro-1,3-dioxanes," Zhurnal Organicheskoi Khimii 30(11):1656-1659 (1994).
Elz et al., "Synthesis, Biological in vitro evaluation and stereoselectivity of ondansetron analogues: novel 5-HT2A receptor antagonists," Bioorg Med Chem Letts 5(7):667-672 (1995).
Extended European Search Report for EP application No. EP12802759.6 dated Mar. 14, 2016.
Pre-Appeal Brief Conference Request for Review for U.S. Appl. No. 16/166,893 dated Jul. 11, 2019.
Schelwies et al., "Gold-Catalyzed Intermolecular Addition of Carbonyl Compounds to 1,6-Enynes: Reactivity, Scope, and Mechanistic Aspects," Chem Eur J 15(41):10888-10900 (2009).
Sun et al., "Enantioselective synthesis of gem-disubstituted N-Boc diazaheterocycles via decarboxylative asymmetric allylic alkylation," Chem Sci 10:788-792 (2019).
Supplemental European Search Report for EP application No. EP12802759 dated Oct. 28, 2014.

\* cited by examiner

METHODS FOR ENANTIOSELECTIVE ALLYLIC ALKYLATION OF ESTERS, LACTONES, AND LACTAMS WITH UNACTIVATED ALLYLIC ALCOHOLS

RELATED APPLICATIONS

This Application is a divisional of U.S. patent application Ser. No. 16/177,926 filed on Nov. 1, 2018, which claims the benefit of U.S. Provisional Application 62/580,091, filed Nov. 1, 2017, the contents of both of which are hereby incorporated herein by reference.

GOVERNMENT SUPPORT

This invention was made with government support under Grant Nos. GM080269 awarded by the National Institutes of Health. The Government has certain rights in the invention.

BACKGROUND

Synthetic methods for the generation of enantioenriched quaternary stereocenters are highly desirable given their prevalence as motifs in a wide variety of biologically active molecules of both natural and unnatural origin, and the pharmaceutical industries increasing recognition for the motifs applicability in drug design. Despite their importance, the number of highly enantioselective transformations that construct quaternary stereocenters under mild reaction conditions is limited, with respect to both cyclic and acyclic systems.

Since 1965, transition metal-catalyzed allylic alkylation has emerged as one of the most powerful methods for the construction of stereocenters. In particular, with the use of prochiral nucleophiles that proceed through tetrasubstituted enolates, the transition metal-catalyzed enantioselective allylic alkylation has proven to be a formidable strategy for accessing chiral quaternary stereocenters in catalytic enantioselective fashion. Although this transformation has been studied for more than 50 years, the use of α-substituted lactones or lactams as prochiral nucleophiles remains significantly under-developed.

It is particularly difficult to construct quaternary stereocenters in scaffolds containing an additional functional handle for further synthetic manipulation, such as α-acyl lactones and lactams. Lactone products could also provide access to acyclic quaternary stereocenters via ring-opening reactions and reduction of the lactam products would enable direct access to functionalized piperidine rings, the most prevalent nitrogenous heterocycle in drug molecules.

Recently, a palladium-catalyzed decarboxylative enantioselective allylic alkylation of enol carbonates derived from γ-butyrolactones was disclosed. Various enol carbonates were used to obtain diverse α-acyl quaternary butyrolactones in moderate to high levels of enantioselectivity. Nonetheless, the limited electrophile scope and challenging nucleophile synthesis limits the practicality of this transformation. In particular, the alkylation appears limited to γ-butyrolactone substrates and an allyl group, and the substrates require low-yielding, multi-step synthesis.

Therefore, the catalytic enantioselective construction of all-carbon quaternary centers represents a considerable challenge in synthetic organic chemistry due to the difficulties associated with effecting an enantioselective C—C bond formation in a sterically hindered environment.

Accordingly, there is a need to develop new reaction protocols that provide access to cyclic and acyclic α-quaternary carboxylic acid derivatives (i.e., acids, esters, amides).

SUMMARY

Provided herein are methods for the enantioselective synthesis of cyclic and acyclic α-quaternary carboxylic acid derivatives via nickel-catalyzed allylic alkylation. Accordingly, in one aspect provided herein are methods for preparing a compound of Formula (IX):

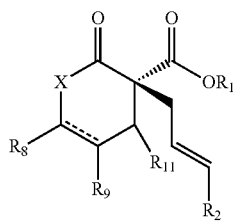

comprising:
treating a compound of Formula (I)

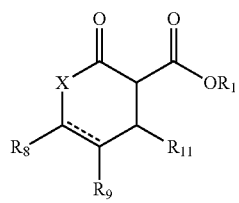

with a compound of Formula (IIa) or (IIb)

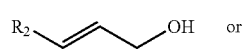

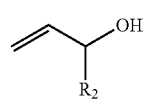

in an organic solvent
in the presence of a nickel catalyst;
wherein:
X is O or N-PG;
PG is a protecting group;
$R_1$ is $C_{1-5}$ alkyl;
$R_2$ is H, $C_{1-5}$ alkyl, $C_{1-5}$ alkenyl, aralkyl, aralkenyl, aryl, or hetaryl;
⇌ is a single bond or a double bond, as valence permits; and
one of the following:
(i) $R_8$ and $R_9$ are each H;
(ii) $R_8$ is H, and $R_9$ and $R_{11}$, taken together with the carbon atoms to which they are attached, form a heterocyclic, carbocyclic, aryl, or hetaryl ring; or
(iii) $R_{11}$ is H, $R_8$ and $R_9$, taken together with the carbon atoms to which they are attached, form a heterocyclic, carbocyclic, aryl, or hetaryl ring.

In certain embodiments, the nickel catalyst is a Ni(0) catalyst, for example, a complex formed by contacting a Ni(0) source with a ligand L.

In certain embodiments, L is selected from L1, L2, L3, L4, L5, L6, L7, L8, L9, L10, L11, L12, L13, L14, L15, L16, L17, L8, L19, L20, L21, L22, L23, L24, L25, L26, L27, L28, L29, L30, L31, L32, L33. L34, L35, L36, L37, L38, L39, and L40. In preferred embodiments, L is selected from (R)-BINAP, (R)—Hs-BINAP, (R)-Segphos, and (R)—P-phos. Even more preferably, L is (R)—P-phos.

In some embodiments, X is O and the solvent is diethyl ether. In preferred embodiments, L is (R)—P-phos.

In other embodiments, X is N-PG.

In certain embodiments, X is N-PG and PG is selected from benzoyl, Boc, methyl, and phenyl, preferably, PG is benzoyl.

In some embodiments, the Ni(0) source is Ni(COD)$_2$.

In certain other embodiments, the organic solvent is toluene, diethyl ether, methyl t-butyl ether, tetrahydrofuran, or dioxane, or a mixture thereof.

In some embodiments, $R_8$ and $R_9$, taken together with the carbon atoms to which they are attached, form a 5- or 6-membered heterocyclic, carbocyclic, aryl, or hetaryl ring.

In some embodiments, $R_8$ and $R_9$, taken together with the carbon atoms to which they are attached, form a 5- or 6-membered heterocyclic or carbocyclic ring; and ⇜ is a single bond.

In some embodiments, $R_8$ and $R_9$, taken together with the carbon atoms to which they are attached, form a 5- or 6-membered aryl or hetaryl ring; and ⇜ is a double bond.

Also provided herein are methods of preparing a compound of Formula (XI):

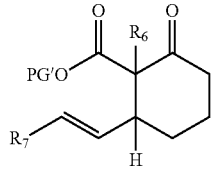

(XI)

comprising treating a compound of Formula (XII)

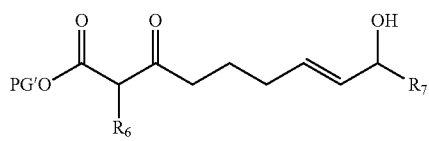

(XII)

in an organic solvent
in the presence of a nickel catalyst,
wherein
PG' is an oxygen protecting group;
$R_6$ is $C_{1-5}$ alkyl;
$R_7$ is $C_{1-5}$ alkyl.

In certain embodiments, the nickel catalyst is a Ni(0) catalyst, for example, a complex formed by contacting a Ni(0) source with a ligand L.

In some embodiments, the Ni(0) source is Ni(COD)$_2$.

In certain other embodiments, the organic solvent is toluene, diethyl ether, methyl t-butyl ether, tetrahydrofuran, or dioxane, or a mixture thereof.

In some embodiments, the oxygen protecting group is PMB.

In some embodiments, the Ni(0) source is Ni(COD)$_2$; L is (S)-C3-TunePhos; and the organic solvent is diethyl ether. In certain preferred embodiments, $R_6$ is methyl; $R_7$ is methyl; and PG' is PMB.

Also provided herein are methods comprising:

preparing a compound of Formula (IX) as described herein, or preparing a compound of Formula (XI) as described herein; and synthesizing a pharmaceutical agent from the compound of Formula (IX), or synthesizing a pharmaceutical agent from the compound of Formula (XI).

For example, also provided herein are methods of preparing a compound of Formula (VI):

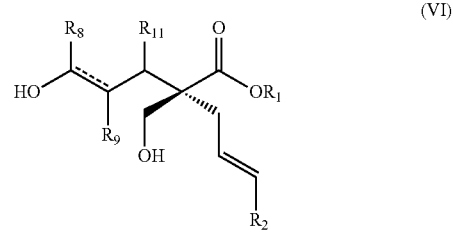

(VI)

comprising treating a compound of Formula (III)

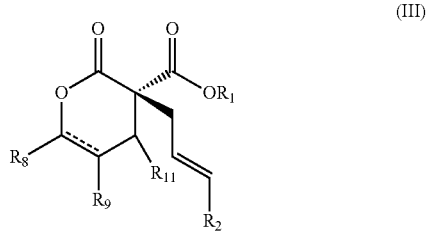

(III)

with a reducing agent;
wherein
$R_1$ is $C_{1-5}$ alkyl;
$R_2$ is H, $C_{1-5}$ alkyl, $C_{1-5}$ alkenyl, aralkyl, aralkenyl, aryl, or hetaryl;
⇜ is a single bond or a double bond, as valence permits;
and one of the following:
(i) $R_8$, $R_9$, and $R_{11}$ are each H;
(ii) $R_8$ is H, and $R_9$ and $R_{11}$, taken together with the carbon atoms to which they are attached, form a heterocyclic, carbocyclic, aryl, or hetaryl ring; or
(iii) $R_1$, is H, and $R_8$ and $R_9$, taken together with the carbon atoms to which they are attached, form a heterocyclic, carbocyclic, aryl, or hetaryl ring.

In some embodiments, $R_1$ is ethyl and $R_2$ is H. In some embodiments, $R_8$, $R_9$, and $R_{11}$ are each H.

As another example, also provided herein are methods of preparing a compound of Formula (VII):

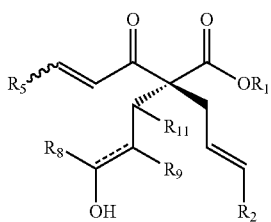

(VII)

comprising treating a compound of Formula (III)

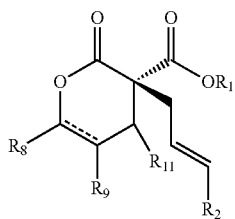

(III)

with a compound of Formula (X)

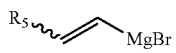

(X)

wherein $R_1$ is $C_{1-5}$ alkyl;

$R_2$ is H, $C_{1-5}$ alkyl, $C_{1-5}$ alkenyl, aralkyl, aralkenyl, aryl, or hetaryl;

$R_8$ is H $C_{1-5}$ alkyl, or $C_{1-5}$ alkenyl;

⇝ is a single bond or a double bond, as valence permits; and one of the following:

(i) $R_8$, $R_9$, and $R_{11}$ are each H;

(ii) $R_8$ is H, and $R_9$ and $R_{11}$, taken together with the carbon atoms to which they are attached, form a heterocyclic, carbocyclic, aryl, or hetaryl ring; or (iii) $R_1$ is H, and $R_8$ and $R_9$, taken together with the carbon atoms to which they are attached, heterocyclic, carbocyclic, aryl, or hetaryl ring.

In some embodiments, $R_1$ is ethyl and $R_2$ is H. In some embodiments, $R_8$, $R_9$, and $R_{11}$ are each H.

As yet another example, also provided herein are methods of preparing a compound of Formula (VIII):

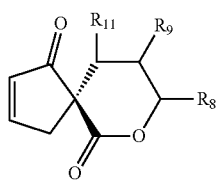

(VIII)

comprising:

synthesizing the compound of Formula (VII) as described herein, and treating the compound of Formula (VII) with a ring-closing metathesis catalyst.

DETAILED DESCRIPTION

Overview

Described herein are the enantioselective allylic alkylation of α-acyl lactones and lactams by using an inexpensive nickel catalyst and easily accessible prochiral nucleophiles. The use of an intermolecular allylic alkylation simplifies the substrate synthesis and provides a more convergent approach to these α-quaternary products. Utilizing a commercially available chiral bisphosphine ligand, α-quaternary lactones and lactams can be constructed in good yield (up to 91% yield) and with high enantiomeric excess (up to 90% ee). A broad range of functional groups are compatible with the reaction conditions. A number of product derivatizations showed the synthetic utility of this methodology for constructing small chiral building blocks with multiple functional handles.

Definitions

The definitions for the terms described below are applicable to the use of the term by itself or in combination with another term.

The term "about," as used herein, is defined as being close to as understood by one of ordinary skill in the art. In one non-limiting embodiment, the term "about" is defined to be within 10%, preferably within 5%, more preferably within 1%, and most preferably within 0.5%. The term "acyl" is art-recognized and refers to a group represented by the general formula hydrocarbyl-C(O)—, preferably alkyl-C(O)—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, ethoxy, propoxy, tert-butoxy, and the like.

The term "alkoxyalkyl" refers to an alkyl group substituted with an alkoxy group, and may be represented by the general formula alkyl-O-alkyl.

The term "alkenyl", as used herein, refers to an aliphatic group containing at least one double bond that is straight chained or branched and has from 1 to about 20 carbon atoms, preferably from 1 to about 10 unless otherwise defined. The term "alkenyl" is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl. iso-propyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls," the latter of which refers to alkyl moieties having substituents replacing a hydrogen on one or more carbons of the hydrocarbon backbone. Such substituents, if not otherwise specified, can include, for example, a halogen, a hydroxyl, a carbonyl (such as a carboxyl, an alkoxycarbonyl, a formyl, or an acyl such as an alkylC(O)), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a silyl ether, a sulfhydryl, an alkylthio, a sulfate, a sulfonate, a sulfamoyl, a sulfonamido, a sulfonyl, a heterocyclyl, an aralkyl, a heteroaralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthiols, carbonyls (including ketones, aldehydes, carboxylates, and esters), —$CF_3$, —CN, and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "$C_x$-$C_y$" when used in conjunction with a chemical moiety, such as, acyl, acyloxy, alkyl, alkenyl, alkynyl, or alkoxy is meant to include groups that contain from x to y carbons in the chain. For example, the term "$C_x$-$C_y$-alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. $C_0$ alkyl indicates a hydrogen where the group is in a terminal position, a bond if internal. The terms "$C_2$-$C_y$-alkenyl" and "$C_2$-$C_y$-alkynyl" refer to substituted or unsubstituted unsaturated aliphatic groups analogous in length and possible substitution to the alkyls described above, but that contain at least one double or triple bond respectively.

The term "alkylthio," as used herein, refers to a thiol group substituted with an alkyl group and may be represented by the general formula alkyl-S—.

The term "alkynyl", as used herein, refers to an aliphatic group containing at least one triple bond and is intended to include both "unsubstituted alkynyls" and "substituted alkynyls," the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide," as used herein, refers to a group

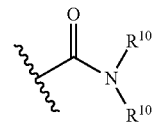

wherein each $R^{10}$ independently represent a hydrogen or hydrocarbyl group, or two $R^{10}$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

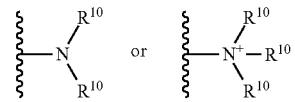

wherein each $R^{10}$ independently represents a hydrogen or a hydrocarbyl group, or two $R^{10}$ are taken together with the N atom to which they are attached complete a heterocycle having from 4 to 8 atoms in the ring structure.

The term "aminoalkyl," as used herein, refers to an alkyl group substituted with an amino group.

The term "aralkyl," as used herein, refers to an alkyl group substituted with an aryl group. An aralkyl group is connected to the rest of the molecule through the alkyl component of the aralkyl group.

The term "aryl" as used herein include substituted or unsubstituted single-ring aromatic groups in which each atom of the ring is carbon. Preferably, the ring is a 5- to 10-membered ring, more preferably a 6- to 10-membered ring or a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like. Exemplary substitution on an aryl group can include, for example, a halogen, a haloalkyl such as trifluoromethyl, a hydroxyl, a carbonyl (such as a carboxyl, an alkoxycarbonyl, a formyl, or an acyl such as an alkylC(O)), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a silyl ether, a sulfhydryl, an alkylthio, a sulfate, a sulfonate, a sulfamoyl, a sulfonamido, a sulfonyl, a heterocyclyl, an aralkyl, or an aromatic or heteroaromatic moiety The terms "carbocycle" and "carbocyclic," as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond. "Carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene, and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two, three, or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The term "carbonate" is art-recognized and refers to a group —OCO$_2$—R$^{10}$, wherein R$^{10}$ represents a hydrocarbyl group.

The term "carboxyl", as used herein, refers to a group represented by the formula —CO$_2$H.

The term "ester," as used herein, refers to a group —C(O)OR$^{10}$ wherein R$^{10}$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl," as used herein, refers to an alkyl group substituted with a heteroaryl group.

The term "heteroalkyl," as used herein, refers to a saturated or unsaturated chain of carbon atoms and at least one heteroatom, wherein no two heteroatoms are adjacent.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include 5- to 10-membered cyclic or polycyclic ring systems, including, for example, pyrrole, furan, thiophene, imidazole, oxazole, thiazole, pyrazole, pyridine, pyrazine, pyridazine, and pyrimidine, and the like. Exemplary optional substituents on heteroaryl groups include those substituents put forth as exemplary substituents on aryl groups, above.

The term "heteroatom" as used herein means an atom of any element other than carbon or hydrogen. Preferred heteroatoms are nitrogen, oxygen, and sulfur.

The terms "heterocycloalkyl," "heterocycle," and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocycloalkyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocycloalkyls. Heterocycloalkyl groups include, for example, piperidine, piperazine, pyrrolidine, morpholine, lactones, lactams, and the like.

The term "hydrocarbyl," as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to, aryl, heteroaryl, carbocycle, heterocyclyl, alkyl, alkenyl, alkynyl, and combinations thereof.

The term "hydroxyalkyl," as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl," for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds.

For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a haloalkyl, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulthydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —OSO$_3$H, or a pharmaceutically acceptable salt thereof.

The term "sulfonate" is art-recognized and refers to the group SO$_3$H, or a pharmaceutically acceptable salt thereof. In some embodiments, a sulfonate can mean an alkylated sulfonate of the formula SO$_3$(alkyl).

The term "thioester", as used herein, refers to a group —C(O)SR$^{10}$ or —SC(O)R$^{10}$ wherein R$^{10}$ represents a hydrocarbyl.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3$^{rd}$ Ed., 1999, John Wiley & Sons, NY and Harrison et al., *Compendium of Synthetic Organic Methods*, Vols. 1-8, 1971-1996, John Wiley & Sons, NY. Representative nitrogen protecting groups include, but are not limited to, formyl, acetyl, trifluoroacetyl, benzyl, benzoyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated (esterified) or alkylated such as benzyl and trityl ethers (e.g., PMB ethers), as well as alkyl ethers, tetrahydropyranyl ethers, trialkylsilyl ethers (e.g., TMS or TIPS groups), glycol ethers, such as ethylene glycol and propylene glycol derivatives and allyl ethers.

Exemplary Methods

Provided herein are methods for preparing a compound of Formula (IX):

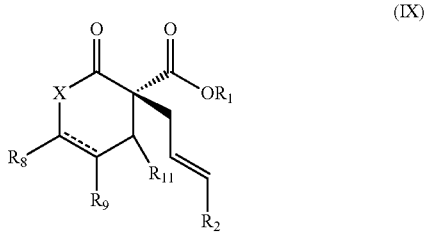

comprising:
treating a compound of Formula (I)

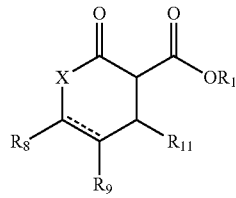

with a compound of Formula (IIa) or (IIb)

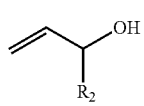

in an organic solvent
in the presence of a complex formed by contacting a Ni(0) source with a ligand L;
wherein:
X is O or N-PG;
PG is a protecting group;
R$_1$ is C$_{1-5}$ alkyl;
R$_2$ is H, C$_{1-5}$ alkyl, C$_{1-5}$ alkenyl, aralkyl, aralkenyl, aryl, or hetaryl;
⟜ is a single bond or a double bond, as valence permits; and
one following:
(i) R$_8$, R$_9$, and R$_{11}$ are each H;
(ii) R$_8$ is H, and R$_9$ and R$_{11}$, taken together with the carbon atoms to which they are attached, form a heterocyclic, carbocyclic, aryl, or hetaryl ring; or
(iii) R$_{10}$ is H, R$_8$ and R$_9$, taken together with the carbon atoms to which they are attached, form a heterocyclic, carbocyclic, aryl, or hetaryl ring.

In certain embodiments, L is selected from L1, L2, L3, L4, L5, L6, L7, L8, L9, L10, L11, L12, L13, L14, L15, L16, L17, L18, L19, L20, L21, L22, L23, L24, L25, L26, L27, L28, L29, L30, L31, L32, L33. L34, L35, L36, L37, L38, L39, and L40. In preferred embodiments, L is selected from (R)-BINAP, (R)—Hs-BINAP, (R)-Segphos, and (R)—P-phos. Even more preferably, L is (R)—P-phos.

In some embodiments, X is O and the solvent is diethyl ether. In preferred embodiments, L is (R)—P-phos.

In other embodiments, X is N-PG.

In certain embodiments, X is N-PG and PG is selected from benzoyl, Boc, methyl, and phenyl, preferably, PG is benzoyl.

In some embodiments, the Ni(0) source is Ni(COD)$_2$.

In certain other embodiments, the organic solvent is toluene, diethyl ether, methyl t-butyl ether, tetrahydrofuran, or dioxane, or a mixture thereof.

In some embodiments, R$_8$ and R$_9$, taken together with the carbon atoms to which they are attached, form a 5- or 6-membered heterocyclic, carbocyclic, aryl, or hetaryl ring.

In some embodiments, R$_8$ and R$_9$, taken together with the carbon atoms to which they are attached, form a 5- or 6-membered heterocyclic or carbocyclic ring; and ⟜ is a single bond.

In some embodiments, $R_8$ and $R_9$, taken together with the carbon atoms to which they are attached, form a 5- or 6-membered aryl or hetaryl ring; and ⇌ is a double bond.

In some embodiments, the compound of Formula (IX) is a compound of Formula (III):

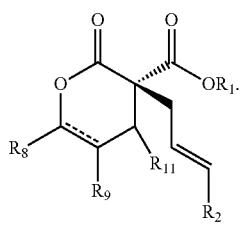

(III)

In some embodiments, the compound of Formula (IX) is a compound of Formula (V):

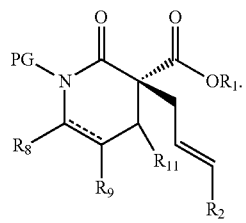

(V)

In some embodiments, the compound of Formula (I) is a compound of Formula (Ia):

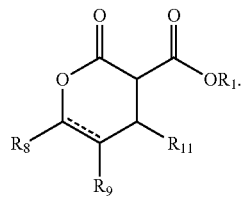

(Ia)

In some embodiments, the compound of Formula (I) is a compound of Formula (IV):

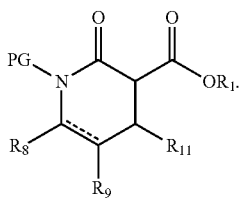

(IV)

In some embodiments, X is O and the organic solvent is diethyl ether. In certain preferred embodiments, L is (R)—P-phos. In certain preferred embodiments, 10 mol % of the Ni(0) source and 12 mol % of (R)—P-phos are used. In some such embodiments, the reaction temperature is at or above 0° C. In other such embodiments, the reaction temperature is below 0° C. In some embodiments, $R_1$ is methyl or ethyl. In certain preferred embodiments, $R_2$ is hetaryl, aralkenyl,

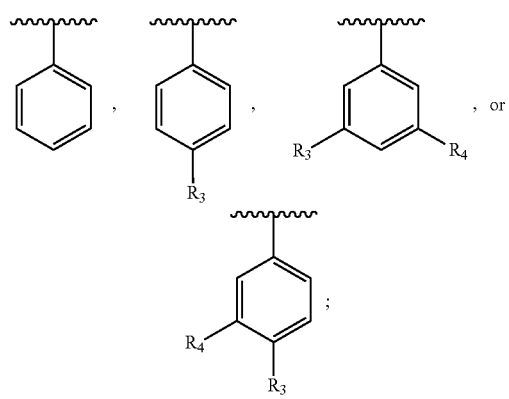

wherein $R_3$ is $C_{1-5}$ alkyl or $C_{1-5}$ alkoxy, $R_4$ is $C_{1-5}$ alkyl or $C_{1-5}$ alkoxy, or $R_3$ and $R_4$, when ortho to each other, combine to form an aryl or hetaryl ring.

In other embodiments, X is N-PG and PG is benzoyl. In some such embodiments, $R_1$ is methyl or ethyl; $R_2$ is H or aryl; and L is (R)—P-phos. In some such embodiments, 10 mol % of the Ni(0) source and 12 mol % of (R)—P-phos are used. In some such embodiments, the reaction temperature is between about 10° C. and about 25° C.

Also provided herein are methods of preparing a compound of Formula (XI):

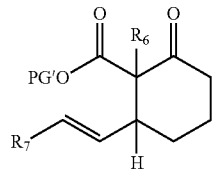

(XI)

comprising treating a compound of Formula (XII)

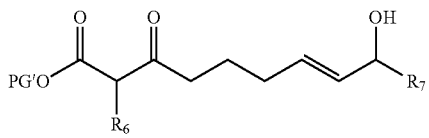

(XII)

in an organic solvent
in the presence of a complex formed by contacting a Ni(0) source with a ligand L,
wherein
PG' is an oxygen protecting group;
$R_6$ is $C_{1-5}$ alkyl;
$R_7$ is $C_{1-5}$ alkyl.

In some embodiments, the Ni(0) source is Ni(COD)$_2$.

In certain other embodiments, the organic solvent is toluene, diethyl ether, methyl t-butyl ether, tetrahydrofuran, or dioxane, or a mixture thereof.

In some embodiments, the oxygen protecting group is PMB.

In some embodiments, the Ni(0) source is Ni(COD)$_2$; L is (S)-C3-TunePhos; and the organic solvent is diethyl ether. In certain preferred embodiments, $R_6$ is methyl; $R_7$ is methyl; and PG' is PMB.

Also provided herein are methods comprising:
preparing a compound of Formula (IX) as described herein, or preparing a compound of Formula (XI) as described herein; and synthesizing a pharmaceutical agent from the compound of Formula (IX), or synthesizing a pharmaceutical agent from the compound of Formula (XI).

For example, also provided herein are methods of preparing a compound of Formula (VI):

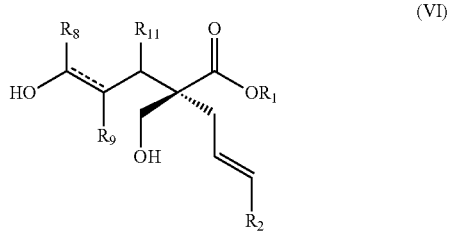

(VI)

comprising treating a compound of Formula (III)

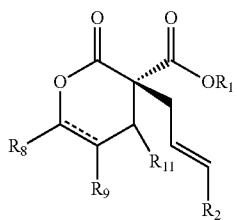

(III)

with a reducing agent;
wherein
$R_1$ is $C_{1-5}$ alkyl;
$R_2$ is H, $C_{1-5}$ alkyl, $C_{1-5}$ alkenyl, aralkyl, aralkenyl, aryl, or hetaryl;
⦂⦂ bond or a double bond, as valence permits; and
one of the following:
(i) $R_8$, $R_9$, and $R_{11}$ are each H;
(ii) $R_8$ is H, and $R_9$ and $R_{11}$, taken together with the carbon atoms to which they are attached, form a heterocyclic, carbocyclic, aryl, or hetaryl ring; or
(iii) $R_{11}$ is H, and $R_8$ and $R_9$, taken together with the carbon atoms to which they are attached, form a heterocyclic, carbocyclic, aryl, or hetaryl ring.

In some such embodiments, $R_1$ is ethyl and $R_2$ is H. In some embodiments, $R_8$, $R_9$, and $R_{11}$ are each H. Any reducing agent may be used. Examples of suitable reducing agents include, but are not limited to, sodium borohydride ($NaBH_4$), lithium tri-t-butoxy aluminum hydride, and sodium cyanoborohydride. In certain preferred embodiments, the reducing agent is $NaBH_4$. The reducing agent is suitably used in excess over the compound of Formula (III). For example, the reducing agent may be used in the range of about 1 to about 10 equivalents relative to the compound of Formula (II), such as about 2 equivalents, about 3 equivalents, about 4 equivalents, about 5 equivalents, about 6 equivalents, about 7 equivalents, about 8 equivalents, about 9 equivalents, or about 10 equivalents relative to the compound of Formula (III). In certain preferred embodiments, about 5 equivalents of the reducing are used relative to the compound of Formula (III).

As another example, also provided herein are methods of preparing a compound of Formula (VII):

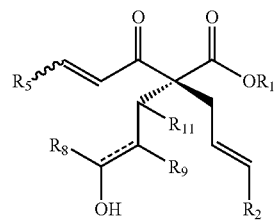

(VII)

comprising treating a compound of Formula (III)

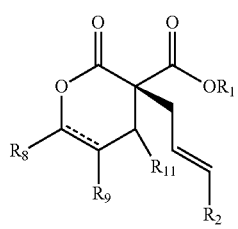

(III)

with a compound of Formula (X)

(X)

wherein
$R_1$ is $C_{1-5}$ alkyl;
$R_2$ is H, $C_{1-5}$ alkyl, $C_{1-5}$ alkenyl, aralkyl, aralkenyl, aryl, or hetaryl;
$R_5$ is H, $C_{1-5}$ alkyl, or $C_{1-5}$ alkenyl;
⦂⦂ is a single bond or a double bond, as valence permits;
and one of the following:
(i) $R_8$, $R_9$, and $R_{11}$ are each H;
(ii) $R_8$ is H, and $R_9$ and $R_{11}$, taken together with the carbon atoms to which they are attached, form a heterocyclic, carbocyclic, aryl, or hetaryl ring; or
(iii) $R_{11}$ is H, and $R_8$ and $R_9$, taken together with the carbon atoms to which they are attached, heterocyclic, carbocyclic, aryl, or hetaryl ring.

In some embodiments, $R_1$ is ethyl and $R_2$ is H. In some embodiments, $R_8$, $R_9$, and $R_{11}$ are each H.

As yet another example, also provided herein are methods of preparing a compound of Formula (VIII):

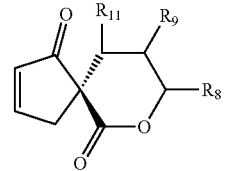

(VIII)

comprising synthesizing the compound of Formula (VII) as described herein, and treating the compound of Formula (VII) with a ring-closing metathesis catalyst.

Transition Metal Catalysts

Preferred transition metal catalysts of the invention are complexes of nickel. In some embodiments, the transition metal catalyst is a nickel catalyst.

In some embodiments, the nickel catalyst is prepared by combining a nickel source, such as a Ni(0) source, and a chiral ligand. In preferred embodiments the nickel catalyst is prepared by combining a nickel source and a chiral ligand.

Exemplary nickel sources that may be used in the methods of the invention include, but are not limited to. In preferred embodiments, the nickel source is bis(1,5-cyclooctadiene)nickel(0) (Ni(COD)$_2$).

Accordingly, when describing the amount of transition metal catalyst used in the methods of the invention, the following terminology applies. The amount of transition metal catalyst present in a reaction is alternatively referred to herein as "catalyst loading". Catalyst loading may be expressed as a percentage that is calculated by dividing the moles of catalyst complex by the moles of the substrate present in a given reaction. Catalyst loading is alternatively expressed as a percentage that is calculated by dividing the moles of total transition metal (for example, nickel) by the moles of the substrate present in a given reaction.

In certain embodiments, the transition metal catalyst is present under the conditions of the reaction from an amount of about 0.01 mol % to about 10 mol % total nickel relative to the substrate, which is the compound of Formula (I), (Ia), (IV), or (XII). In certain embodiments, the catalyst loading is from about 0.05 mol % to about 8 mol % total nickel relative to the substrate. In certain embodiments, the catalyst loading is from about 0.05 mol % to about 8 mol %, about 1 mol % to about 8 mol % about 1.5 mol % to about 8 mol % about 2 mol % to about 8 mol %, about 2.5 mol % to about 8 mol %, about 3 mol % to about 8 mol %, about 3.5 mol % to about 8 mol %, about 3.5 mol % to about 7.5 mol %, about 3.5 mol % to about 7 mol %, about 3.5 mol % to 6.5 mol %, about 3.5 mol % to about 6 mol %, about 3.5 mol % to about 5.5 mol %, about 3.5 mol % to about 5 mol %, about 3.5 mol % to about 4.5 mol % total nickel relative to the substrate. In some embodiments, the catalyst loading is from about 0.05 mol % to about 7.5 mol %, about 0.05 mol % to about 7 mol %, about 0.05 mol % to about 6.5 mol %, about 0.05 mol % to about 6 mol %, about 0.05 mol % to about 5.5 mol %, about 0.05 mol % to about 5 mol %, about 0.05 mol % to about 4.5 mol %, or about 0.05 mol % to about 4 mol % total nickel relative to the substrate. In some embodiments, the catalyst loading is from about 1 mol % to about 8 mol %, about 1 mol % to about 7.5 mol %, about 1 mol % to about 7 mol %, about 1 mol % to about 6.5 mol %, about 1 mol % to about 6 mol %, about 1 mol % to about 5.5 mol %, about 1 mol % to about 5 mol %, about 1 mol % to about 4.5 mol %, or about 1 mol % to about 4 mol % total nickel relative to the substrate. In some embodiments, the catalyst loading is from about 1.5 mol % to about 8 mol %, about 1.5 mol % to about 7.5 mol %, about 1.5 mol % to about 7 mol %, about 1.5 mol % to about 6.5 mol %, about 1.5 mol % to about 6 mol %, about 1.5 mol % to about 5.5 mol %, about 1.5 mol % to about 5 mol %, about 1.5 mol % to about 4.5 mol %, or about 1.5 mol % to about 4 mol % total nickel relative to the substrate. In some embodiments, the catalyst loading is from about 2 mol % to about 8 mol %, about 2 mol % to about 7.5 mol %, about 2 mol % to about 7 mol %, about 2 mol % to about 6.5 mol %, about 2 mol % to about 6 mol %, about 2 mol % to about 5.5 mol %, about 2 mol % to about 5 mol %, about 2 mol % to about 4.5 mol %, or about 2 mol % to about 4 mol % total nickel relative to the substrate. In some embodiments, the catalyst loading is from about 2.5 mol % to about 8 mol %, about 2.5 mol % to about 7.5 mol %, about 2.5 mol % to about 7 mol %, about 2.5 mol % to about 6.5 mol %, about 2.5 mol % to about 6 mol %, about 2.5 mol % to about 5.5 mol %, about 2.5 mol % to about 5 mol %, about 2.5 mol % to about 4.5 mol %, or about 2.5 mol % to about 4 mol % total nickel relative to the substrate. In some embodiments, the catalyst loading is from about 3 mol % to about 8 mol %, about 3 mol % to about 7.5 mol %, about 3 mol % to about 7 mol %, about 3 mol % to about 6.5 mol %, about 3 mol % to about 6 mol %, about 3 mol % to about 5.5 mol %, about 3 mol % to about 5 mol %, about 3 mol % to about 4.5 mol %, or about 3 mol % to about 4 mol % total nickel relative to the substrate. In some embodiments, the catalyst loading is from about 3.5 mol % to about 8 mol %, about 3.5 mol % to about 7.5 mol %, about 3.5 mol % to about 7 mol %, about 3.5 mol % to about 6.5 mol %, about 3.5 mol % to about 6 mol %, about 3.5 mol % to about 5.5 mol %, about 3.5 mol % to about 5 mol %, about 3.5 mol % to about 4.5 mol %, or about 3.5 mol % to about 4 mol % total nickel relative to the substrate. For example, in certain embodiments, the catalyst loading is about 0.01 mol %, about 0.05 mol %, about 0.1 mol %, about 0.15 mol %, about 0.2 mol %, about 0.25 mol %, about 0.3 mol %, about 0.4 mol %, about 0.5 mol %, about 0.6 mol %, about 0.7 mol %, about 0.8 mol %, about 0.9 mol %, about 1 mol %, about 1.5 mol %, about 2 mol %, about 3 mol %, or about 5 mol % total nickel. In certain other embodiments, the catalyst loading is about 0.5 mol %, about 0.75 mol %, about 1 mol %, about 1.25 mol %, about 1.5 mol %, about 1.75 mol %, about 2 mol %, about 2.25 mol %, about 2.5 mol %, about 2.75 mol %, about 3 mol %, about 3.25 mol %, about 3.5 mol %, about 3.75 mol %, about 4 mol %, about 4.25 mol %, about 4.5 mol %, about 4.75 mol %, about 5 mol %, about 5.25 mol %, about 5.5 mol %, about 5.75 mol %, about 6 mol %, about 6.25 mol %, about 6.5 mol %, about 6.75 mol %, about 7 mol %, about 7.25 mol %, about 7.5 mol %, about 7.75 mol %, about 8 mol %, about 8.25 mol %, about 8.5 mol %, about 8.75 mol %, about 9 mol %, about 9.25 mol %, about 9.5 mol %, about 9.75 mol %, about 10 mol %, about 10.25 mol %, about 10.5 mol %, about 10.75 mol %, about 11 mol %, about 11.25 mol %, about 11.5 mol %, about 11.75 mol %, or about 12 mol % total nickel. In preferred embodiments, the catalyst loading is about 10 mol % total nickel.

Chiral Ligands

One aspect of the invention relates to the enantioselectivity of the methods. Enantioselectivity results from the use of chiral ligands during the allylic alkylation reaction. Accordingly, the nickel catalyst comprises a chiral ligand. Without being bound by theory, the asymmetric environment that is created around the metal center by the presence of chiral ligands produces an enantioselective reaction. The chiral ligand forms a complex with the transition metal (i.e., nickel), thereby occupying one or more of the coordination sites on the metal and creating an asymmetric environment around the metal center. This complexation may or may not involve the displacement of achiral ligands already complexed to the metal. When displacement of one or more achiral ligands occurs, the displacement may proceed in a concerted fashion, i.e., with both the achiral ligand decomplexing from the metal and the chiral ligand complexing to the metal in a single step. Alternatively, the displacement may proceed in a stepwise fashion, i.e., with decomplexing of the achiral ligand and complexing of the chiral ligand occurring in distinct steps. Complexation of the chiral ligand to the transition metal may be allowed to occur in situ, i.e., by admixing the ligand and metal before adding the substrate. Alternatively, the ligand-metal complex can be formed separately, and the complex isolated before use in the alkylation reactions of the present invention.

Once coordinated to the transition metal center, the chiral ligand influences the orientation of other molecules as they interact with the transition metal catalyst. Coordination of the metal center with a π-allyl group and reaction of the substrate with the π-allyl-metal complex are dictated by the presence of the chiral ligand. The orientation of the reacting species determines the stereochemistry of the products.

Chiral ligands of the invention may be bidentate or monodentate or, alternatively, ligands with higher denticity (e.g., tridentate, tetradentate, etc.) can be used. In preferred embodiments, the ligand is a bidentate ligand. Additionally, it is preferred that the ligand be substantially enantiopure. By "enantiopure" is meant that only a single enantiomer is present. In many cases, substantially enantiopure ligands (e.g., ee>99%, preferably ee>99.5%, even more preferably ee>99.9%) can be purchased from commercial sources, obtained by successive recrystallizations of an enantioenriched substance, or by other suitable means for separating enantiomers.

In certain embodiments, the chiral ligand is an enantioenriched phosphorous-based ligand. In certain embodiments, the enantioenriched phosphorus-based ligand is a bisphosphine ligand. In certain embodiments, the chiral ligand is selected from:

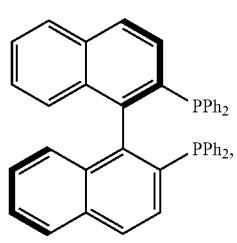

(R)-BINAP
L1

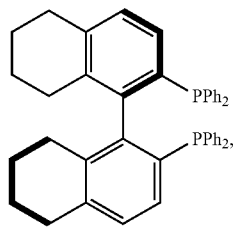

(R)-H$_8$—BINAP
L2

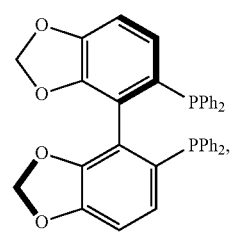

(R)-Segphos
L3

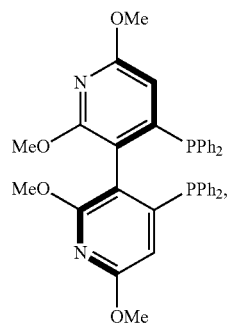

(R)-P-phos
L4

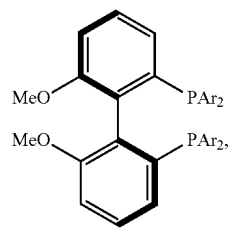

L5: Ar = 3,5-t-Bu$_2$C$_6$H$_3$
L6: Ar = 3,5-t-Bu$_2$-4-MeOC$_6$H$_2$

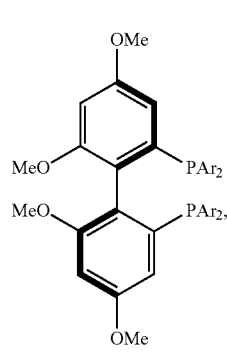

Ar = 3,5-(CF$_3$)$_2$C$_6$H$_3$
L7

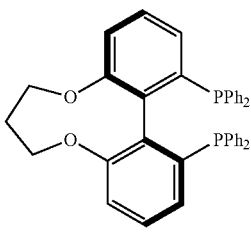

L8

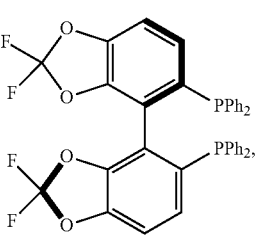

L9

-continued
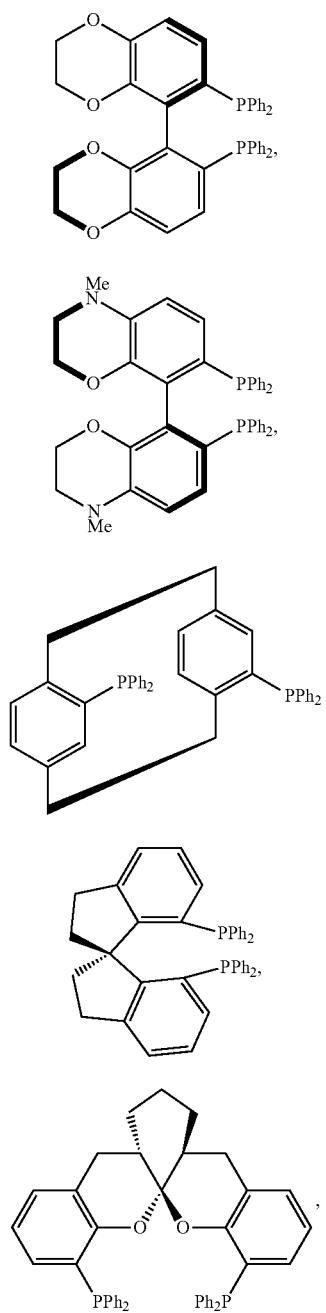
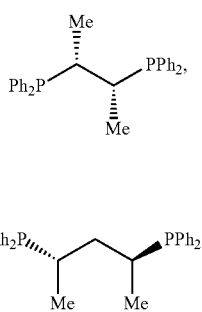
-continued
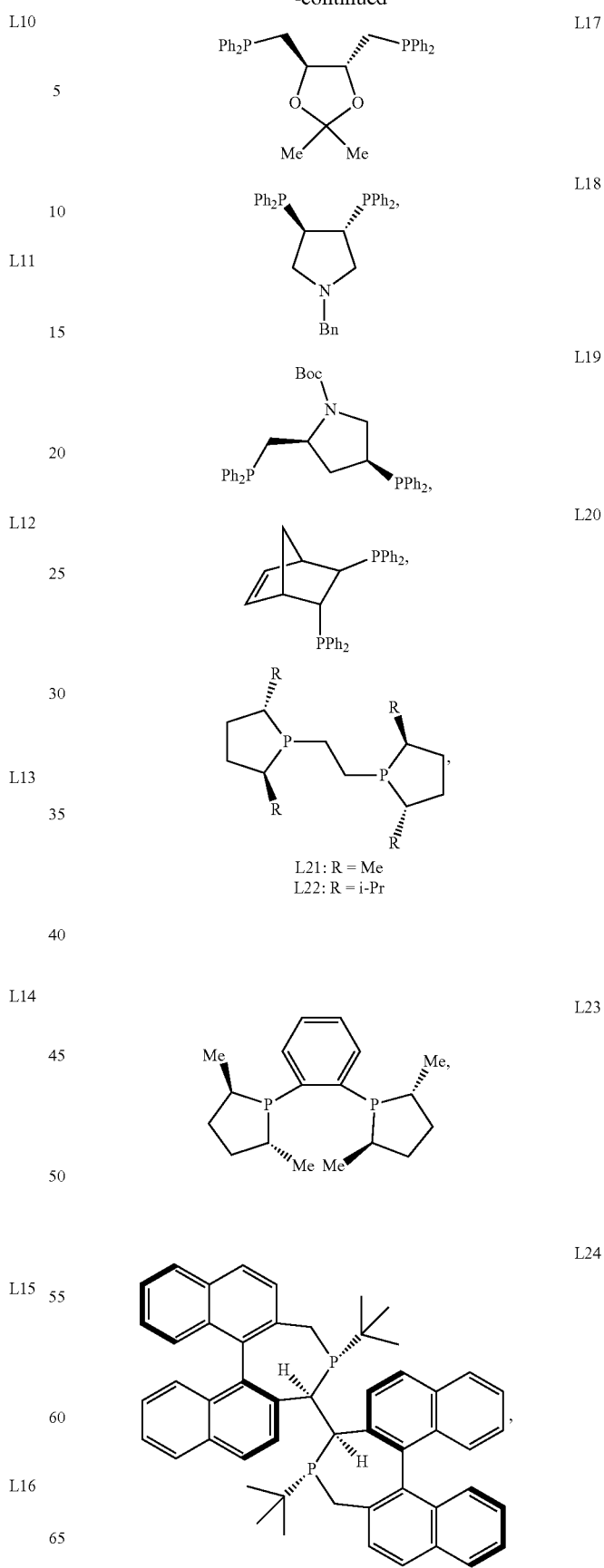

-continued
L25
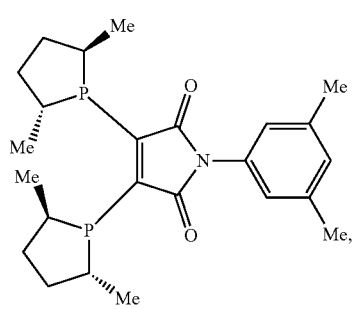
L26
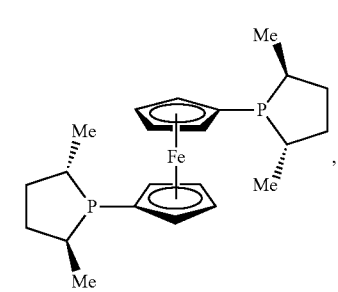
L27
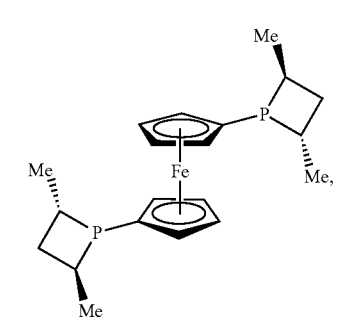
L28
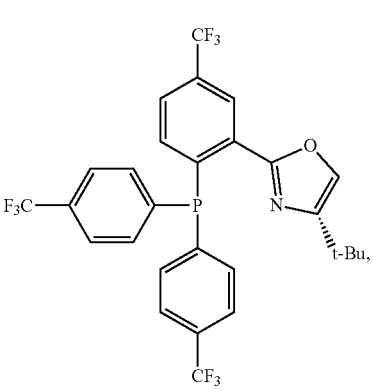
L29
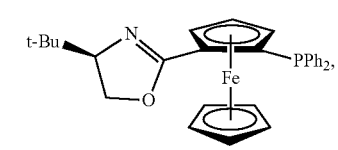
-continued
L30
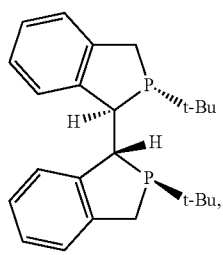
L31
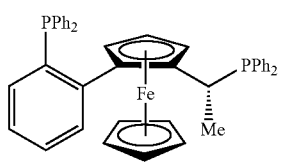
L32
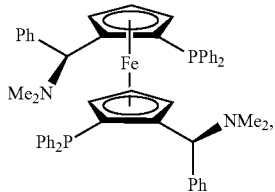
L33
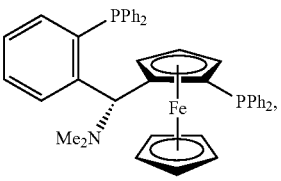
L34
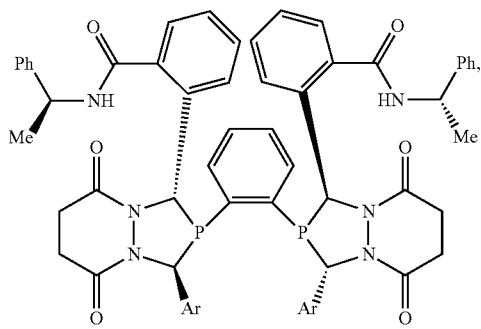
L35
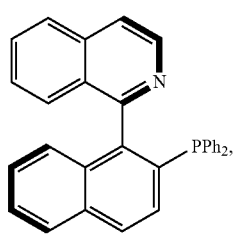

-continued
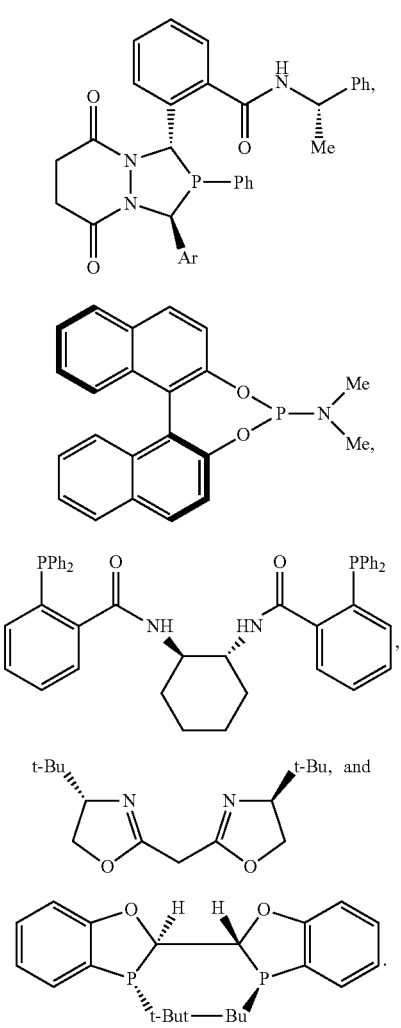
Preferred bisphosphine ligands include:
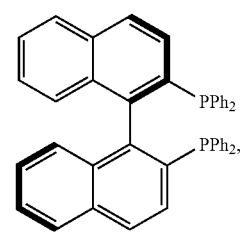
(R)-BINAP
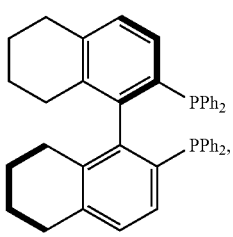
(R)-H₈—BINAP
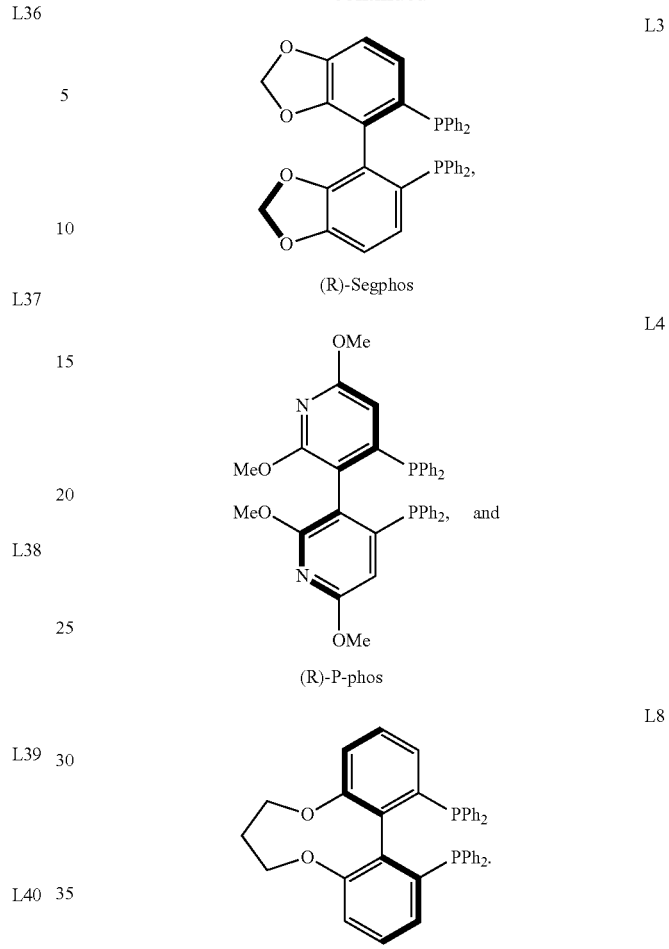
Bisphosphine ligand L8 is also known as (S)-C3-TunePhos.
In certain preferred embodiments, the ligand is
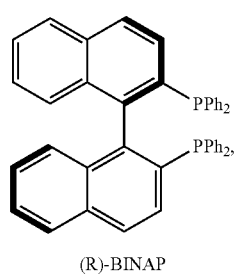
(R)-BINAP
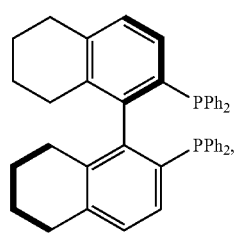
(R)-H₈—BINAP

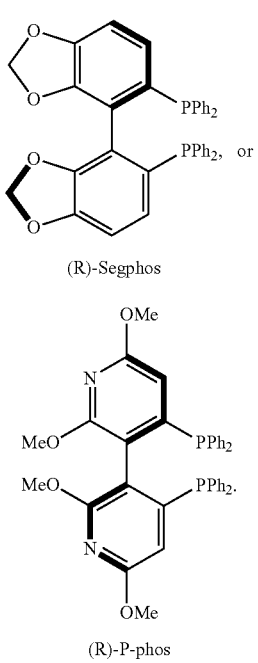

(R)-Segphos (R)-P-phos

In other preferred embodiments, the ligand is

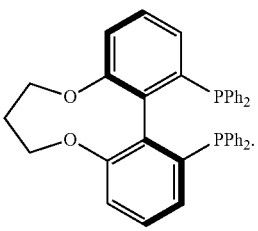

Generally, the chiral ligand is present in an amount in the range of about 1 equivalent to about 20 equivalents relative to the amount of total metal from the catalyst, preferably in the range of about 1 to about 15 equivalents relative to the amount of total metal from the catalyst, and most preferably in the range of about 1 equivalent relative to the amount of total metal from the catalyst. Alternatively, the amount of the chiral ligand can be measured relative to the amount of the substrate.

In certain embodiments, the ligand is present under the conditions of the reaction from an amount of about 0.1 mol % to about 100 mol % relative to the substrate, which is the compound of Formula (I), (Ia), (IV), or (XII). The amount of the chiral ligand present in the reaction is alternatively referred to herein as "ligand loading" and is expressed as a percentage that is calculated by dividing the moles of ligand by the moles of the substrate present in a given reaction. In certain embodiments, the ligand loading is from about 1 mol %, about 1.1 mol %, about 1.2 mol %, about 1.3 mol %, about 1.4 mol %, about 1.5 mol %, about 1.6 mol %, about 1.7 mol %, about 1.8 mol %, about 1.9 mol %, about 2 mol %, about 2.1 mol %, about 2.2 mol %, about 2.3 mol %, about 2.4 mol %, about 2.5 mol %, about 2.6 mol %, about 2.7 mol %, about 2.8 mol %, about 2.9 mol %, about 3 mol %, about 3.1 mol %, about 3.2 mol %, about 3.3 mol %, about 3.4 mol %, about 3.5 mol %, about 3.6 mol %, about 3.7 mol %, about 3.8 mol %, about 3.9 mol %, about 4 mol %, about 4.1 mol %, about 4.2 mol %, about 4.3 mol %, about 4.4 mol %, about 4.5 mol %, about 4.6 mol %, about 4.7 mol %, about 4.8 mol %, about 4.9 mol %, about 5 mol %, about 5.1 mol %, about 5.2 mol %, about 5.3 mol %, about 5.4 mol %, about 5.5 mol %, about 5.6 mol %, about 5.7 mol %, about 5.8 mol %, about 5.9 mol %, about 6 mol %, about 6.1 mol %, about 6.2 mol %, about 6.3 mol %, about 6.4 mol %, about 6.5 mol %, about 6.6 mol %, about 6.7 mol %, about 6.8 mol %, about 6.9 mol %, about 7 mol %, about 7.1 mol %, about 7.2 mol %, about 7.3 mol %, about 7.4 mol %, about 7.5 mol %, about 7.6 mol %, about 7.7 mol %, about 7.8 mol %, about 7.9 mol %, about 8 mol %, about 8.1 mol %, about 8.2 mol %, about 8.3 mol %, about 8.4 mol %, about 8.5 mol %, about 8.6 mol %, about 8.7 mol %, about 8.8 mol %, about 8.9 mol %, about 9 mol %, about 9.1 mol %, about 9.2 mol %, about 9.3 mol %, about 9.4 mol %, about 9.5 mol %, about 9.6 mol %, about 9.7 mol %, about 9.8 mol %, about 9.9 mol %, about 10 mol %, about 10.1 mol %, about 10.2 mol %, about 10.3 mol %, about 10.4 mol %, about 10.5 mol %, about 10.6 mol %, about 10.7 mol %, about 10.8 mol %, about 10.9 mol %, about 11 mol %, about 11.1 mol %, about 11.2 mol %, about 11.3 mol %, about 11.4 mol %, about 11.5 mol %, about 11.6 mol %, about 11.7 mol %, about 11.8 mol %, about 11.9 mol %, about 12 mol %, about 15 mol %, about 20 mol %, or about 25 mol %. In preferred embodiments, the ligand loading is 12 mol %.

Where a chiral ligand is used, the reactions of the invention may enrich the stereocenter bearing the $R^1$- and $R^2$-connected fragments in the product relative to the enrichment at this center, if any, of the starting material. In certain embodiments, the chiral ligand used in the methods of the invention yields a compound of Formula (IX), (VI), (VII), (VIII), or (XI) that is enantioenriched. The level of enantioenrichment of a compound may be expressed as enantiomeric excess (ee). The ee of a compound may be measured by dividing the difference in the fractions of the enantiomers by the sum of the fractions of the enantiomers. For example, if a compound is found to comprise 98% (S)-enantiomer, and 2% (R) enantiomer, then the ee of the compound is (98−2)/(98+2), or 96%. In certain embodiments, the compound of formula (IX), (VI), (VII), (VIII), or (XI) has about 30% ee or greater, about 40% ee or greater, about 50% ee or greater, 60% ee or greater, about 65% ee or greater, about 70% ee or greater, about 75% ee or greater, about 80% ee or greater, about 85% ee or greater, about 88% ee or greater, about 90% ee or greater, about 91% ee or greater, about 92% ee or greater, about 93% ee or greater, about 94% ee or greater, about 95% ee or greater, about 96% ee or greater, about 97% ee or greater, about 98% ee or greater, or about 99% ee or greater, even where this % ee is greater than the % ee of the starting material, such as 0% ee (racemic).

In certain embodiments, the compound of formula (IX), (VI), (VII), (VIII), or (XI) is enantioenriched. In certain embodiments, the compound of formula (IX), (VI), (VII), (VIII), or (XI) is enantiopure.

In embodiments where the starting material has more than one stereocenter, reactions of the invention may enrich the stereocenter bearing the $R^1$- and $R^2$-connected fragments relative to the enrichment at this center, if any, of the starting material, and substantially independently of the stereochemical disposition/enrichment of any other stereocenters of the molecule. For example, a product of the methods described herein may have about 30% ee or greater, about 40% ee or greater, about 50% ee or greater, about 60% ee or greater, about 70% ee or greater, about 80% ee or greater, about 90% ee or greater, about 95% ee or greater, about 98% ee or greater, or even about 99% ee or greater at the stereocenter of the product bearing the $R^1$- and $R^2$-connected fragments.

Alkylation Conditions

In certain embodiments, the methods of the invention include treating a compound of Formula (I), (Ia), or (IV), with a compound of Formula (IIa) or (IIb), in the presence of a nickel catalyst, for example, a nickel catalyst prepared by contacting a Ni(0) source with a ligand, or alternatively treating a compound of Formula (XII) with a nickel catalyst, for example, a nickel catalyst prepared by contacting a Ni(0) source with a ligand, under alkylation conditions. In certain embodiments, alkylation conditions of the reaction include one or more organic solvents.

In certain embodiments, organic solvents include aromatic or non-aromatic hydrocarbons, ethers, alkylacetates, nitriles, or combinations thereof. In certain embodiments, organic solvents include hexane, pentane, benzene, toluene, xylene, cyclic ethers such as optionally substituted tetrahydrofuran and dioxane, acyclic ethers such as dimethoxyethane, diethyl ether, methyl tert-butyl ether, and cyclopentyl methyl ether, acetonitrile, isobutyl acetate, ethyl acetate, isopropyl acetate, or combinations thereof. In preferred embodiments, the solvent is tetrahydrofuran, dioxane, toluene, diethyl ether, methyl t-butyl ether, or combinations thereof. In certain preferred embodiments, the solvent is diethyl ether. In certain preferred embodiments, the solvent is toluene, methyl t-butyl ether, or a combination thereof. Combination solvents may be mixed in any proportions, including but not limited to 1:1, 1:2, 1:3, 1:4, 1:5, 2:3, 2:5, 3:4, or 3:5. In certain preferred embodiments, the solvent is a 2:3 mixture of toluene and methyl t-butyl ether.

In certain embodiments, alkylation conditions of the reaction include a reaction temperature. In certain embodiments, the reaction temperature is ambient temperature (about 20° C. to about 26° C., such as about 23° C.). In certain embodiments, the reaction temperature is higher than ambient temperature, such as, for example, about 30° C., about 35° C., about 40° C., about 45° C., about 50° C., about 55° C., or about 60° C. In certain embodiments, the reaction temperature is lower than ambient temperature, such as, for example, about 15° C., about 10° C., about 5° C., about 0° C., about −5° C., about −10° C., or about −15° C. Reaction temperature may be optimized per each substrate.

In certain embodiments, instruments such as a microwave reactor may be used to accelerate the reaction time. Pressures range from atmospheric to pressures typically used in conjunction with supercritical fluids, with the preferred pressure being atmospheric.

Exemplary Syntheses of Compound Libraries

Diverse, small molecule compound libraries (including salts of compounds) may be generally synthesized according to Schemes 1-5.

Scheme 1.

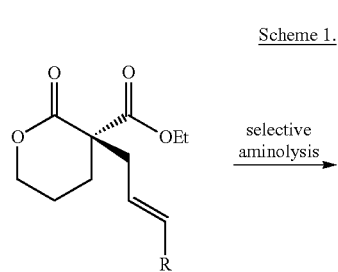

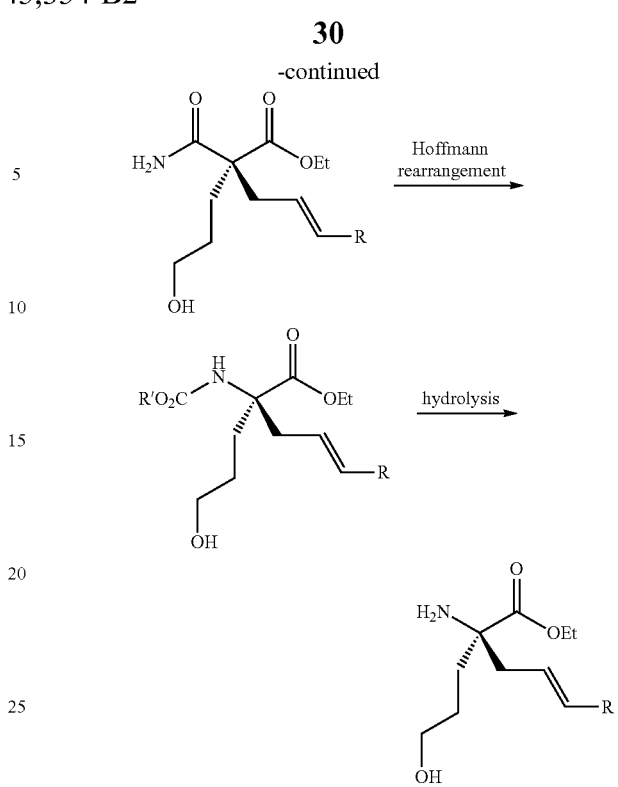

wherein R is $R^2$ as defined herein.

Scheme 2.

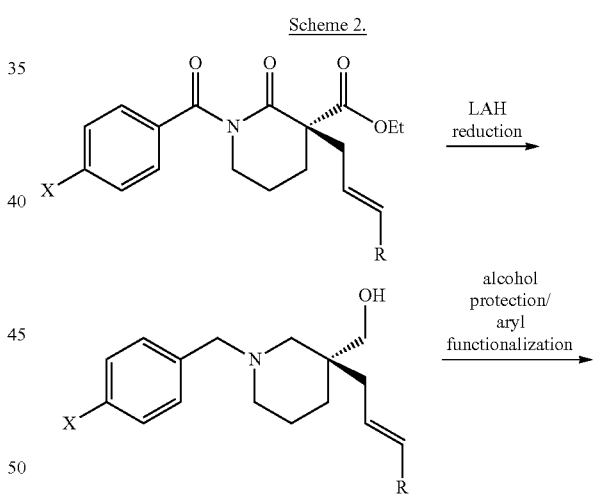

wherein, as valence and stability permit, R is $R^2$ as defined herein, R' is alkyl, aryl, alkenyl, cycloalkyl, heterocyclyl, or hetaryl, PG is a protecting group, and X is halogen (such as chloro or bromo), OTf, OMs, ONf, or OTs.

Scheme 3.

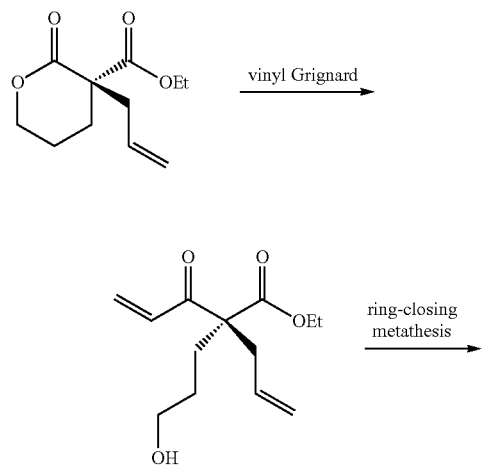

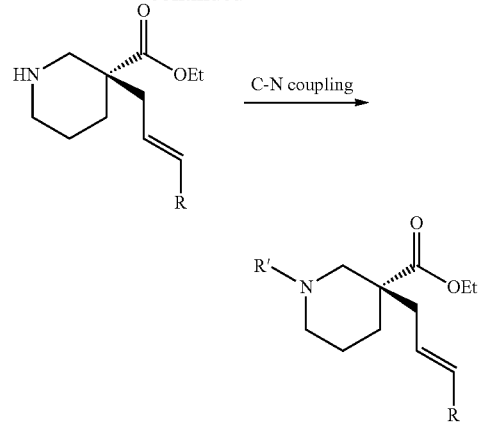

wherein, as valence and stability permit, R is $R^2$ as defined herein, and R' is alkyl, benzyl, allyl, aryl, or acyl.

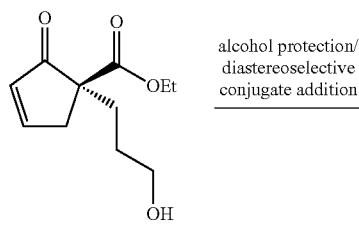

wherein, as valence and stability permit, PG is a protecting group and R is amino, alkyl, alkenyl, aryl, sulfhydryl, hydroxyl, hetaryl, oxo-alkyl, or any other nucleophilic group known to those of ordinary skill in the art.

Scheme 4

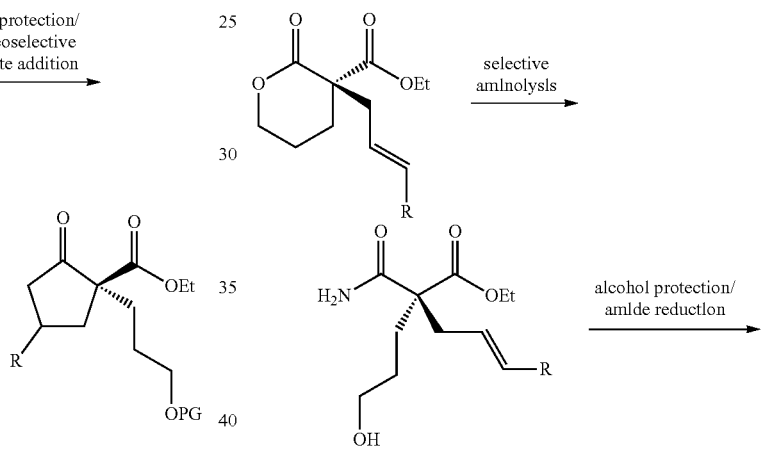

Scheme 5.

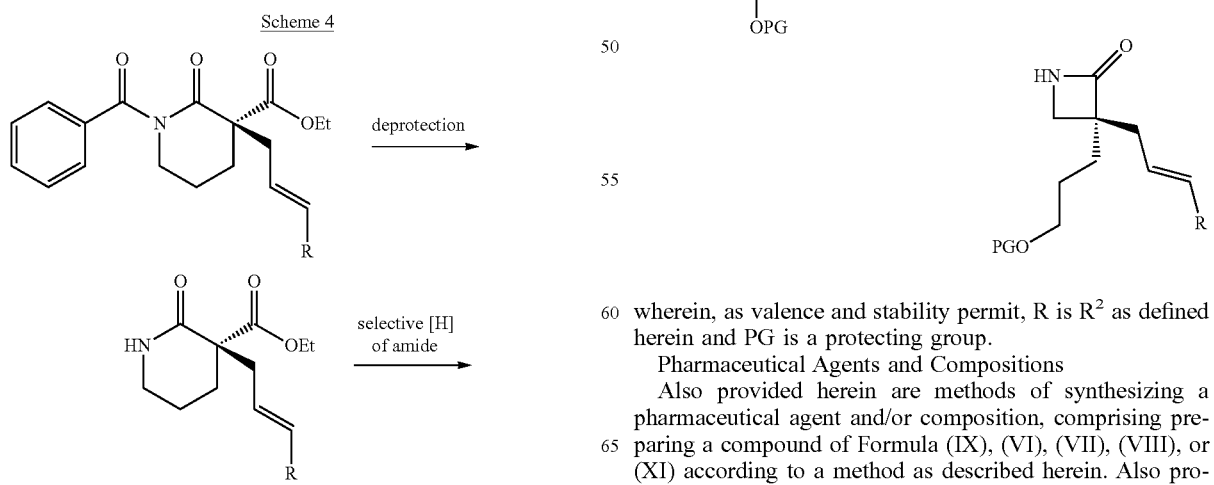

wherein, as valence and stability permit, R is $R^2$ as defined herein and PG is a protecting group.

Pharmaceutical Agents and Compositions

Also provided herein are methods of synthesizing a pharmaceutical agent and/or composition, comprising preparing a compound of Formula (IX), (VI), (VII), (VIII), or (XI) according to a method as described herein. Also provided herein are methods of synthesizing a pharmaceutical agent and/or composition, comprising preparing a compound of Formula (IX), (VI), (VII), (VIII), or (XI) according to a method as described herein and synthesizing the pharmaceutical agent and/or composition from the compound of Formula (IX), (VI), (VII), (VII), or (XI), e.g., by carrying out one or more chemical reactions on the compound of Formula (IX), (VI), (VII), (VIII), or (XI) and/or combining the pharmaceutical agent with one or more pharmaceutically acceptable carriers and/or excipients.

The pharmaceutical agent and/or composition prepared from the compound of Formula (IX), (VI), (VII), (VIII), or (XI) may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In preferred embodiments, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as a lotion, cream, or ointment.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Synthetic Schemes of Exemplary Pharmaceutical Products

Scheme 6.

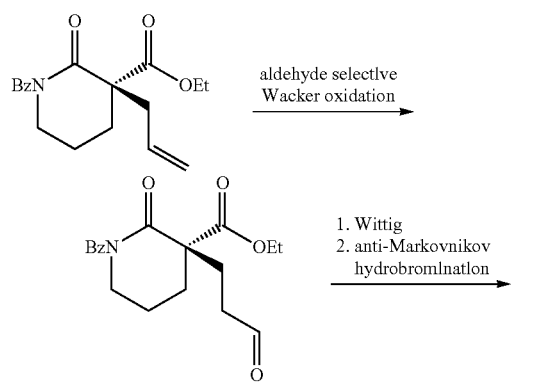

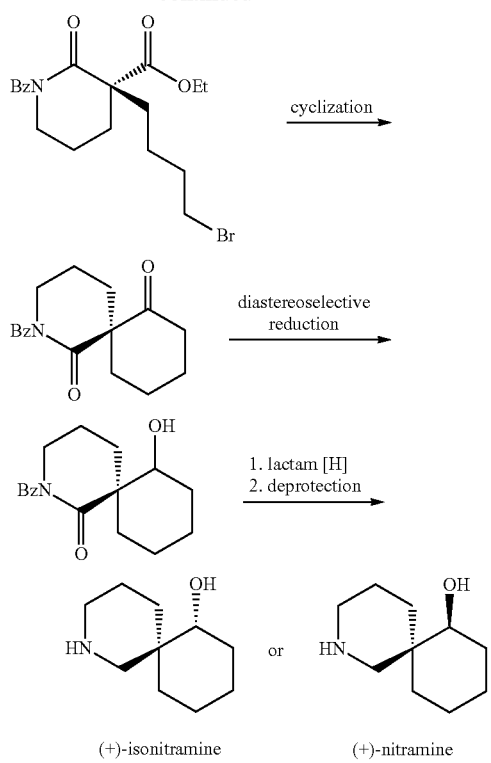

Scheme 7.

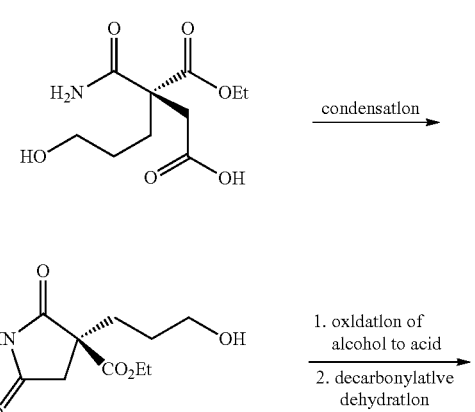

-continued

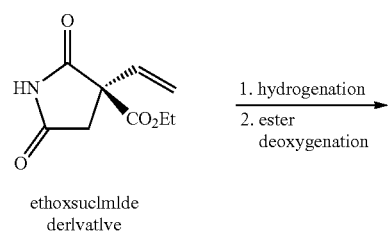

ethoxsucimide derivative 1. hydrogenation
2. ester deoxygenation
→

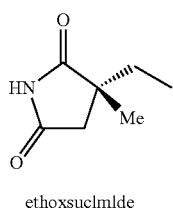

ethoxsucimide

Scheme 8.

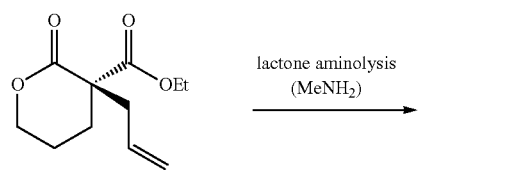

lactone aminolysis (MeNH₂)
→

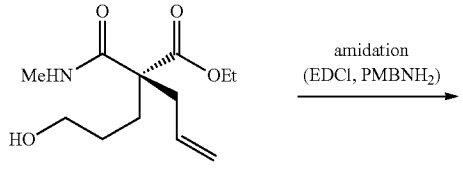

amidation (EDCl, PMBNH₂)
→

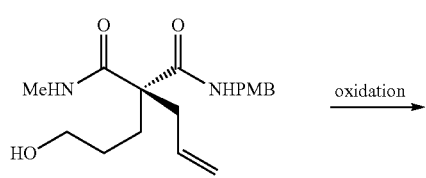

oxidation
→

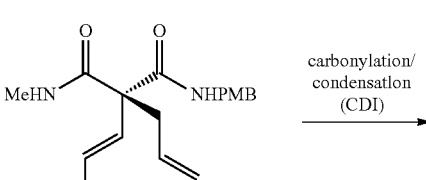

carbonylation/ condensation (CDI)
→

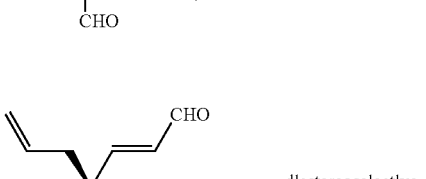

diastereoselective Michael addition
→

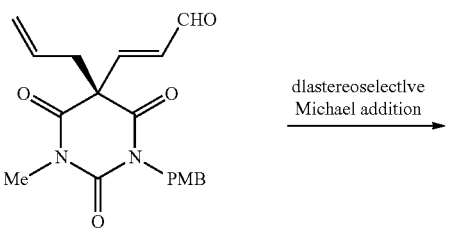

-continued

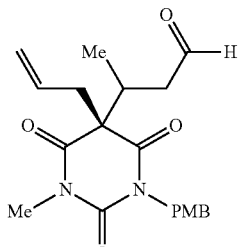

aldehyde to alkyne via enolization-elimination
→

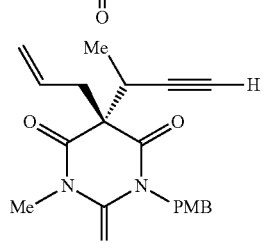

1. alkyne alkylation
2. deprotection
→

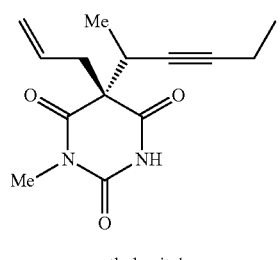

methohexital

Scheme 9.

Derivatives of ethoheptazin

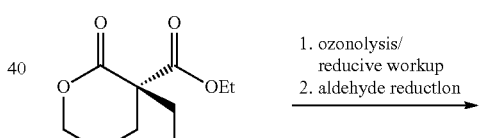

1. ozonolysis/ reductive workup
2. aldehyde reduction
→

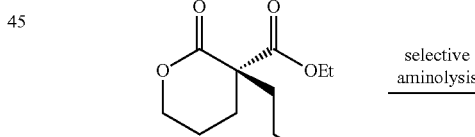

selective aminolysis
→

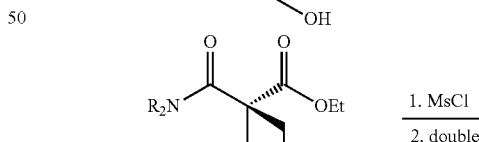

1. MsCl
2. double N-alkylation
→

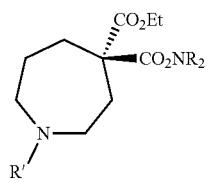

wherein, as valence and stability permit, R and R' are each independently H, alkyl, alkenyl, cycloalkyl, or aryl.

EXAMPLES

The invention now being generally described, it will be more readily understood by reference to the following examples that are included merely for purposes of illustration of certain aspects and embodiments of the present invention, and are not intended to limit the invention.

Example 1: Nickel-Catalyzed Enantioselective Allylic Alkylation of Lactones and Lactams with Unactivated Allylic Alcohols Summary The first nickel-catalyzed enantioselective allylic alkylation of lactone and lactam substrates to deliver products bearing an all-carbon quaternary stereocenter is reported. The reaction, which utilizes a commercially available chiral bisphosphine ligand, proceeds in good yield with a high level of enantioselectivity (up to 90% ee) on a range of unactivated allylic alcohols for both lactone and lactam nucleophiles. The utility of this method is further highlighted via a number of synthetically useful product transformations.

Results and Discussion

The enantioselective allylic alkylation between α-ethoxycarbonyl lactone 1a and allyl alcohol (2a) using Ni(COD)$_2$ and (R)-BINAP in diethyl ether at 0° C. was investigated. Although the α-quaternary lactone product 3aa was obtained in good yield, only moderate enantioselectivity was achieved.

A wide variety of commercially available ligand scaffolds were investigated. Chiral bisphosphine ligands were discovered to exhibit superior enantioselectivity to other classes of ligands, including those commonly used in asymmetric allylic alkylations such as phosphinooxazolines (PHOX) or C2-asymmetric ligands. In the presence of Ni(COD)$_2$ (10 mol %) and chiral bisphosphine ligands L1-L4 (12 mol %) in Et$_2$O, the reaction proceeds with moderate levels of enantioselectivity (Table 1, entries 1-4).

The highest enantiomeric excess (ee) was achieved with (R)—P-phos (L4), which delivers α-quaternary lactone 3aa in 82% yield and 82% ee (entry 4). Decreasing the catalyst loading to 5 mol % requires exceedingly long reaction time (entry 5).

An examination of different temperatures revealed that decreasing the temperature improves ee (entries 6-7), albeit with slightly diminished yields. Prolonged reaction time (48 h) at −10° C. affords product 3aa in 80% yield and 85% cee (entry 8). Importantly, a control experiment performed in the absence of the chiral ligand shows no background reaction (entry 9).

TABLE 1

Optimization of reaction parameters.[a]

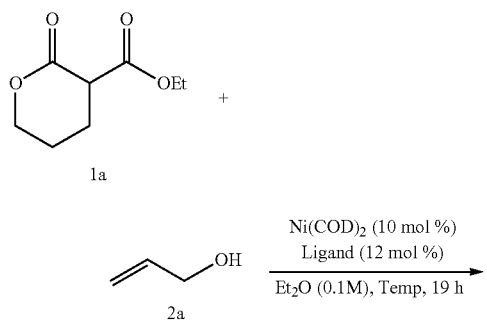

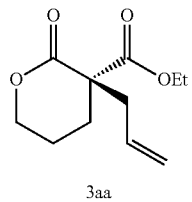

3aa

| entry | ligand | temp (° C.) | % yield[b] | % ee[c] |
|---|---|---|---|---|
| 1 | L1 | 0 | 53 | 75 |
| 2 | L2 | 0 | 76 | 78 |
| 3 | L3 | 0 | 93 | 79 |
| 4 | L4 | 0 | 82 | 82 |
| 5[d] | L4 | 0 | 62 | 81 |
| 6 | L4 | 23 | 86 | 74 |
| 7 | L4 | −10 | 69 | 84 |
| 8[e] | L4 | −10 | 80 | 85 |
| 9 | — | 0 | 0 | — |

[a]Conditions: 1a (0.1 mmol), 2a (0.1 mmol), Ni(COD)$_2$ (10 mol %), ligand (12 mol %) in Et$_2$O (1.0 mL).
[b]Yields determined by $^1$H NMR of crude reaction mixture using 1,3,5-trimethoxybenzene as a standard.
[c]Determined by chiral SFC analysis of the isolated product.
[d]Ni(COD)$_2$ (5 mol %) and L4 (6 mol %) were used.
[e]Reaction time = 48 h.

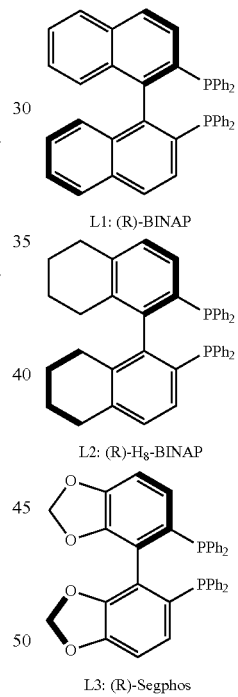

L1: (R)-BINAP

L2: (R)-H$_8$-BINAP

L3: (R)-Segphos

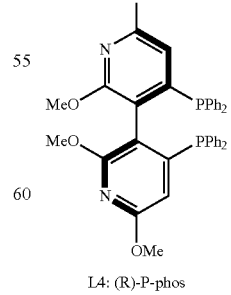

L4: (R)-P-phos

The scope of this asymmetric transformation was investigated (Table 2). The reaction of α-methoxycarbonyl lactone 1b, possessing a smaller alkyl group at the ester fragment, with allyl alcohol (2a) provides α-quaternary lactone 3ba in comparable yield and ee to the allylated product 3aa. Bicyclic lactone 1c could also be used to furnish product 3ca in slightly diminished yield and enantioselectivity. With respect to the electrophile scope, reactions between lactone 1a with various substituted allyl alcohols proceed with good ee (78-90% ee) at increased temperature (10° C.). Although a trend in enantioselectivity was not observed, the electronic nature of the aryl substituent does affect the reactivity. Electrophiles containing electron rich aryl substituents provide the corresponding products in greater yields than their electron-deficient counterparts (3ac-3ag). Furthermore, para- and meta-substituted aryl rings exhibited higher reactivity as compared to the ortho-substituted aryl ring (3ac, 3ah-ai vs. 3aj). Apart from the aryl-substituted electrophiles, heteroaryl substitution is also well-tolerated (3ak-3al). The reaction with an aliphatic electrophile affords product 3am in slightly diminished yield and ee. In addition, an alkenyl-substituted electrophile fares well under the reaction conditions, delivering product 3an in an excellent 91% yield and 88% ee.

TABLE 2

Nucleophile and electrophile scope.[a]

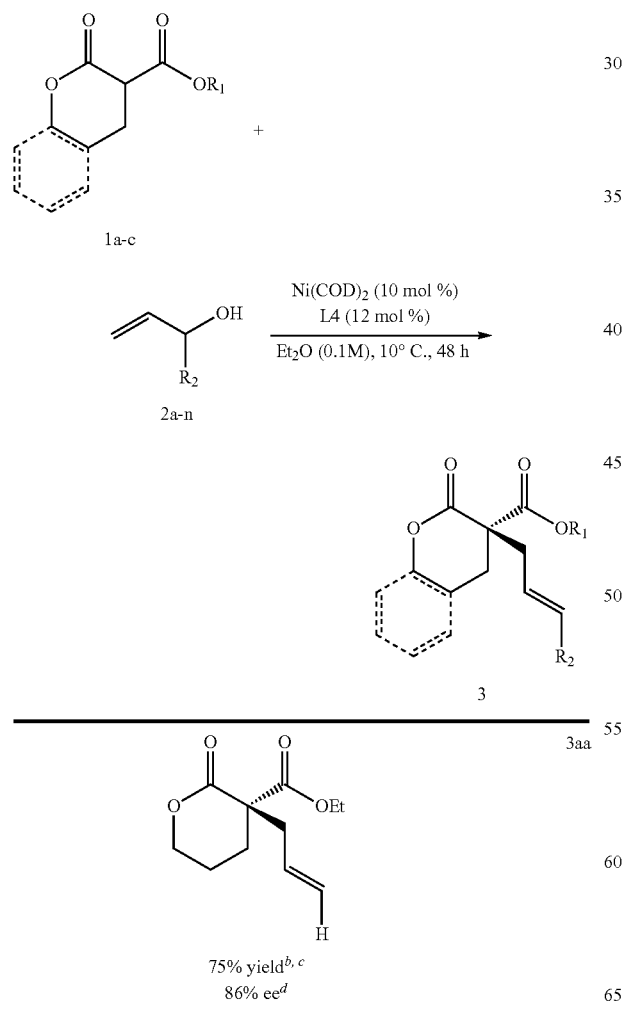

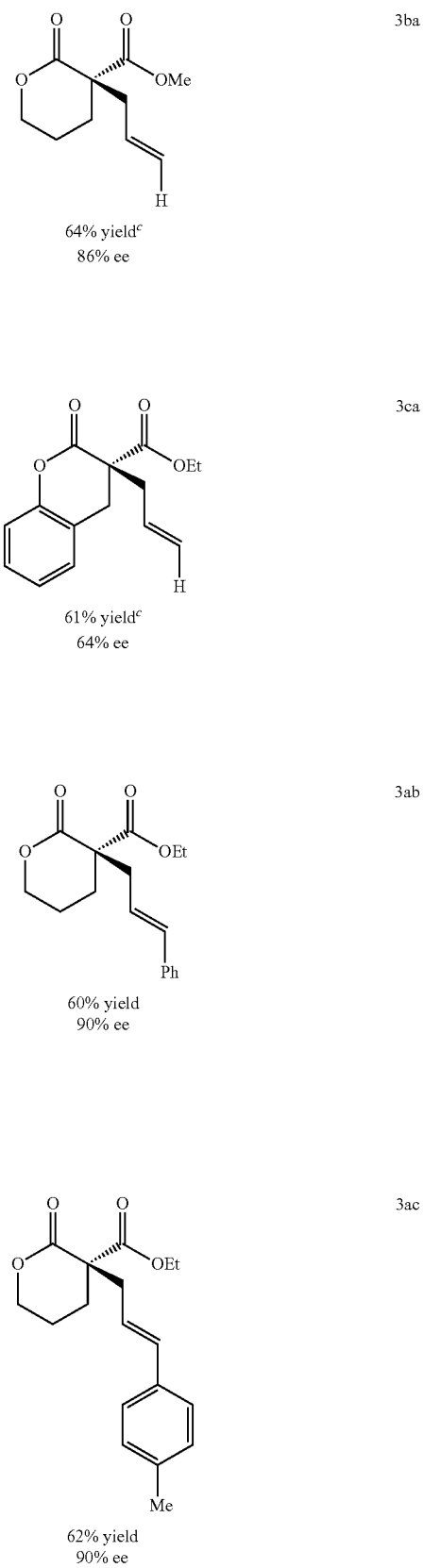

TABLE 2-continued
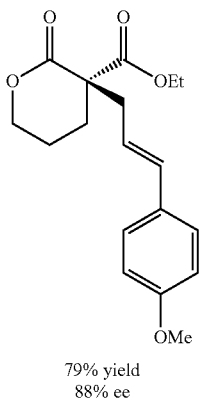 [SMILES: CCOC(=O)[C@]1(C/C=C/c2ccc(OC)cc2)CCCOC1=O]
3ad
79% yield
88% ee
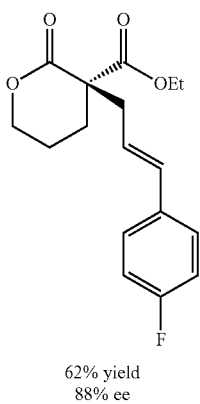 [SMILES: CCOC(=O)[C@]1(C/C=C/c2ccc(F)cc2)CCCOC1=O]
3ae
62% yield
88% ee
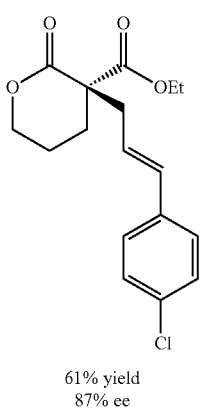 [SMILES: CCOC(=O)[C@]1(C/C=C/c2ccc(Cl)cc2)CCCOC1=O]
3af[e]
61% yield
87% ee
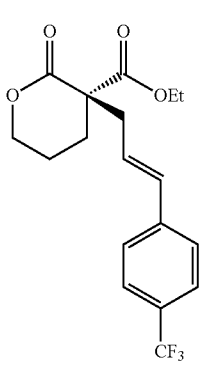
3ag
44% yield
86% ee
TABLE 2-continued
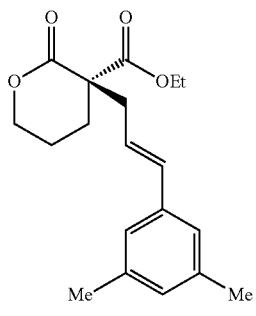
3ah
65% yield
88% ee
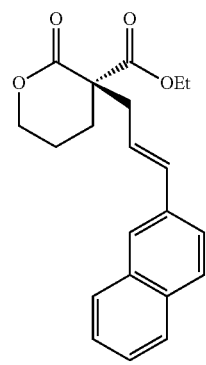
3ai
62% yield
88% ee
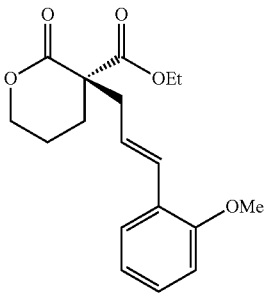
3aj
51% yield
90% ee
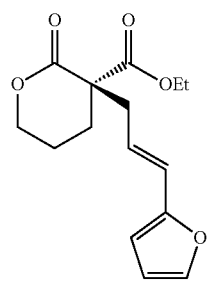
3ak
82% yield
88% ee

TABLE 2-continued

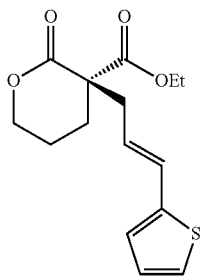

3al

68% yield
88% ee

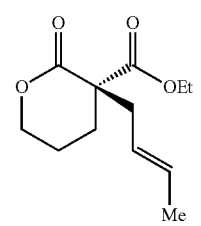

3am

57% yield
78% ee

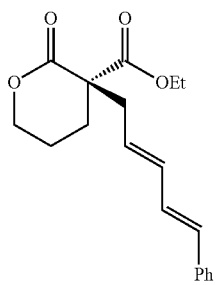

3an

91% yield
88% ee

[a]Reactions performed on 0.2 mmol.
[b]Yield of isolated product.
[c]Reaction performed at −10° C.
[d]Determined by chiral SFC analysis.
[e]Absolute configuration determined via single crystal x-ray analysis.

The transformation of nitrogen-containing lactam nucleophiles was also investigated. Under modified reaction conditions using the same chiral bisphosphine ligand L4, α-ester lactams 4a-4b furnish products 5aa-5ba in good yields and with even higher enantioselectivity as compared to their lactone counterparts (Table 3). Reaction of α-ethoxycarbonyl benzoyl-protected lactam 4a with branched cinnamyl alcohol affords linear product 5ab in 74% yield and % ee.

TABLE 3

α-acyl lactam prochiral nucleophiles.[a]

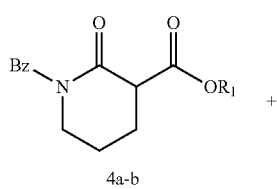

TABLE 3-continued

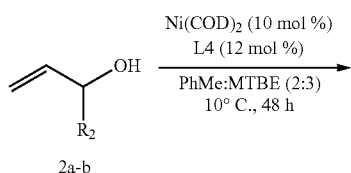

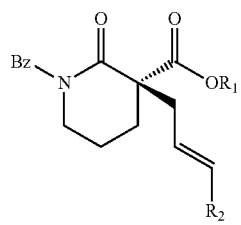

5

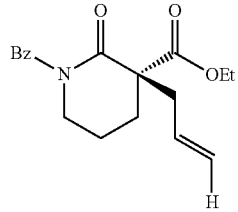

5aa

73% yield[b]
90% ee[c]

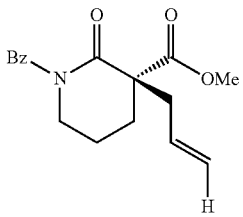

5ba

85% yield
90% ee

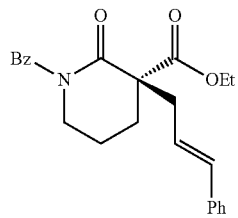

5ab

74% yield[d]
90% ee

[a]Reactions performed on 0.2 mmol.
[b]Yield of isolated product.
[c]Determined by chiral SFC analysis.
[d]Reaction performed at 30° C.

In order to gain mechanistic insights into this transformation, the results from reactions using linear and branched cinnamyl alcohols (Table 4) were compared. Only the linear product was detected, indicating that a nickel π-allyl is likely an intermediate in the catalytic cycle. The ability of this catalyst combination to access a single product from two electrophilic coupling partners highlights its flexibility in potential synthetic applications.

TABLE 4

Linear vs. branched cinnamyl alcohol.[a]

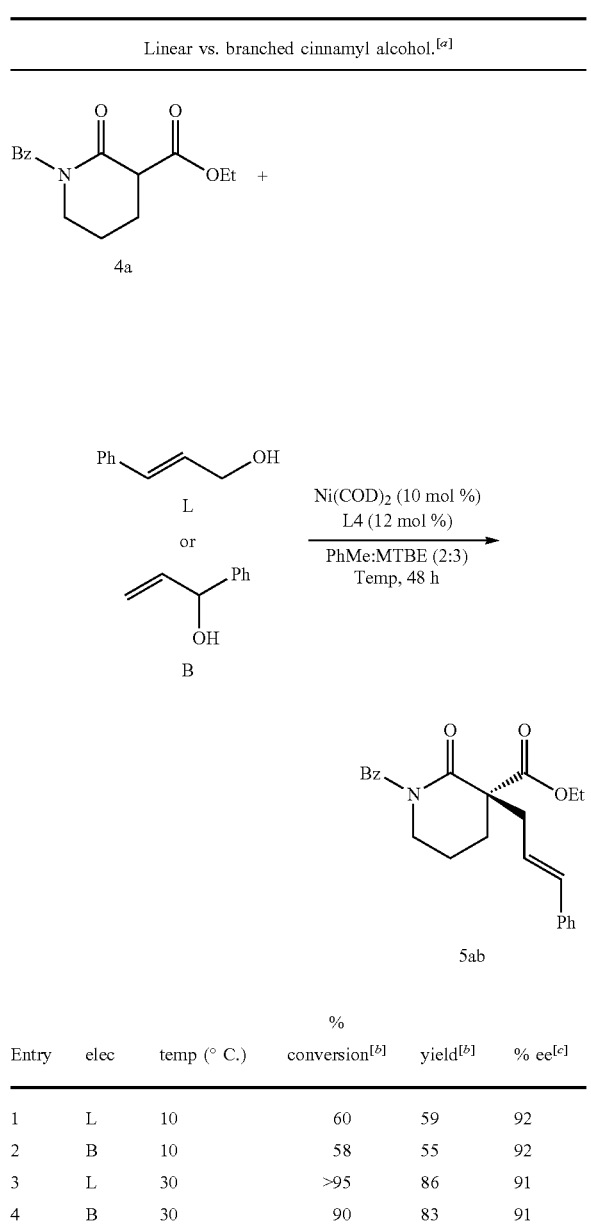

| Entry | elec | temp (° C.) | % conversion[b] | yield[b] | % ee[c] |
|---|---|---|---|---|---|
| 1 | L | 10 | 60 | 59 | 92 |
| 2 | B | 10 | 58 | 55 | 92 |
| 3 | L | 30 | >95 | 86 | 91 |
| 4 | B | 30 | 90 | 83 | 91 |

[a]Reactions performed on 0.1 mmol scale

[b]Yields determined by ¹H NMR of crude reaction mixture using benzyl ether as a standard.

[c]Determined by chiral SFC analysis of the isolated product.

To demonstrate the synthetic utility of the α-quaternary products, a number of product transformations on both α-quaternary lactone 3aa (Scheme 10) and lactam 5aa (Scheme 11) were performed. Selective reduction of the lactone functionality in 3aa provides diol 6 in 88% yield. Additionally, vinyl Grignard addition into lactone 3aa affords enone 7 in 67% yield with no erosion of enantioselectivity. These enantioenriched acyclic products 6 and 7 bearing a quaternary stereocenter are envisioned to be useful chiral building blocks as they contain multiple functional handles for further manipulations. For example, enantioenriched spirocycle 8 can be accessed via ring-closing metathesis followed by lactonization of enone 7.

Scheme 10. a) NaBH₄, CeCl₃·7H₂O, THF/MeOH, 0° C., 88% yield; b) Vinyl-magnesium bromide, THF, -78 °C., 67% yield, 86% ee; c) Grubbs' II (5 mol%), Toluene, 40° C.; DBU, MeCN, 23° C., 53% yield.

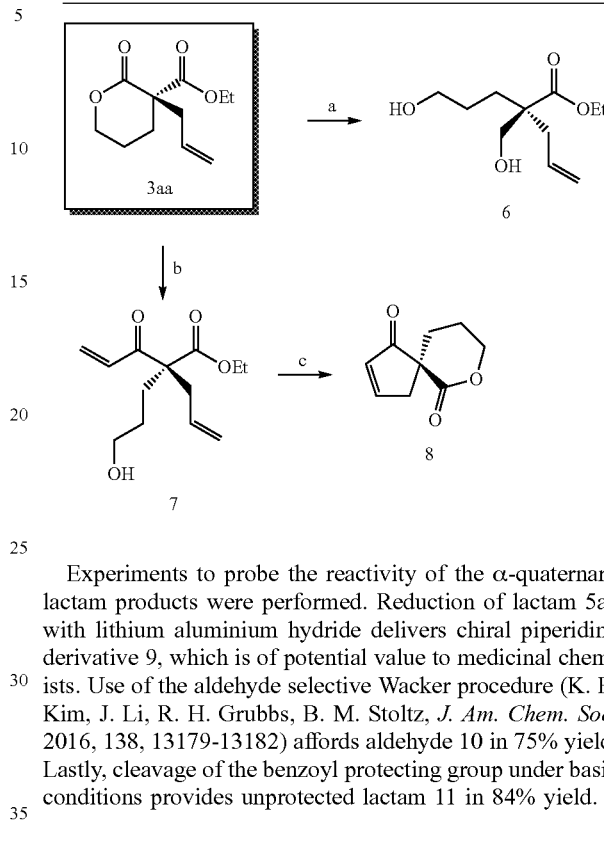

Experiments to probe the reactivity of the α-quaternary lactam products were performed. Reduction of lactam 5aa with lithium aluminium hydride delivers chiral piperidine derivative 9, which is of potential value to medicinal chemists. Use of the aldehyde selective Wacker procedure (K. E. Kim, J. Li, R. H. Grubbs, B. M. Stoltz, *J. Am. Chem. Soc.* 2016, 138, 13179-13182) affords aldehyde 10 in 75% yield. Lastly, cleavage of the benzoyl protecting group under basic conditions provides unprotected lactam 11 in 84% yield.

Scheme 11. a) LAH, Ether, 65° C., 80% yield; b) CuCl·H₂O (12 mol%), PdCl₂(PhCN)₂(12 mol %), AgNO₂(6 mol %), t-BuOH, Nitromethane under O₂, 75% yield; c) NaOEt, EtOH, 23° C., 84% yield.

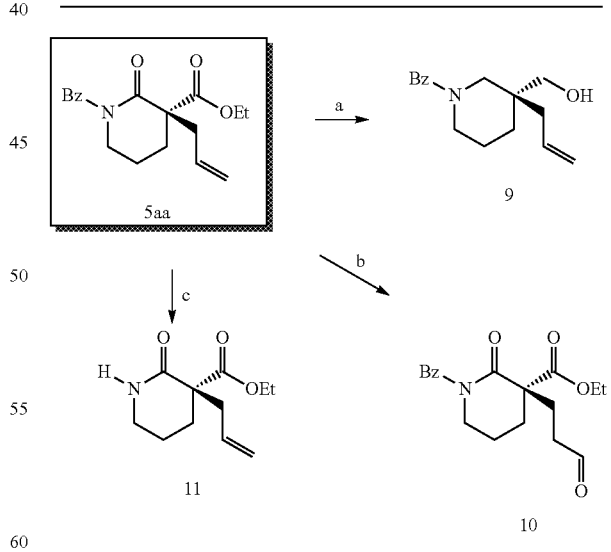

Materials and Methods

Unless otherwise stated, reactions were performed in flame-dried glassware under an argon or nitrogen atmosphere using dry, deoxygenated solvents. Solvents were dried by passage through an activated alumina column under argon. Reaction progress was monitored by thin-layer chromatography (TLC) or Agilent 1290 UHPLC-MS. TLC was performed using E. Merck silica gel 60 F254 precoated glass plates (0.25 mm) and visualized by UV fluorescence quenching, p-anisaldehyde, or $KMnO_4$ staining. Silicycle SiliaFlash® P60 Academic Silica gel (particle size 40-63 nm) was used for flash chromatography. $^1$H NMR spectra were recorded on Bruker 400 MHz or Varian Mercury 300 MHz spectrometers and are reported relative to residual $CHC_3$ (δ 7.26 ppm). $^{13}$C NMR spectra were recorded on Bruker 400 MHz spectrometer (101 MHz) and are reported relative to $CHC_3$ (δ 77.16 ppm). $^{19}$F NMR spectra were recorded on Varian Mercury 300 MHz spectrometer (282 MHz). Data for $^1$H NMR are reported as follows: chemical shift (δ ppm) (multiplicity, coupling constant (Hz), integration). Multiplicities are reported as follows: s=singlet, d=doublet, t=triplet, q=quartet, p=pentet, sept=septuplet, m=multiplet, br s=broad singlet, br d=broad doublet, app=apparent. Data for $^{13}$C NMR are reported in terms of chemical shifts (δ ppm). IR spectra were obtained using Perkin Elmer Spectrum BXII spectrometer or Nicolet 6700 FTIR spectrometer using thin films deposited on NaCl plates and reported in frequency of absorption ($cm^{-1}$). Optical rotations were measured with a Jasco P-2000 polarimeter operating on the sodium D-line (589 nm), using a 100 mm path-length cell and are reported as: $[\alpha]_D^T$ (concentration in 10 mg/1 mL, solvent). Analytical SFC was performed with a Mettler SFC supercritical $CO_2$ analytical chromatography system utilizing Chiralpak (AD-H, AS-H or IC) or Chiralcel (OD-H, OJ-H, or OB—H) columns (4.6 mm×25 cm) obtained from Daicel Chemical Industries, Ltd. High resolution mass spectra (HRMS) were obtained from Agilent 6200 Series TOF with an Agilent G1978A Multimode source in electrospray ionization (ESI+), atmospheric pressure chemical ionization (APCI+), or mixed ionization mode (MM: ESI-APCI+), or obtained from Caltech mass spectrometry laboratory. Low-temperature diffraction data (φ- and ω-scans) were collected on a Bruker AXS D8 VENTURE KAPPA diffractometer coupled to a PHOTON 100 CMOS detector with Cu $K_\alpha$ radiation (λ=1.54178 Å) from an IµS micro-source for the structure of compound P17471. The structure was solved by direct methods using SHELXS and refined against $F^2$ on all data by full-matrix least squares with SHELXL-2016 using established refinement techniques. All non-hydrogen atoms were refined anisotropically. All hydrogen atoms were included into the model at geometrically calculated positions and refined using a riding model. The isotropic displacement parameters of all hydrogen atoms were fixed to 1.2 times the U value of the atoms they are linked to (1.5 times for methyl groups).

Reagents were purchased from Sigma-Aldrich, Acros Organics, Strem, or Alfa Aesar and used as received unless otherwise stated.

List of Abbreviations ee—enantiomeric excess, SFC—supercritical fluid chromatography, TLC—thin-layer chromatography, IPA—isopropanol, MTBE—methyl tert-butyl ether, PE—petroleum ether, LHMDS—lithium bis(trimethylsilyl)amide, Bz—benzoyl, Ts—Tosyl, Boc—tert-butyloxycarbonyl Synthesis of Nucleophiles: Experimental Procedures and Spectroscopic Data General Procedure 1: α-Acylation of Lactones

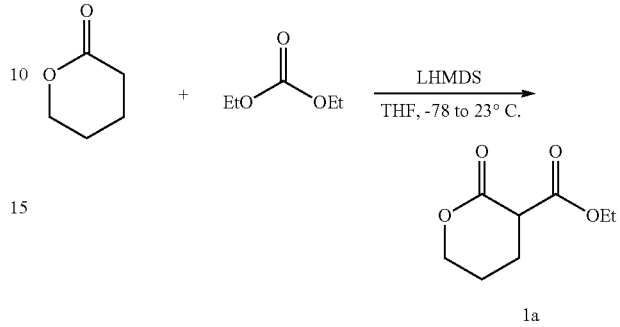

Ethyl 2-oxotetrahydro-2H-pyran-3-carboxylate (1a)

To a solution of LHMDS (3.43 g, 20.5 mmol, 2.05 equiv) in THF (20 mL) was added a mixture of delta-valerolactone (1.00 g, 10.0 mmol, 1.00 equiv) and diethyl carbonate (1.3 mL, 11.0 mmol, 1.10 equiv) at −78° C. After stirring at room temperature for 6 hours, the reaction was quenched with glacial acetic acid (5 mL), diluted with $Et_2O$ (20 mL), and stirred for 5 minutes. The insoluble white solid was filtered off and rinsed with more $Et_2O$. The filtrate was concentrated and purified by column chromatography (50% to 65% $Et_2O$ in PET) to afford 1a as a colorless oil (1.20 g, 70% yield); $^1$H NMR (300 MHz, $CDCl_3$) δ 4.46-4.31 (m, 2H), 4.25 (qd, J=7.1, 1.7 Hz, 2H), 3.56 (dd, J=8.3, 7.5 Hz, 1H), 2.38-2.08 (m, 2H), 2.08-1.80 (m, 2H), 1.30 (t, J=7.1 Hz, 3H). All characterization data match those reported.

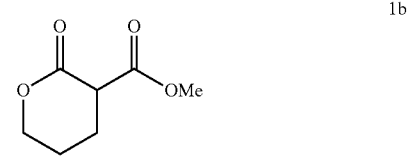 [SMILES: COC(=O)C1CCCOC1=O]

Methyl 2-oxotetrahydro-2H-pyran-3-carboxylate (1b)

Compound 1b was prepared from dimethyl carbonate using general procedure 1 (1.38 g, 87% yield); $^1$H NMR (300 MHz, $CDCl_3$) δ 4.46-4.32 (m, 2H), 3.80 (s, 3H), 3.58 (dd, J=8.4, 7.5 Hz, 1H), 2.38-2.06 (m, 2H), 2.02-1.81 (m, 2H). All characterization data match those reported.

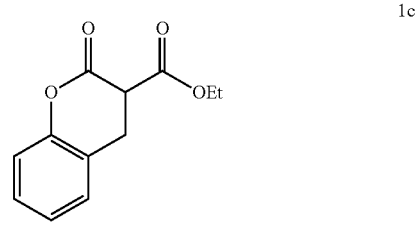 [SMILES: CCOC(=O)C1Cc2ccccc2OC1=O]

Ethyl 2-oxochromane-3-carboxylate (1c)

Compound 1c was prepared from dihydrocoumarin and diethyl carbonate using general procedure 1 (0.28 g, 25% yield); $^1$H NMR (300 MHz, CDCl$_3$) δ 7.33-7.18 (m, 2H), 7.17-6.99 (m, 2H), 4.34-4.08 (m, 2H), 3.76 (dd, J=8.5, 6.1 Hz, 1H), 3.42 (dd, J=16.0, 8.5 Hz, 1H), 3.18 (dd, J=16.0, 6.0 Hz, 1H), 1.21 (t, J=7.1 Hz, 3H). All characterization data match those reported.

General Procedure 2: α-Acylation of Lactams

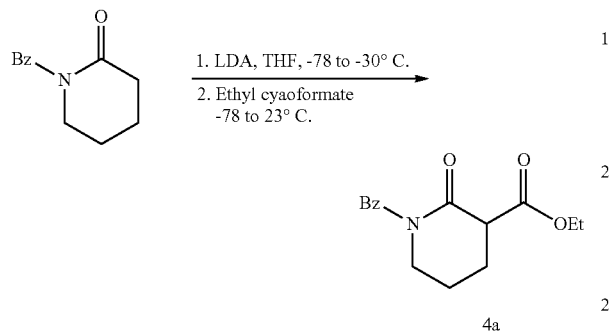

Ethyl 1-benzoyl-2-oxopiperidine-3-carboxylate (4a)

To a solution of diisopropylamine (1.7 mL, 12 mmol, 1.2 equiv) in THF (65 mL) at 0° C., n-BuLi (4.6 mL, 11 mmol, 2.4 M in hexanes, 1.1 equiv) was added dropwise over 10 minutes. After stirring for 30 min at 0° C., the solution was cooled to −78° C. and a solution of benzoyl-protected lactam (2.0 g, 12 mmol, 1.2 equiv) in THF (17 mL) was then added over 5 minutes. The reaction mixture was stirred at −78° C. for 2 hours and warmed to −30° C. for 1 hour. Ethyl cyanoformate (1.1 mL, 11 mmol, 1.1 equiv) was then added at −78° C. The reaction was allowed to slowly warm to room temperature overnight. Upon complete consumption of starting material by TLC, the reaction was quenched with saturated NH$_4$Cl. The aqueous layer was extracted with EtOAc (50 mL×4). The combined organic phases were washed with brine (50 mL), dried over Na$_2$SO$_4$, filtered, and concentrated under vacuum. The crude residue was purified by column chromatography (30% EtOAc in hexanes) to provide product 4a as a white amorphous solid (1.47 g, 53% yield); $^1$H NMR (400 MHz, CDCl$_3$) δ 7.73-7.66 (m, 2H), 7.52-7.44 (m, 1H), 7.43-7.34 (m, 2H), 4.25 (q, J=7.1 Hz, 2H), 3.89-3.75 (m, 2H), 3.58-3.50 (m, 1H), 2.40-2.27 (m, 1H), 2.22-2.00 (m, 2H), 2.00-1.89 (m, 1H), 1.32 (t, J=7.1 Hz, 3H); $^{13}$C NMR (101 MHz. CDCl$_3$) δ 174.7, 170.0, 169.6, 135.6, 132.0, 128.3, 128.2, 62.0, 51.2, 46.4, 25.6, 20.7, 14.2; IR (Neat Film, NaCl) 3062, 2980, 1734, 1701, 1683, 1476, 1449, 1392, 1285, 1258, 1185, 1152, 1113, 1026, 999, 730, 670, 638 cm$^{-1}$; HRMS (MM) m/z calc'd for C$_{15}$H$_{18}$NO$_4$ [M+H]$^+$: 276.1230, found 276.1237.

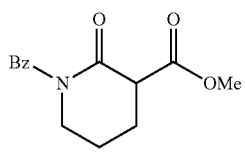

4b

Methyl 1-benzoyl-2-oxopiperidine-3-carboxylate (4b)

Compound 4b was prepared from Bz-protected lactam and methyl cyanoformate using general procedure 2 and purified by column chromatography (40% EtOAc in hexanes) to provide a colorless amorphous solid (0.33 g, 51% yield); $^1$H NMR (400 MHz, CDCl$_3$) δ 7.73-7.65 (m, 2H), 7.48 (m, 1H), 7.43-7.36 (m, 2H), 3.86-3.80 (m, 2H), 3.79 (s, 3H), 3.59 (t, J=6.4 Hz, 1H), 2.39-2.27 (m, 1H), 2.23-2.03 (m, 2H), 2.02-1.89 (m, 1H); 3C NMR (101 MHz, CDCl$_3$) δ 174.7, 170.5, 169.6, 135.6, 132.0, 128.3, 128.3, 52.9, 51.1, 46.4, 25.6, 20.9; IR (Neat Film, NaCl) 2953, 1738, 1681, 1600, 1449, 1392, 1284, 1258, 1200, 1151, 1115, 1065, 973, 954, 857, 796, 731, 701, 639; HRMS (MM) m/z calc'd for C$_{14}$H$_{16}$NO$_4$ [M+H]$^+$: 262.1074, found 262.1066.

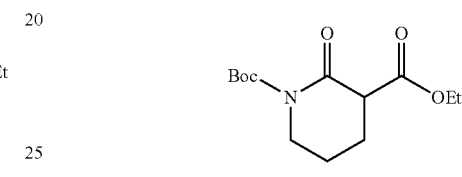

1-(tert-butyl) 3-ethyl 2-oxopiperidine-1,3-dicarboxylate

This compound was prepared from Boc-protected lactam using general procedure 2 and purified by column chromatography (20% EtOAc in hexanes) to provide a colorless oil (0.47 g, 70% yield); $^1$H NMR (400 MHz, CDCl$_3$) δ 4.30-4.13 (m, 2H), 3.75-3.62 (m, 2H), 3.49 (dd, J=8.7, 6.8 Hz, 1H), 2.24-2.02 (m, 2H), 1.96 (dtt, J=14.1, 6.6, 5.2 Hz, 1H), 1.81 (dddt, J=14.1, 8.8, 7.5, 5.3 Hz, 1H), 1.52 (s, 9H), 1.29 (t, J=7.1 Hz, 3H); $^{13}$C NMR (101 MHz, CDCl$_3$) δ 170.1, 167.6, 152.8, 83.6, 61.7, 51.6, 45.9, 28.1, 24.4, 21.2, 14.2; IR (Neat Film, NaCl) 2980, 2939, 1772, 1717, 1478, 1458, 1393, 1369, 1297, 1252, 1146, 1115, 1096, 1056, 1029, 937, 852, 778, 748, 642; HRMS (MM) m/z calc'd for C$_{13}$H$_{21}$NO$_5$Na [M+Na]$^+$: 294.1312, found 294.1315.

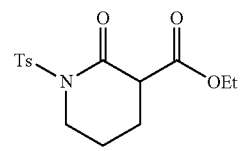

Ethyl 2-oxo-1-tosylpiperidine-3-carboxylate

This compound was prepared from tosyl-protected lactam using general procedure 1 and purified by column chromatography (35% to 40% EtOAc in hexanes) to provide a colorless oil (0.32 g, 41% yield); 1H NMR (400 MHz, CDCl$_3$) δ 7.90 (d, J=8.4 Hz, 2H), 7.31 (d, J=7.9 Hz, 2H), 4.12 (qd, J=7.1, 1.2 Hz, 2H), 4.03-3.84 (m, 2H), 3.41 (dd, J=7.5, 6.3 Hz, 1H), 2.43 (s, 3H), 2.19-1.97 (m, 3H), 1.96-1.82 (m, 1H), 1.18 (t, J=7.1 Hz, 3H); $^{13}$C NMR (101 MHz, CDCl$_3$) δ 169.3, 166.6, 145.1, 135.7, 129.5, 128.9, 61.9, 50.9, 46.6, 24.3, 21.8, 21.5, 14.1; IR (Neat Film, NaCl) 2980, 1737, 1694, 1456, 1353, 1289, 1169, 1089, 1036, 1008, 827, 815, 706, 670, 653; HRMS (MM) m/z calc'd for $C_{15}H_{20}NO_5S$ [M+H]+: 326.1057, found 326.1066.

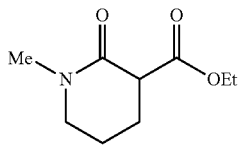 [SMILES: CCOC(=O)C1CCCN(C)C1=O]

Ethyl 1-methyl-2-oxopiperidine-3-carboxylate

This compound was prepared from methyl-protected lactam using A previously reported procedure. $^1$H NMR (300 MHz, CDCl$_3$) δ 4.31-4.08 (m, 2H), 3.44-3.20 (m, 3H), 2.96 (s, 3H), 2.24-1.89 (m, 3H), 1.89-1.69 (m, 1H), 1.28 (t, J=7.1 Hz, 3H). All characterization data match those reported.

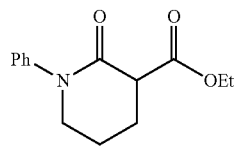

Ethyl 2-oxo-1-phenylpiperidine-3-carboxylate

This compound was prepared from phenyl-protected lactam using general procedure 2 and purified by column chromatography (40% EtOAc in hexanes) to provide a pale yellow solid (0.53 g, 42% yield); $^1$H NMR (400 MHz, CDCl$_3$) 7.42-7.35 (m, 2H), 7.29-7.22 (m, 3H), 4.31-4.15 (m, 2H), 3.76-3.61 (m, 2H), 3.57 (dd, J=7.8, 6.4 Hz, 1H), 2.35-2.04 (m, 3H), 2.00-1.88 (m, 1H), 1.30 (t, J=7.1 Hz, 3H); $^{13}$C NMR (101 MHz, CDCl$_3$) δ 171.1, 166.2, 142.9, 129.3, 127.0, 126.1, 61.5, 51.4, 49.7, 25.3, 21.5, 14.3; IR (Neat Film, NaCl) 2943, 1734, 1654, 1595, 1494, 1462, 1427, 1371, 1353, 1308, 1259, 1197, 1171, 1036, 763, 697, 659; HRMS (MM) m/z calc'd for $C_{14}H_{18}NO_3$ [M+H]+: 248.1281, found 248.1278.

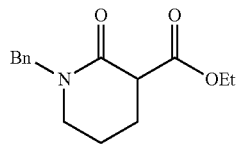 [SMILES: CCOC(=O)C1CCCN(c2ccccc2)C1=O]

Ethyl 1-benzyl-2-oxopiperidine-3-carboxylate

This compound was prepared from benzyl-protected lactam using general procedure 2 (0.32 g, 56% yield); $^1$H NMR (300 MHz, CDCl$_3$) δ 7.37-7.23 (m, 5H), 4.73 (d, J=14.7 Hz, 1H), 4.51 (d, J=14.7 Hz, 1H), 4.24 (qd, J=7.1, 4.0 Hz, 2H), 3.59-3.43 (m, 1H), 3.36-3.12 (m, 2H), 2.29-1.97 (m, 2H), 1.97-1.83 (m, 1H), 1.82-1.64 (m, 1H), 1.31 (t, J=7.2 Hz, 3H). All characterization data match those reported.

Nickel-Catalyzed Asymmetric Allylic Alkylation Reactions: General Procedures
Please note that the absolute configuration was determined only for compound 3af via x-ray crystallographic analysis. The absolute configuration for all other products has been inferred by analogy. For respective HPLC and SFC conditions, please refer to Table 7.

General Procedure 3: Nickel-Catalyzed Asymmetric Allylic Alkylation of Lactones

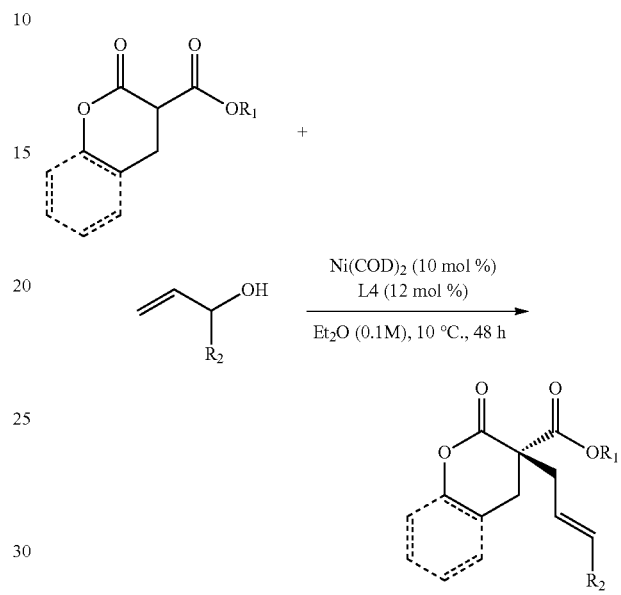

In a nitrogen-filled glovebox, to an oven-dried 4-mL vial equipped with a stir bar was added (R)—P-Phos ligand L4 (15.5 mg, 0.024 mmol, 12 mol %) and Ni(COD)$_2$ (5.5 mg, 0.02 mmol, 10 mol %) in Et$_2$O (1.2 mL). The vial was then capped with a PTFE-lined septum cap and stirred at room temperature. After 30 minutes, the catalyst mixture was cooled to 10° C. Precooled nucleophile (0.2 mmol, 1 equiv) in Et$_2$O (0.4 mL) and electrophile (0.2 mmol, 1 equiv) in Et$_2$O (0.4 mL) at 10° C. were prepared and then added to the catalyst mixture at 10° C. The vial was sealed with a PTFE-lined septum cap and stirred at 10° C. After 48 h, the vial was removed from the glovebox. The crude reaction mixture was filtered through a silica plug with Et$_2$O, concentrated under vacuum, and purified by silica gel flash chromatography to furnish the product.

General Procedure 4: Nickel-Catalyzed Asymmetric Allylic Alkylation of Lactams

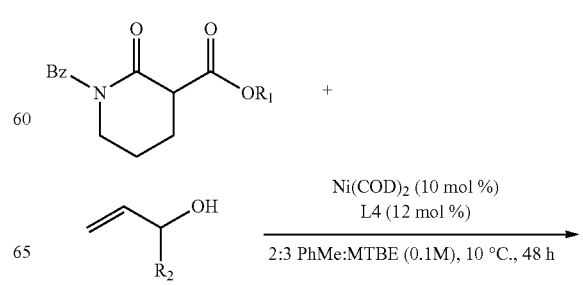

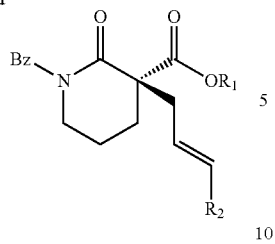

In a nitrogen-filled glovebox, to an oven-dried 4-mL vial equipped with a stir bar was added (R)—P-Phos ligand L4 (15.5 mg, 0.024 mmol, 12 mol %) and Ni(COD)$_2$ (5.5 mg, 0.02 mmol, 10 mol %) in MTBE (1.2 mL). The vial was then capped with a PTFE-lined septum cap and stirred at room temperature. After 30 minutes, the catalyst mixture was cooled to 10° C. Precooled nucleophile (0.2 mmol, 1 equiv) in toluene (0.4 mL) and electrophile (0.2 mmol, 1 equiv) in toluene (0.4 mL) at 10° C. were prepared and then added to the catalyst mixture at 10° C. The vial was sealed with a PTFE-lined septum cap and stirred at 10° C. After 48 h, the vial was removed from the glovebox. The crude reaction mixture was filtered through a silica plug with Et$_2$O, concentrated under vacuum, and purified by silica gel flash chromatography to furnish the product.

Additional Ligand Screen Results

TABLE 5

Additional Ligand Screen

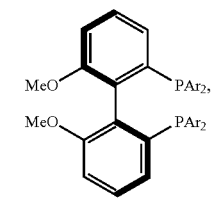

| Entry | Ligand | ee (%) |
|---|---|---|
| 1 | L5 | 14 |
| 2 | L6 | 20 |
| 3 | L7 | — |
| 4 | L8 | −60 |
| 5 | L9 | 57 |
| 6 | L10 | 67 |
| 7 | L11 | −63 |
| 8 | L12 | — |
| 9 | L13 | 8 |
| 10 | L14 | 19 |
| 11 | L15 | — |
| 12 | L16 | 11 |
| 13 | L17 | 24 |
| 14 | L18 | — |
| 15 | L19 | 12 |
| 16 | L20 | — |
| 17 | L21 | — |
| 18 | L22 | 17 |
| 19 | L23 | 0 |
| 20 | L24 | −34 |
| 21 | L25 | — |
| 22 | L26 | −6 |
| 23 | L27 | 3 |
| 24 | L28 | — |
| 25 | L29 | 31 |
| 26 | L30 | 9 |
| 27 | L31 | −15 |
| 28 | L32 | −22 |
| 29 | L33 | — |
| 30 | L34 | −73 |
| 31 | L35 | — |
| 32 | L36 | — |
| 33 | L37 | — |
| 34 | L38 | — |
| 35 | L39 | — |
| 36 | L40 | −44 |

Ligand List:

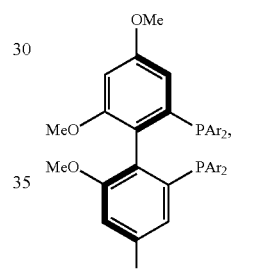

L5: Ar = 3,5-t-Bu$_2$C$_5$H$_3$
L6: Ar = 3,5-t-Bu$_2$-4-MeOC$_5$H$_2$

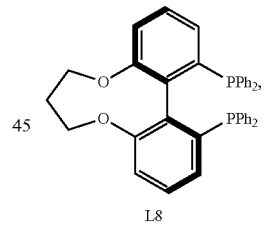

L7: Ar = 3,5-(CF$_3$)$_2$C$_5$H$_3$

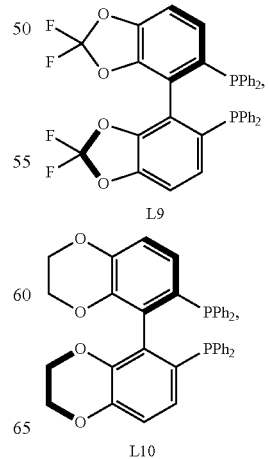

TABLE 5-continued
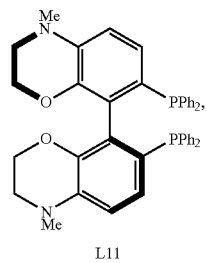
L11
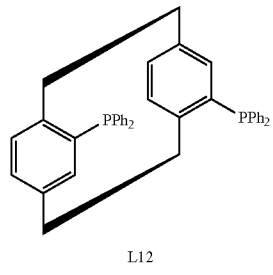
L12
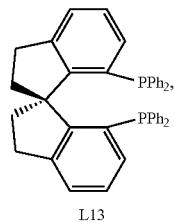
L13
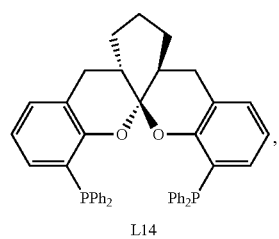
L14
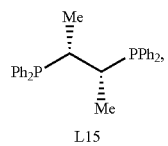
L15
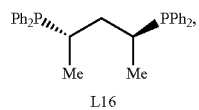
L16
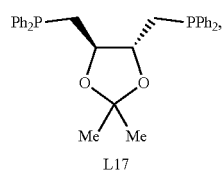
L17
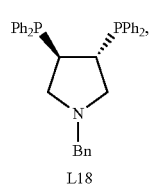
L18
TABLE 5-continued
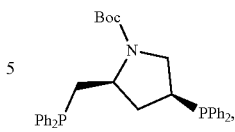
L19
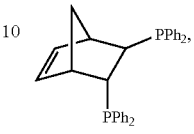
L20
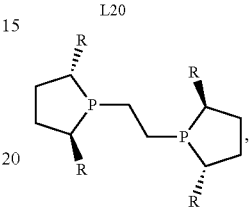
L21: R = Me
L22: R = i-Pr
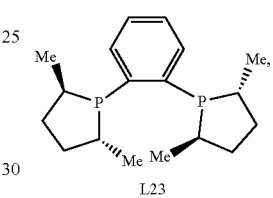
L23
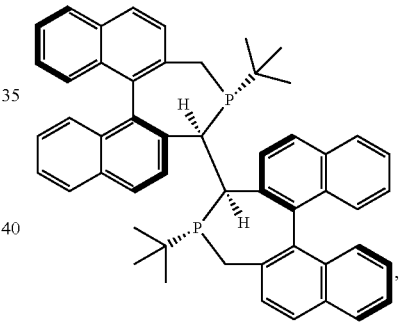
L24
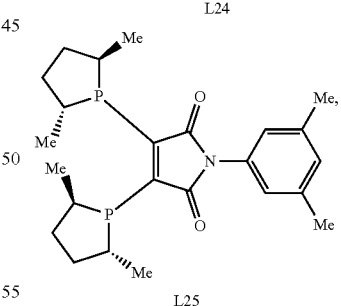
L25
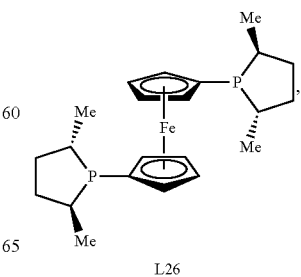
L26

TABLE 5-continued
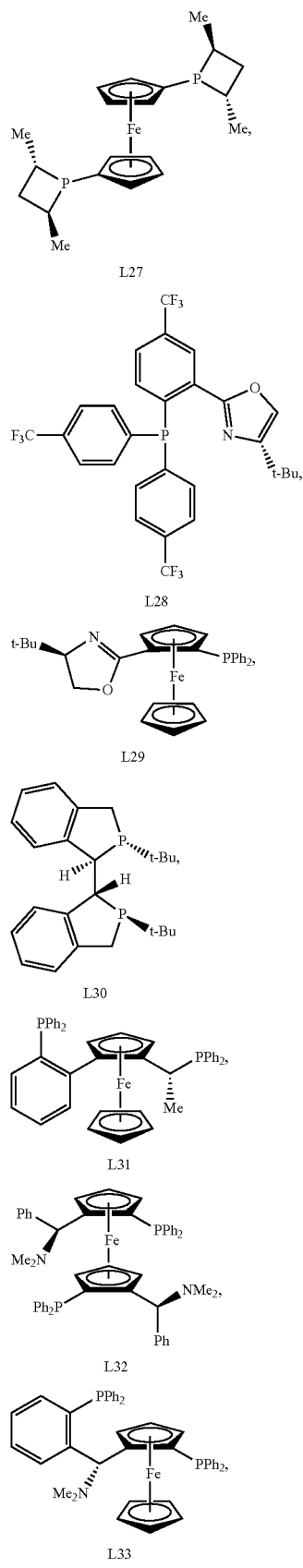
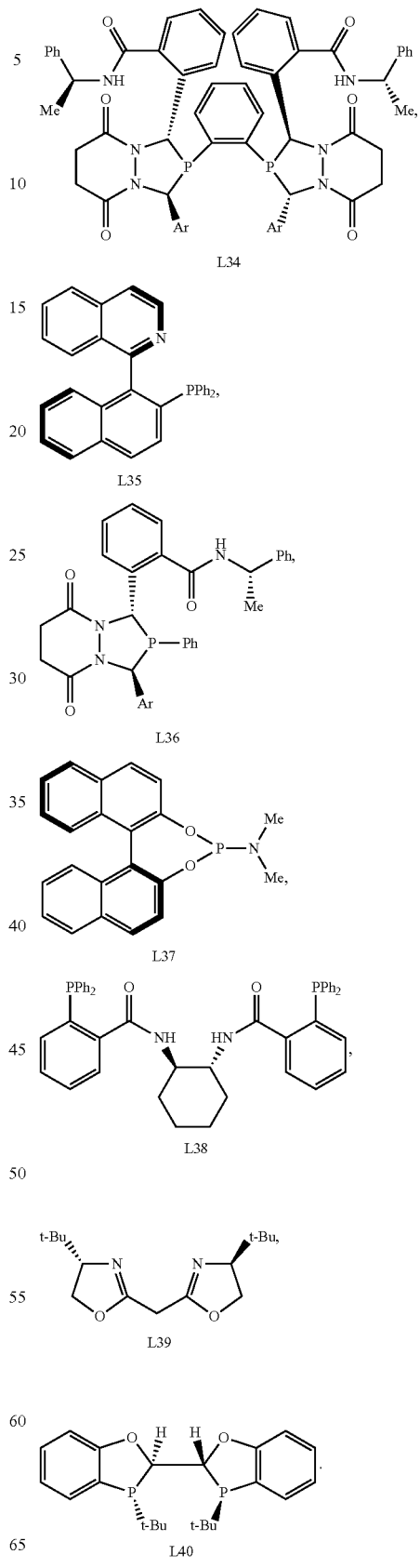

Solvent Effects in Nickel-Catalyzed Asymmetric Allylic Alkylation of Lactones

TABLE 6

Solvent Effects[a]

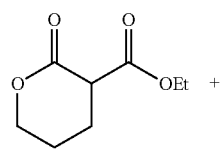

| Ligand | Solvent (% ee)[b] | | | | |
|---|---|---|---|---|---|
| | Et₂O | MTBE | THF | Dioxane | Toluene |
| L1: (R)-BINAP | 62% ee | 65% ee | 41% ee | 18% ee | 45% ee |
| L2: (R)-H₈-BINAP | 74% ee | 72% ee | 60% ee | 22% ee | 46% ee |
| L3: (R)-Segphos | 72% ee | 70% ee | 45% ee | 28% ee | 46% ee |
| L4: (R)-P-phos | 74% ee | 67% ee | 52% ee | 25% ee | 51% ee |

[a]Conditions: lactone (0.05 mmol), alcohol (0.05 mmol), Ni(COD)₂ (10 mol %), ligand (12 mol %) for 19 h.
[b]Determined by chiral SFC analysis.

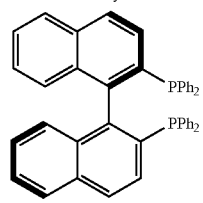

L1: (R)-BINAP

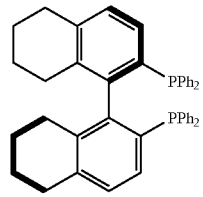

L2: (R)-H₈-BINAP

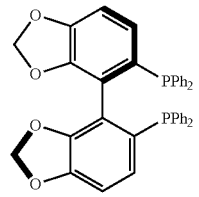

L3: (R)-Segphos

TABLE 6-continued

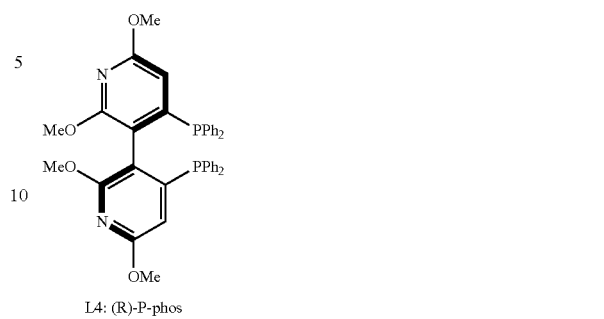

L4: (R)-P-phos

Optimization of Reaction Parameters for Lactams

TABLE 7

Optimization of reaction parameters for lactam 4a[a]

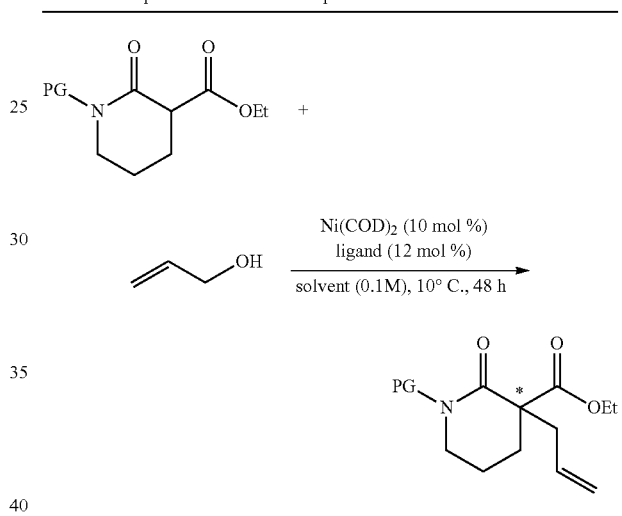

| entry | PG | ligand | solvent | yield [%][b] | ee [%][c] |
|---|---|---|---|---|---|
| 1 | Bz | L2 | PhMe:MTBE (2:3) | 95 | 77 |
| 2 | Bz | L3 | PhMe:MTBE (2:3) | >95 | 88 |
| 3 | Bz | L4 | PhMe:MTBE (2:3) | 79 | 90 |
| 4[d] | Bz | L4 | PhMe:MTBE (2:3) | 28 | 88 |
| 5 | Bz | L4 | PhMe:Et₂O (2:3) | 70 | 88 |
| 6 | Bz | L4 | PhMe | 51 | 88 |
| 7 | Bz | L4 | THF | 15 | 76 |
| 8[e] | Bz | L4 | PhMe:MTBE (2:3) | >95 | 88 |

[a]Conditions: lactam (0.1 mmol), alcohol (0.1 mmol), Ni(COD)₂ (10 mol %), ligand (12 mol %) for 48 h.
[b]Yields determined by ¹H NMR of crude reaction mixture using trimethoxybenzene as a standard.
[c]Determined by chiral SFC analysis
[d]5 mol % Ni(COD)₂ and 6 mol % L4 were used.
[e]Reaction performed at 23° C.?

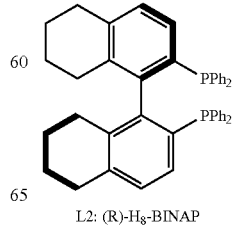

L2: (R)-H₈-BINAP

TABLE 7-continued

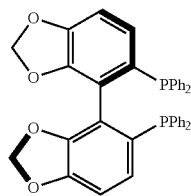

L3: (R)-Segphos

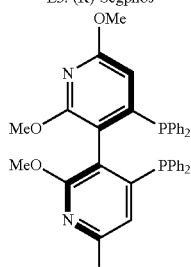

L4: (R)-P-phos

Spectroscopic Data for Products from Catalytic Reactions

3aa

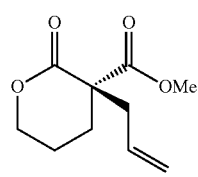

Ethyl (R)-3-allyl-2-oxotetrahydro-2H-pyran-3-carboxylate (3aa)

Product 3aa was prepared using general procedure 3 at −10° C. and purified by column chromatography (15% EtOAc in hexanes) to provide a colorless oil (31.8 mg, 75% yield); 86% ee, $[\alpha]_D^{25}$+3.84 (c 0.99, CHCl$_3$); $^1$H NMR (400 MHz, CDCl$_3$) δ $^1$H NMR (400 MHz, CDCl$_3$) δ 5.84-5.69 (m, 1H), 5.19-5.08 (m, 2H), 4.34-4.23 (m, 2H), 4.21 (q, J=7.1 Hz, 2H), 2.73 (ddt, J=13.8, 6.8, 1.2 Hz, 1H), 2.59 (ddt, J=13.9, 7.9, 1.0 Hz, 1H), 2.38-2.25 (m, 1H), 2.05-1.88 (m, 1H), 1.92-1.79 (m, 2H), 1.27 (t, J=7.1 Hz, 3H); $^{13}$C NMR (101 MHz, CDCl$_3$) δ 171.2, 170.0, 132.6, 119.9, 69.0, 62.2, 54.0, 40.8, 28.0, 20.6, 14.2; IR (Neat Film, NaCl) 2981, 1732, 1457, 1399, 1367, 1348, 1244, 1200, 1162, 1108, 1026, 974, 925, 857, 640 cm$^{-1}$; HRMS (MM) m/z calc'd for C$_{11}$H$_{17}$O$_4$ [M+H]$^+$: 213.1121, found 213.1120; SFC Conditions: 25% IPA, 2.5 mL/min, Chiralpak IC column, λ=210 nm, t$_R$ (min): major=2.66, minor=3.29.

3ba

Methyl (R)-3-allyl-2-oxotetrahydro-2H-pyran-3-carboxylate (3ba)

Product 3ba was prepared using general procedure 3 at −10° C. and purified by column chromatography (30% EtOAc in hexanes) to provide a colorless oil (25.5 mg, 64% yield); 86% ee, $[\alpha]_D^{25}$+5.071 (c 0.896, CHCl$_3$); $^1$H NMR (400 MHz, CDCl$_3$) δ 5.85-5.66 (m, 1H), 5.20-5.10 (m, 2H), 4.33-4.26 (m, 2H), 3.76 (s, 3H), 2.75 (ddt, J=13.8, 6.8, 1.3 Hz, 1H), 2.61 (ddt, J=13.8, 7.8, 1.0 Hz, 1H), 2.39-2.26 (m, 1H), 2.03-1.77 (m, 3H); $^{13}$C NMR (101 MHz, CDCl$_3$) δ 171.8, 169.9, 132.5, 120.1, 69.2, 54.1, 53.2, 40.9, 28.1, 20.6; IR (Neat Film, NaCl) 3079, 2955, 2920, 1733, 1640, 1480, 1436, 1401, 1349, 1321, 1277, 1247, 1204, 1164, 1122, 1108, 1076, 1000, 978, 126, 844, 716, 659, 640; HRMS (MM) m/z calc'd for C$_{10}$H$_{15}$O$_4$ [M+H]$^+$: 199.0965, found 199.0970; SFC Conditions 20% IPA, 2.5 mL/min, Chiralpak IC column λ=210 nm, t$_R$ (min): major=3.35, minor=3.99.

3ca

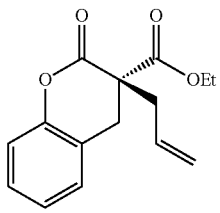

Ethyl (S)-3-allyl-2-oxochromane-3-carboxylate (3ca)

Product 3ca was prepared using general procedure 3 at −10° C. and purified by column chromatography (5% EtOAc in hexanes) to provide a colorless oil (31.9 mg, 61% yield); 64% ee, $[\alpha]_D^{25}$−30.75 (c 0.92, CHCl$_3$); $^1$H NMR (400 MHz, CDCl$_3$) δ 7.33-7.13 (m, 2H), 7.13-7.00 (m, 2H), 5.91 (ddt, J=16.6, 10.6, 7.3 Hz, 1H), 5.23-5.12 (m, 2H), 4.05 (qq, J=10.8, 7.1 Hz, 2H), 3.26 (d, 15.9 Hz, 1H), 3.04 (d, J=15.9 Hz, 1H), 2.84-2.67 (m, 2H), 1.02 (t, J=7.1 Hz, 3H); $^{13}$C NMR (101 MHz, CDCl$_3$) δ 169.5, 167.2, 151.2, 132.1, 128.7, 128.5, 124.8, 121.4, 120.4, 116.5, 62.2, 53.3, 38.6, 32.5, 14.0; IR (Neat Film, NaCl) 3079, 2982, 2936, 1774, 1738, 1653, 1640, 1590, 1541, 1490, 1460, 1344, 1232, 1190, 1145, 1096, 1020, 921, 858, 759, 658; HRMS (MM) m/z calc'd for C$_{15}$H$_{17}$O$_4$ [M+H]$^+$: 261.1121, found 261.1123; SFC Conditions: 5% IPA, 2.5 mL/min, Chiralcel OB—H column, λ=210 nm, t$_R$ (min): minor=2.22, major=2.64.

3ab

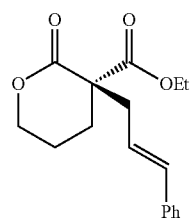

Ethyl (R)-3-cinnamyl-2-oxotetrahydro-2H-pyran-3-carboxylate (3ab)

Product 3ab was prepared using general procedure 3 and purified by column chromatography (15% EtOAc in hexanes) to provide a colorless oil (34.4 mg, 60% yield); 90% ee, $[\alpha]_D^{25}$-12.15 (c 0.64. CHCl$_3$); $^1$H NMR (400 MHz, CDCl$_3$) δ 7.38-7.25 (m, 4H), 7.27-7.17 (m, 1H), 6.47 (dt, J=16.0, 1.4 Hz, 1H), 6.19 (ddd, J=15.8, 8.0, 7.0 Hz, 1H), 4.35-4.17 (m, 4H), 2.91 (ddd, J=13.8, 7.0, 1.4 Hz, 1H), 2.74 (ddd, J=13.8, 8.0, 1.2 Hz, 1H), 2.45-2.31 (m, 1H), 2.11-1.77 (m, 3H), 1.27 (t, J=7.1 Hz, 3H); $^{13}$C NMR (101 MHz, CDCl$_3$) δ 171.2, 170.1, 136.9, 134.8, 128.7, 127.7, 126.4, 124.1, 69.1, 62.3, 54.4, 40.1, 28.1, 20.6, 14.2; IR (Neat Film, NaCl) 2980, 2342, 1955, 1733, 1577, 1449, 1399, 1367, 1243, 1198, 1164, 1026, 971, 910, 858, 746, 695, 642 cm$^{-1}$; HRMS (MM) m/z calc'd for C$_{17}$H$_{21}$O$_4$ [M+H]$^+$: 289.1430, found 289.1434; SFC Conditions: 10% IPA, 2.5 mL/min, Chiralpak AD-H column, λ=254 nm, $t_R$ (min): major=5.49, minor=6.31.

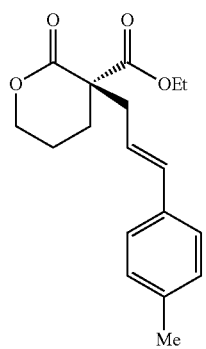

3ac

Ethyl (R,E)-2-oxo-3-(3-(p-tolyl)allyl)tetrahydro-2H-pyran-3-carboxylate (3ac)

Product 3ac was prepared using general procedure 3 and purified by column chromatography (15% EtOAc in hexanes) to provide a white amorphous solid (37.5 mg, 62% yield); 90% ee, $[\alpha]_D^{25}$-14.42 (c 0.95, CHCl$_3$); $^1$H NMR (400 MHz, CDCl$_3$) δ 7.24 (d, J=8.1 Hz, 2H), 7.15-6.98 (m, 2H), 6.51-6.33 (m, 1H), 6.13 (ddd, J=15.8, 8.1, 7.0 Hz, 1H), 4.31-4.26 (m, 2H), 4.23 (q, J=7.1 Hz, 2H), 2.90 (ddd, J=13.8, 7.0, 1.4 Hz, 1H), 2.72 (ddd, J=13.8, 8.1, 1.2 Hz, 1H), 2.41-2.25 (m, 4H), 2.02-1.78 (m, 3H), 1.27 (t, J=7.1 Hz, 3H); $^{13}$C NMR (101 MHz, CDCl$_3$) δ 171.3, 170.1, 137.5, 134.7, 134.2, 129.3, 126.3, 123.0, 69.1, 62.3, 54.4, 40.2, 28.1, 21.3, 20.6, 14.2; IR (Neat Film, NaCl) 2978, 1731, 1513, 1456, 1399, 1367, 1269, 1242, 1197, 1163, 1096, 1025, 972, 859, 803, 642 cm$^{-1}$; HRMS (MM) m/z calc'd for C$_{18}$H$_{23}$O$_4$ [M+H]$^+$: 303.1591. found 303.1591; SFC Conditions: 10% IPA, 2.5 mL/min, Chiralpak AD-H column, λ=254 nm, $t_R$ (min): major 6.47, minor=7.71.

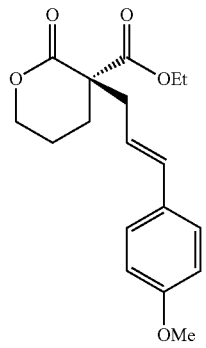

3ad

Ethyl (R,E)-3-(3-(4-methoxyphenyl)allyl)-2-oxotetrahydro-2H-pyran-3-carboxylate (3ad)

Product 3ad was prepared using general procedure 3 and purified by column chromatography (15% EtOAc in hexanes) to provide a colorless oil (50.5 mg, 79% yield); 88% ee, $[\alpha]_D^{25}$-15.9 (c 0.95, CHCl$_3$); $^1$H NMR (400 MHz, CDCl$_3$) δ 7.32-7.24 (m, 2H), 6.89-6.79 (m, 2H), 6.41 (d, J=15.8 Hz, 1H), 6.03 (ddd, J=15.7, 8.0, 7.0 Hz, 1H), 4.29 (t, J=5.9 Hz, 2H), 4.22 (q, J=7.2 Hz, 2H), 3.79 (s, 3H), 2.89 (ddd, J=13.8, 7.0, 1.4 Hz, 1H), 2.71 (ddd, J=13.7, 8.1, 1.2 Hz, 1H), 2.43-2.29 (m, 1H), 2.05-1.79 (m, 3H), 1.27 (t, J=7.1 Hz, 3H); $^{13}$C NMR (101 MHz, CDCl$_3$) δ 171.3, 170.2, 159.2, 134.2, 129.8, 127.5, 121.7, 114.0, 69.1, 62.2, 55.4, 54.5, 40.1, 28.1, 20.6, 14.2; IR (Neat Film, NaCl) 2978, 2837, 1732, 1608, 1577, 1512, 1457, 1400, 1349, 1367, 1249, 1198, 1108, 1032, 972, 840, 757, 667, 640; HRMS (MM) m/z calc'd for C$_{18}$H$_{23}$O$_5$ [M+H]$^+$: 319.1540, found 319.1525; SFC Conditions: 15% IPA, 2.5 mL/min, Chiralpak AD-H column, λ=254 nm, $t_R$ (min): major=5.37, minor=6.37.

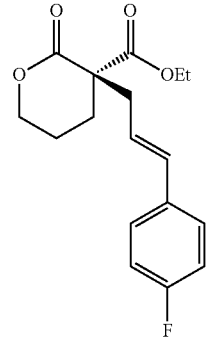

3ae

Ethyl (R,E)-3-(3-(4-fluorophenyl)allyl)-2-oxotetrahydro-2H-pyran-3-carboxylate (3ae)

Product 3ae was prepared using general procedure 3 and purified by column chromatography (15% EtOAc in hexanes) to provide a colorless oil (38.2 mg, 62% yield); 88% ee, $[\alpha]_D^{25}$-10.19 (c 0.86, CHCl$_3$); $^1$H NMR (400 MHz, CDCl$_3$) δ 7.34-7.27 (m, 2H), 7.05-6.90 (m, 2H), 6.53-6.34 (m, 1H), 6.20-6.02 (m, 1H), 4.29 (t, J=5.6 Hz, 2H), 4.22 (q, J=7.1 Hz, 2H), 2.87 (ddd, J=13.9, 7.1, 1.4 Hz, 1H), 2.72 (ddd, J=13.8, 7.9, 1.2 Hz, 1H), 2.47-2.31 (m, 1H), 2.07-1.78 (m, 3H), 1.26 (t, J=7.1 Hz, 3H); $^{13}$C NMR (101 MHz, CDCl$_3$) 171.2, 170.1, 162.4 (d, J=246.8 Hz), 133.5, 133.1 (d, J=3.3 Hz), 127.9 (d, J=8.0 Hz), 123.9 (d, J=2.2 Hz), 115.5 (d, J=21.7 Hz), 69.0, 62.3, 54.4, 40.1, 28.2, 20.6, 14.2; $^{19}$F NMR (282 MHz, CDCl$_3$) δ-114.56 (tt, J=8.6, 5.3 Hz); IR (Neat Film, NaCl) 2981, 2342, 1733, 1602, 1508, 1456, 1400, 1368, 1349, 1298, 1269, 1226, 1198, 1160, 1095, 1025, 972, 847, 767, 711, 668, 639 cm$^{-1}$; HRMS (MM) m/z calc'd for C$_{17}$H$_{20}$FO$_4$ [M+H]$^+$: 307.1340 found 307.1343; SFC Conditions: 10% IPA, 2.5 mL/min, Chiralpak AD-H column, λ=254 nm, $t_R$ (min): major=5.12, minor=5.95.

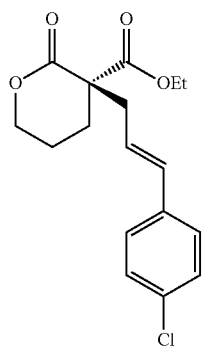

Ethyl (R,E)-3-(3-(4-chlorophenyl)allyl)-2-oxotetrahydro-2H-pyran-3-carboxylate (3af)

Product 3af was prepared using general procedure 3 and purified by column chromatography (15% EtOAc in hexanes) to provide a colorless oil (39.5 mg, 61% yield); 87% ee. $[\alpha]_D^{25}$-10.81 (c 0.83, CHCl$_3$); $^1$H NMR (400 MHz, CDCl$_3$) δ 7.26 (s, 4H), 6.42 (dt, J=15.7, 1.3 Hz, 1H), 6.18 (ddd, J=15.9, 7.9, 7.1 Hz, 1H), 4.29 (t, J=5.7 Hz, 2H), 4.22 (q, J=7.1 Hz, 2H), 2.87 (ddd, J=13.9, 7.1, 1.4 Hz, 1H), 2.74 (ddd, J=13.8, 7.9, 1.2 Hz, 1H), 2.46-2.32 (m, 1H), 2.15-1.80 (m, 3H), 1.26 (t, J=7.1 Hz, 3H); $^{13}$C NMR (101 MHz, CDCl$_3$) δ 171.1, 170.1, 135.4, 133.5, 133.2, 128.8, 127.6, 124.9, 69.0, 62.3, 54.4, 40.1, 28.2, 20.6, 14.2; IR (Neat Film, NaCl) 2979, 2358, 1729, 1490, 1455, 1404, 1243, 1197, 1164, 1092, 971, 820, 760, 679 cm$^{-1}$; HRMS (MM) m/z calc'd for C$_{17}$H$_{20}$ClO$_4$ [M+H]$^+$: 323.1045, found 323.1041; SFC Conditions: 30% IPA, 2.5 mL/min, Chiralpak AD-H column, λ=254 nm, t$_R$ (min): major=2.29, minor=2.57.

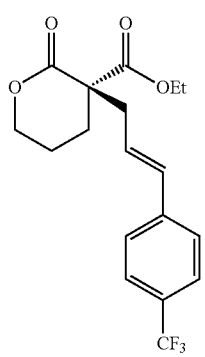

Ethyl (R,E)-2-oxo-3-(3-(4-(trifluoromethyl)phenyl)allyl)tetrahydro-2H-pyran-3-carboxylate (3ag)

Product 3ag was prepared using general procedure 3 and purified by column chromatography (15% EtOAc in hexanes) to provide a colorless oil (31.2 mg, 44% yield); 86% ee, $[\alpha]_D^{25}$-6.52 (c 0.98, CHCl$_3$); $^1$H NMR (400 MHz, CDCl$_3$) δ 7.60-7.47 (m, 2H), 7.47-7.38 (m, 2H), 6.50 (d, J=15.8 Hz, 1H), 6.32 (dt, J=15.8, 7.5 Hz, 1H), 4.30 (dd, J=6.3, 5.2 Hz, 2H), 4.23 (q, J=7.1 Hz, 2H), 2.90 (ddd, J=13.8, 7.1, 1.3 Hz, 1H), 2.77 (ddd, J=13.8, 7.7, 1.2 Hz, 1H), 2.47-2.34 (m, 1H), 2.05-1.81 (m, 3H), 1.26 (t, J=7.1 Hz, 3H); $^{13}$C NMR (101 MHz, CDCl$_3$) δ 171.1, 170.0, 140.4 (d, J=1.6 Hz), 133.4, 129.4 (q, J=32.4 Hz), 127.2, 126.5, 125.6 (q, J=3.7 Hz), 122.9, 69.0, 62.4, 54.4, 40.1, 28.3, 20.6, 14.2; $^{19}$F NMR (282 MHz, CDCl$_3$) δ -62.52 (s); IR (Neat Film, NaCl) 2982, 1733, 1684, 1616, 1540, 1414, 1326, 1244, 1198, 1163, 1120, 1068, 1016, 972, 862, 833, 652; HRMS (MM) m/z calc'd for C$_{18}$H$_{20}$F$_3$O$_4$ [M+H]$^+$: 357.1308, found 357.1307; SFC Conditions: 10% IPA, 2.5 mL/min, Chiralpak AD-H column, λ=254 nm, t$_R$ (min): major=4.02, minor=4.72.

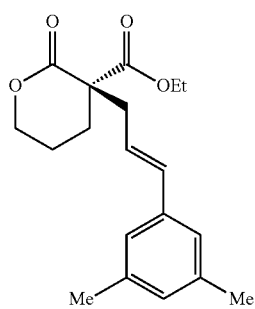

Ethyl (R,E)-3-(3-(3,5-dimethylphenyl)allyl)-2-oxotetrahydro-2H-pyran-3-carboxylate (3ah)

Product 3ah was prepared using general procedure 3 and purified by column chromatography (15% EtOAc in hexanes) to provide a colorless oil (41.0 mg, 65% yield); 88% ee, $[\alpha]_D^{25}$-13.58 (c 0.84, CHCl$_3$); $^1$H NMR (400 MHz, CDCl$_3$) δ 7.00-6.94 (m, 2H), 6.87 (dt, J=1.9, 1.0 Hz, 1H), 6.46-6.36 (m, 1H), 6.15 (ddd, J=15.7, 8.2, 6.8 Hz, 1H), 4.32-4.27 (m, 2H), 4.27-4.20 (m, 2H), 2.91 (ddd, J=13.8, 6.8, 1.4 Hz, 1H), 2.71 (ddd, J=13.7, 8.2, 1.2 Hz, 1H), 2.43-2.26 (m, 7H), 2.04-1.79 (m, 3H), 1.28 (t, J=7.1 Hz, 3H); $^{13}$C NMR (101 MHz, CDCl$_3$) δ 171.3, 170.2, 138.1, 136.8, 135.0, 129.4, 124.3, 123.6, 69.1, 62.3, 54.4, 40.2, 28.1, 21.3, 20.6, 14.2; IR (Neat Film, NaCl) 2978, 2917, 1731, 1602, 1456, 1398, 1367, 1350, 1242, 1198, 1163, 1096, 1026, 972, 853, 759, 693, 638 cm$^{-1}$; HRMS (MM) m/z calc'd for C$_{19}$H$_{25}$O$_4$ [M+H]$^+$: 317.1747, found 317.1749; SFC Conditions: 5% IPA, 3.0 mL/min, Chiralpak AD-H column, λ=254 nm, t$_R$ (min): minor=9.68, major=11.56.

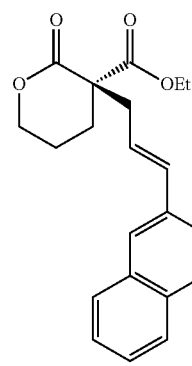

Ethyl (R,E)-3-(3-(naphthalen-2-yl)allyl)-2-oxotetrahydro-2H-pyran-3-carboxylate (3ai)

Product 3ai was prepared using general procedure 3 and purified by column chromatography (15% EtOAc in hexanes) to provide a colorless oil (42.1 mg, 62% yield); 88% ee, $[\alpha]_D^{25}$+27.34 (c 0.82, CHCl$_3$); $^1$H NMR (400 MHz, CDCl$_3$) δ 7.84-7.73 (m, 3H), 7.72-7.67 (m, 1H), 7.57 (dd, J=8.5, 1.8 Hz, 1H), 7.52-7.38 (m, 2H), 6.68-6.59 (m, 1H), 6.34 (ddd, J=15.8, 8.0, 7.0 Hz, 1H), 4.30 (t, J=5.8 Hz, 2H), 4.24 (q, J=7.1 Hz, 2H), 2.96 (ddd, J=13.7, 7.0, 1.4 Hz, 1H), 2.81 (ddd, J=13.7, 8.0, 1.2 Hz, 1H), 2.48-2.34 (m, 1H), 2.03-1.81 (m, 3H), 1.28 (t, J=7.1 Hz, 3H); $^{13}$C NMR (101 MHz, CDCl$_3$) 171.2, 170.1, 134.8, 134.3, 133.6, 133.0, 128.2, 128.0, 127.7, 126.3, 126.1, 125.9, 124.5, 123.6, 69.0, 62.3, 54.4, 40.2, 28.1, 20.6, 14.2; IR (Neat Film, NaCl) 2980, 1732, 1597, 1507, 1456, 1399, 1367, 1243, 1198, 1097, 1023, 971, 896, 861, 815, 751, 667, 639, 624; HRMS (MM) m/z calc'd for C$_{21}$H$_{23}$O$_4$ [M+H]$^+$: 339.1591, found 339.1595; SFC Conditions 30% IPA, 2.5 mL/min, Chiralpak AD-H column λ=254 nm, t$_R$ (min): major=3.36, minor=4.24.

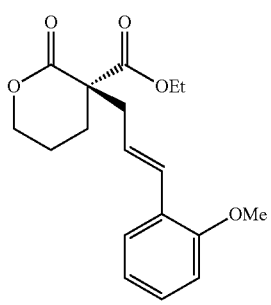

Ethyl (R,E)-3-(3-(2-methoxyphenyl)allyl)-2-oxotetrahydro-2H-pyran-3-carboxylate (3aj)

Product 3aj was prepared using general procedure 3 and purified by column chromatography (15% EtOAc in hexanes) to provide a colorless oil (32.4 mg, 51% yield); 90% ee, $[\alpha]_D^{25}$-11.96 (c 0.87, CHCl$_3$); $^1$H NMR (400 MHz, CDCl$_3$) δ 7.40 (dd, J=7.7, 1.7 Hz, 1H), 7.21 (ddd, J=8.2, 7.4, 1.7 Hz, 1H), 6.90 (td, J=7.6, 1.1 Hz, 1H), 6.88-6.75 (m, 2H), 6.16 (ddd, J=15.9, 8.2, 6.9 Hz, 1H), 4.29 (dd, J=6.2, 5.5 Hz, 2H), 4.23 (q, J=7.1 Hz, 2H), 3.83 (s, 3H), 2.92 (ddd, J=13.8, 6.8, 1.5 Hz, 1H), 2.77 (ddd, J=13.7, 8.2, 1.2 Hz, 1H), 2.44-2.29 (m, 1H), 2.03-1.81 (m, 3H), 1.28 (t, J=7.1 Hz, 3H); $^{13}$C NMR (101 MHz, CDCl$_3$) δ 171.3, 170.2, 156.5, 129.5, 128.7, 126.8, 126.0, 124.5, 120.7, 110.9, 69.2, 62.2, 55.5, 54.4, 40.6, 28.1, 20.7, 14.2; IR (Neat Film, NaCl) 2978, 2838, 1732, 1598, 1489, 1464, 1399, 1244, 1198, 1163, 1104, 1051, 1027, 976, 858, 755, 641; HRMS (MM) m/z calc'd for C$_{18}$H$_{23}$O$_5$ [M+H]$^+$: 319.1540, found 319.1542; SFC Conditions 10% IPA, 2.5 mL/min, Chiralcel OD-H column λ=254 nm, t$_R$ (min): minor=9.05, major=9.85.

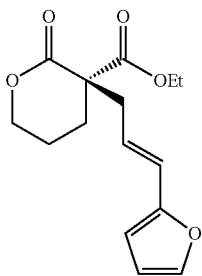

Ethyl (R,E)-3-(3-(furan-2-yl)allyl)-2-oxotetrahydro-2H-pyran-3-carboxylate (3ak)

Product 3ak was prepared using general procedure 3 and purified by column chromatography (15% EtOAc in hexanes) to provide a colorless oil (45.5 mg, 82% yield); 88% e, $[\alpha]_D^{25}$-11.85 (c 0.99, CHC$_{13}$); $^1$H NMR (400 MHz, CDCl$_3$) δ 7.32-7.27 (m, 1H), 6.37-6.23 (m, 2H), 6.17 (d, J=3.2 Hz, 1H), 6.14-6.01 (m, 1H), 4.29 (dd, J=6.3, 5.5 Hz, 2H), 4.22 (q, J=7.1 Hz, 2H), 2.86 (ddd, J=13.9, 7.2, 1.3 Hz, 1H), 2.70 (ddd, J=13.9, 8.0, 1.2 Hz, 1H), 2.40-2.29 (m, 1H), 2.05-1.78 (m, 3H), 1.26 (t, J=7.1 Hz, 3H); 3C NMR (101 MHz, CDCl$_3$) 171.2, 170.0, 152.4, 141.9, 123.2, 122.7, 111.3, 107.6, 69.1, 62.3, 54.4, 39.8, 28.1, 20.6, 14.1; IR (Neat Film, NaCl) 2980, 1732, 1456, 1399, 1244, 1200, 1166, 1097, 1017, 969, 926, 858, 749, 640; HRMS (MM) m/z calc'd for C$_{15}$H$_{19}$O$_5$ [M+H]$^+$: 343.1329, found 343.1327; SFC Conditions 10% IPA, 2.5 mL/min, Chiralpak AD-H column λ=254 nm, t$_R$ (min): major=3.97, minor=4.62.

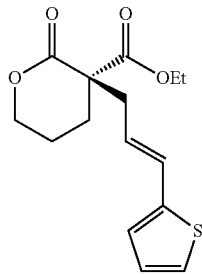

Ethyl (R,E)-2-oxo-3-(3-(thiophen-2-yl)allyl)tetrahydro-2H-pyran-3-carboxylate (3al)

Product 3al was prepared using general procedure 3 and purified by column chromatography (15% EtOAc in hexanes) to provide a colorless oil (39.9 mg, 68% yield); 88% ee, $[\alpha]_D^{25}$-15.7 (c 0.98, CHCl$_3$); $^1$H NMR (400 MHz, CDCl$_3$) δ 7.12 (dt, J=4.9, 1.0 Hz, 1H), 6.97-6.87 (m, 2H), 6.59 (dtt, J=15.7, 1.4, 0.6 Hz, 1H), 6.00 (ddd, J=15.4, 8.0, 7.2 Hz, 1H), 4.29 (t, J=5.9 Hz, 2H), 4.22 (q, J=7.1 Hz, 2H), 2.86 (ddd, J=13.9, 7.2, 1.4 Hz, 1H), 2.70 (ddd, J=13.8, 8.0, 1.2 Hz, 1H), 2.42-2.29 (m, 1H), 2.06-1.80 (m, 3H), 1.27 (t, J=7.1 Hz, 3H); $^{13}$C NMR (101 MHz, CDCl$_3$) δ 171.2, 170.0, 142.0, 127.9, 127.4, 125.5, 124.2, 123.7, 69.1, 62.3, 54.4, 40.0, 28.2, 20.6, 14.2; IR (Neat Film, NaCl) 3107, 2980, 1731, 1446, 1367, 1348, 1244, 1199, 1165, 1096, 1024, 965, 855, 750, 704, 643; HRMS (MM) m/z calc'd for C$_{15}$H$_{19}$O$_4$S

[M+H]⁺: 295.0999, found 295.0994; SFC Conditions 10% IPA, 2.5 mL/min, Chiralpak AD-H column λ=254 nm, t_R (min): major=6.33, minor=7.51.

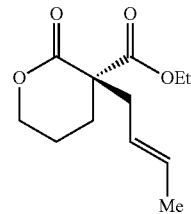

3am

Ethyl (R,E)-3-(but-2-en-1-yl)-2-oxotetrahydro-2H-pyran-3-carboxylate (3am)

Product 3am was prepared using general procedure 3 and purified by column chromatography (15% EtOAc in hexanes) to provide a colorless oil (25.6 mg, 57% yield); 78% ee, [α]_D²⁵-0.22 (c 1.13, CHCl₃); ¹H NMR (400 MHz, CDCl₃) δ 5.55 (dqt, J=15.0, 6.2, 1.1 Hz, 1H), 5.47-5.30 (m, 1H), 4.27 (t, J=5.7 Hz, 2H), 4.20 (q, J=7.1 Hz, 2H), 2.72-2.61 (m, 1H), 2.51 (ddt, J=13.8, 7.7, 1.1 Hz, 1H), 2.35-2.26 (m, 1H), 2.02-1.90 (m, 1H), 1.90-1.78 (m, 2H), 1.65 (dq, J=6.5, 1.2 Hz, 3H), 1.26 (t, J=7.1 Hz, 3H); ¹³C NMR (101 MHz, CDCl₃) δ 171.4, 170.2, 130.7, 124.9, 69.0, 62.1, 54.3, 39.7, 27.9, 20.6, 18.1, 14.2; IR (Neat Film, NaCl) 2965, 2938, 1730, 1447, 1400, 1272, 1223, 1198, 1163, 1107, 1077, 973, 856; HRMS (MM) m/z calc'd for C₁₂H₁₉O₄ [M+H]⁺: 227.1278, found 227.1275; SFC Conditions 25% IPA, 2.5 mL/min, Chiralpak IC column λ=210 nm, t_R (min): major=2.87, minor=3.69.

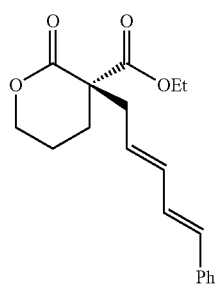

3an

Ethyl (R)-2-oxo-3-((2E,4E)-5-phenylpenta-2,4-dien-1-yl)tetrahydro-2H-pyran-3-carboxylate (3an)

Product 3an was prepared using general procedure 3 and purified by column chromatography (15% EtOAc in hexanes) to provide a colorless oil (57.3 mg, 91% yield); 88% ee, [α]_D²⁵-22.45 (c 0.96, CHCl₃); ¹H NMR (400 MHz, CDCl₃) δ 7.39-7.35 (m, 2H), 7.30 (ddd, J=7.7, 6.8, 1.2 Hz, 2H), 7.24-7.17 (m, 1H), 6.74 (ddd, J=15.7, 10.4, 0.8 Hz, 1H), 6.49 (d, J=15.7 Hz, 1H), 6.28 (ddq, J=15.4, 10.5, 1.1 Hz, 1H), 5.83-5.69 (m, 1H), 4.29 (t, J=5.8 Hz, 2H), 4.23 (q, J=7.1 Hz, 2H), 2.84 (ddd, J=13.9, 7.2, 1.3 Hz, 1H), 2.68 (ddd, J=13.8, 8.1, 1.1 Hz, 1H), 2.41-2.26 (m, 1H), 2.03-1.80 (m, 3H), 1.28 (t, J=7.1 Hz, 3H); ¹³C NMR (101 MHz, CDCl₃) δ 171.2, 170.0, 137.2, 135.3, 132.1, 128.7, 128.5, 128.3, 127.6, 126.4, 69.0, 62.3, 54.4, 39.9, 28.1, 20.6, 14.2;

IR (Neat Film, NaCl) 3058, 3024, 2980, 1732, 1490, 1478, 1448, 1400, 1367, 1347, 1241, 1198, 1097, 1025, 994, 910, 857, 750, 694, 667, 640; HRMS (MM) m/z calc'd for C₁₉H₂₃O₄ [M+H]⁺: 315.1585, found 315.1585; SFC Conditions 15% IPA, 2.5 mL/min, Chiralpak AD-H column λ=254 nm, t_R (min): major=5.30, minor=6.23.

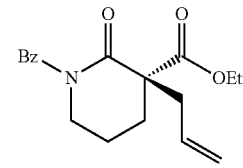

5aa

Ethyl (S)-3-allyl-1-benzoyl-2-oxopiperidine-3-carboxylate (5aa)

Product 5aa was prepared using general procedure 4 and purified by column chromatography (15% EtOAc in hexanes) to provide a colorless oil (45.9 mg, 73% yield); 90% ee, [α]_D²⁵+42.42 (c 0.968, CHCl₃); ¹H NMR (400 MHz, CDCl₃) δ ¹H NMR (400 MHz, CDCl₃) δ 7.84-7.70 (m, 2H), 7.54-7.44 (m, 1H), 7.44-7.34 (m, 2H), 5.80-5.62 (m, 1H), 5.17-5.03 (m, 2H), 4.30 (q, J=7.2 Hz, 2H), 3.84-3.71 (m, 2H), 2.72 (ddt, J=13.8, 6.8, 1.2 Hz, 1H), 2.56 (ddt, J=13.8, 7.9, 1.0 Hz, 1H), 2.43-2.25 (m, 1H), 2.04-1.83 (m, 3H), 1.36 (t, J=7.1 Hz, 3H); 3C NMR (101 MHz, CDCl₃) δ 175.1, 171.9, 171.8, 135.9, 133.0, 131.8, 128.2, 128.1, 119.7, 62.1, 56.4, 46.6, 40.0, 30.3, 20.3, 14.3; IR (Neat Film, NaCl) 3074, 2936, 2341, 1734, 1700, 1684, 1450, 1388, 1278, 1147, 1177, 1050, 1027, 919, 824, 726, 694, 668 cm⁻¹; HRMS (MM) m/z calc'd for C₁₈H₂₂NO₄ [M+H]⁺: 316.1543, found 316.1543; SFC Conditions: 20% IPA, 2.5 mL/min, Chiralpak IC column, λ=254 nm, t_R (min): major=3.77, minor=4.39.

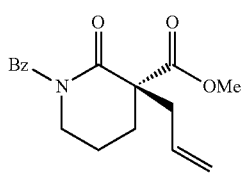

5ba

Methyl (S)-3-allyl-1-benzoyl-2-oxopiperidine-3-carboxylate (5ba)

Product 5ba was prepared using general procedure 4 and purified by column chromatography (20% EtOAc in hexanes) to provide a colorless oil (51.0 mg, 85% yield); 90% ee, [α]_D²⁵+48.58 (c 0.890, CHCl₃); ¹H NMR (400 MHz, CDCl₃) δ 7.77-7.59 (m, 2H), 7.55-7.44 (m, 1H), 7.40 (ddt, J=8.3, 6.6, 1.2 Hz, 2H), 5.84-5.63 (m, 1H), 5.20-5.02 (m, 2H), 3.83 (s, 3H), 3.77 (dd, J=6.7, 5.4 Hz, 2H), 2.73 (ddt, J=13.7, 6.8, 1.2 Hz, 1H), 2.57 (ddt, J=13.7, 7.7, 1.1 Hz, 1H), 2.41-2.29 (m, 1H), 2.07-1.85 (m, 3H); ¹³C NMR (101 MHz, CDCl₃) δ 175.1, 172.4, 171.8, 135.9, 133.0, 131.8, 128.2, 128.1, 119.8, 56.5, 52.9, 46.6, 39.9, 30.3, 20.2; IR (Neat Film, NaCl) 3075, 2953, 1738, 1702, 1683, 1640, 1583, 1478, 1449, 1436, 1349, 1277, 1252, 1177, 1147, 1078, 1052, 1027, 1001, 844, 819, 796, 726, 695, 651; HRMS (MM) m/z calc'd for $C_{17}H_{20}NO_4$ [M+H]$^+$: 302.1387, found 302.1377; SFC Conditions 10% IPA, 2.5 mL/min, Chiralpak AD-H column λ=254 nm, $t_R$ (min): minor=3.96, major=4.53.

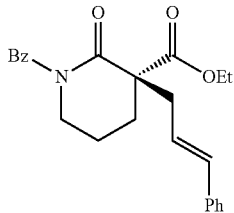

5ab

Ethyl (S)-1-benzoyl-3-cinnamyl-2-oxopiperidine-3-carboxylate (5ab)

Product 5ab was prepared using general procedure 4 at 30° C. and purified by column chromatography (20% to 40% Et$_2$O in hexanes) to provide a colorless oil (58.2 mg, 74% yield); 90% ee, $[\alpha]_D^{25}$+71.0 (c 0.88, CHCl$_3$); $^1$H NMR (400 MHz, CDCl$_3$) δ 7.81-7.73 (m, 2H), 7.55-7.45 (m, 1H), 7.45-7.37 (m, 2H), 7.36-7.27 (m, 4H), 7.25-7.20 (m, 1H), 6.46 (dt, J=15.7, 1.3 Hz, 1H), 6.14 (ddd, J=15.8, 8.0, 6.9 Hz, 1H), 4.32 (q, J=7.1 Hz, 2H), 3.86-3.73 (m, 2H), 2.91 (ddd, J=13.8, 7.0, 1.4 Hz, 1H), 2.72 (ddd, J=13.8, 8.0, 1.2 Hz, 1H), 2.49-2.35 (m, 1H), 2.10-1.91 (m, 3H), 1.37 (t, J=7.1 Hz, 3H); $^{13}$C NMR (101 MHz, CDCl$_3$) δ 175.0, 172.0, 171.9, 137.0, 135.9, 134.6, 131.9, 128.6, 128.2, 128.2, 127.6, 126.4, 124.5, 62.2, 56.9, 46.6, 39.3, 30.5, 20.3, 14.3; IR (Neat Film, NaCl) 2979, 1728, 1684, 1600, 1578, 1449, 1390, 1277, 1194, 1172, 1150, 1026, 970, 923, 934, 857, 822, 795, 745, 725, 694, 661 cm$^{-1}$; HRMS (MM) m/z calc'd for $C_{24}H_{26}NO_4$ [M+H]$^+$: 392.1856, found 392.1849; SFC Conditions: 30% IPA, 2.5 mL/min, Chiralpak AD-H column, λ=254 nm, $t_R$ (min): minor=2.56, major=2.95.

Experimental Procedures and Characterization Data for Product Transformations

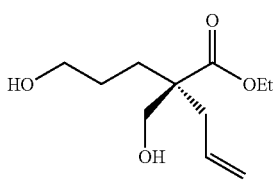

6

Ethyl (S)-2-(hydroxymethyl)-2-(3-hydroxypropyl)pent-4-enoate (6)

To a solution of allylated product 3aa (42.5 mg, 0.2 mmol, 1 equiv) in 4:1 methanol:THF (1.4 mL), CeCl$_3$.7H$_2$O was added (149.0 mg, 0.4 mmol, 2 equiv). After cooling the reaction mixture at 0° C. for 10 minutes, NaBH$_4$ (37.5 mg, 1.0 mmol, 5 equiv) was added in three portions over the course of 20 minutes. Additional methanol (1.5 mL) was added to rinse the side of the flask and the reaction mixture was stirred for another 10 minutes. The reaction was quenched with glacial acetic acid. The crude mixture was then concentrated under reduced pressure. The resultant residue was extracted with EtOAc, washed with NaHCO$_3$ and brine, dried over anhydrous MgSO$_4$, filtered, and purified by column chromatography (70% EtOAc in hexanes) to afford diol 6 as a colorless oil (54.1 mg, 88% yield). $[\alpha]_D^2$+1.222 (c 0.92, CHCl$_3$); $^1$H NMR (400 MHz, CDCl$_3$) δ 5.71 (ddt, J=17.4, 10.1, 7.4 Hz, 1H), 5.14-4.99 (m, 2H), 4.15 (q, J=7.1 Hz, 2H), 3.72-3.62 (m, 2H), 3.59 (td, J=6.2, 1.6 Hz, 2H), 2.65 (br s, 2H), 2.38 (ddt, J=14.0, 7.3, 1.2 Hz, 1H), 2.30 (ddt, J=13.9, 7.5, 1.1 Hz, 1H), 1.75-1.58 (m, 2H), 1.58-1.42 (m, 2H), 1.25 (t, J=7.1 Hz, 3H); $^{13}$C NMR (101 MHz, CDCl$_3$) δ 176.0, 133.4, 118.6, 64.5, 62.9, 60.8, 50.8, 38.0, 29.3, 27.1, 14.4; IR (Neat Film, NaCl) 2281, 3078, 2940, 1725, 1641, 1465, 1447, 1372, 1329, 1300, 1219, 1191, 1138, 1112, 1053, 920, 862, 824, 782, 748, 679, 634; HRMS (MM) m/z calc'd for $C_{11}H_{21}O_4$ [M+H]$^+$: 217.1434, found 217.1427.

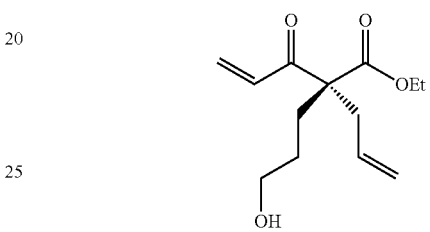

7

Ethyl (S)-2-allyl-2-(3-hydroxypropyl)-3-oxopent-4-enoate (7)

A 0.5 M solution of vinylmagnesium bromide in THF (0.3 mmol, 1.5 equiv) was added dropwise to a solution of allylated product 3aa (42.5 mg, 0.2 mmol, 1 equiv) in THF (0.7 mL) at −78° C. over 15 minutes. After 9 hours at −78° C., the reaction was quenched with NH$_4$Cl. The mixture was diluted with EtOAc, washed with brine, and dried over anhydrous Na$_2$SO$_4$. Flash column chromatography (50% EtOAc in hexanes) of the crude residue afforded compound 7 as a colorless oil (80.0 mg, 67% yield); 86% ee, $[\alpha]_D^{25}$-9.914 (c 0.798, CHCl$_3$); $^1$H NMR (400 MHz, CDCl$_3$) δ 6.53 (dd, J=16.9, 10.2 Hz, 1H), 6.39 (dd, J=17.0, 1.8 Hz, 1H), 5.70 (dd, J=10.1, 1.8 Hz, 1H), 5.57 (ddt, J=16.8, 10.1, 7.4 Hz, 1H), 5.16-5.04 (m, 2H), 4.19 (qd, J=7.1, 0.7 Hz, 2H), 3.62 (td, J=6.4, 1.1 Hz, 2H), 2.79-2.55 (m, 2H), 2.04-1.82 (m, 2H), 1.51-1.30 (m, 3H), 1.23 (t, J=7.1 Hz, 3H); $^{13}$C NMR (101 MHz, CDCl$_3$) δ 195.5, 172.1, 132.2, 131.8, 129.5, 119.3, 62.9, 61.7, 61.6, 35.9, 27.5, 27.0, 14.2; IR (Neat Film, NaCl) 340, 3079, 2924, 1732, 1698, 1642, 1612, 1447, 1402, 1368, 1299, 1262, 1200, 1137, 1096, 1057, 1029, 983, 923, 856, 808, 739, 670, 686, 654; HRMS (MM) m/z calc'd for $C_{13}H_{21}O_4$ [M+H]$^+$: 241.1440, found 241.1443; SFC Conditions: 30% IPA, 2.5 mL/min, Chiralpak IC column, λ=210 nm, $t_R$ (min): major=7.14, minor=7.64.

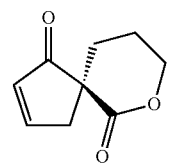

8

(S)-7-oxaspiro[4.5]dec-2-ene-1,6-dione (8)

Compound 7 (68.9 mg, 0.29 mmol, 1 equiv) in degassed toluene (3.0 mL) was added to a stirred solution of Grubbs' 11 catalyst (12.2 mg, 5 mol %) in toluene (15 mL) at 23° C. After stirring at 40° C. for 4 hours under argon atmosphere, the dark brown solution was filtered through silica plug, flushed with acetone, and concentrated under vacuum. The crude residue was then redissolved in acetonitrile, 1,8-Diazabicyclo[5.4.0]undec-7-ene (DBU) was added (52 uL, 0.35 mmol, 1.2 equiv), and the reaction mixture was stirred at room temperature. Upon complete consumption of starting material by TLC, the reaction was quenched with NH$_4$Cl, extracted with EtOAc, washed with brine, dried over Na$_2$SO$_4$ filtered, and concentrated under vacuum The crude residue was purified by column chromatography (30% acetone in hexanes) to provide spirocycle 8 as a colorless oil (25.6 mg, 53% yield). $[\alpha]_D^{25}$-62.168 (c 0.75, CHCl$_3$); $^1$H NMR (400 MHz, CDCl$_3$) δ 7.77 (dt, J=5.6, 2.7 Hz, 1H), 6.14 (dt, J=5.7, 2.2 Hz, 1H), 4.66-4.50 (m, 1H), 4.47-4.40 (m, 1H), 3.39 (dt, J=18.9, 2.5 Hz, 1H), 2.58 (dt, J=18.9, 2.4 Hz, 1H), 2.41-2.25 (m, 1H), 2.25-2.13 (m, 1H), 1.92-1.75 (m, 2H); $^{13}$C NMR (101 MHz, CDCl$_3$) δ 206.2, 170.1, 163.8, 131.2, 71.0, 53.9, 44.5, 30.7, 20.4; IR (Neat Film, NaCl) 3082, 2932, 2871, 1728, 1699, 1592, 1422, 1403, 1343, 1272, 1217, 1160, 1108, 1080, 963, 816, 763; HRMS (MM) m/z calc'd for C$_9$H$_{10}$O$_3$ [M+H]$^+$: 167.0703, found 167.0696.

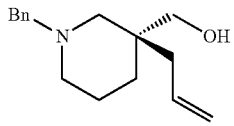

9

(S)-(3-allyl-1-benzylpiperidin-3-yl)methanol (9)

To a flame-dried microwave vial under argon was added lactam 5aa (63 mg, 0.2 mmol) and dry diethyl ether (2.0 mL). Lithium aluminum hydride (91 mg, 2.4 mmol) was added slowly. The reaction was allowed to stir at room temperature for 10 minutes, after which it was sealed and heated to 65° C. for 36 h. The reaction was quenched with water and 15% sodium hydroxide solution and extracted with ethyl acetate (5 mL×4). The combined extracts were dried with Na$_2$SO$_4$, filtered, and concentrated under vacuum. The crude residue was purified by column chromatography (50% EtOAc in hexanes) to afford alcohol 9 as a colorless oil (39.3 mg, 80% yield). $[\alpha]_D^{25}$+29.393 (c 0.965, CHCl$_3$); $^1$H NMR (400 MHz, CDCl$_3$) δ 7.36-7.22 (m, 5H), 5.74 (ddt, J=16.7, 10.4, 7.6 Hz, 1H), 5.06-4.95 (m, 2H), 3.63 (qd, J=10.6, 1.6 Hz, 2H), 3.52-3.39 (m, 2H), 2.78-2.66 (m, 2H), 2.10-2.00 (m, 3H), 1.91 (d, J=7.5 Hz, 2H), 1.69-1.54 (m, 2H), 1.36-1.19 (m, 2H); $^{13}$C NMR (101 MHz, CDCl$_3$) δ 138.0, 133.9, 129.1, 128.5, 127.3, 117.8, 72.4, 63.5, 62.8, 54.0, 37.2, 33.2, 29.8, 23.0; IR (Neat Film, NaCl) 3392, 3065, 3028, 3003, 2932, 2858, 2797, 2759, 1949, 1822, 1730, 1638, 1586, 1603, 1586, 1553, 1494, 1466, 1453, 1415, 1392, 1370, 1352, 1311, 1300, 1259, 1248, 1208, 1180, 1162, 1127, 1116, 1072, 1045, 1028, 1045, 1001, 913, 875, 834, 810, 739, 699, 635, 619; HRMS (MM) m/z calc'd for C$_{16}$H$_{24}$NO [M+H]$^+$: 246.1852, found 246.1847.

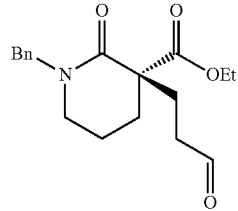

10

Ethyl (S)-1-benzoyl-2-oxo-3-(3-oxopropyl)piperidine-3-carboxylate (10)

To a flame dried vial was added CuCl$_2$.H$_2$O (4.1 mg, 0.024 mmol), PdCl$_2$(PhCN)$_2$ (9.2 mg, 0.024 mmol), AgNO$_2$ (1.9 mg, 0.012 mmol), t-BuOH (3.75 mL) and nitromethane (0.25 mL). The solution was sparged with 02 for 15 minutes, and then neat lactam 5aa (63.1 mg, 0.2 mmol) was added. The solution was then sparged for another 3 minutes and allowed to stir for 14 hours under an oxygen atmosphere. Upon reaction completion by TLC, water (4 mL) was added and the aqueous layer was extracted with DCM (4 mL×3). The combined organic layers were dried with Na$_2$SO$_4$, filtered, and concentrated under reduced pressure. The product was purified by column chromatography (50% EtOAc in hexanes) to yield 75% of product 10. $[\alpha]^{25}$+3.159 (c 0.685, CHCl$_3$); $^1$H NMR (400 MHz, CDCl$_3$) 9.69 (s, 1H), 7.78-7.69 (m, 2H), 7.52-7.44 (m, 1H), 7.44-7.35 (m, 2H), 4.38-4.24 (m, 2H), 3.89-3.70 (m, 2H), 2.73-2.59 (m, 1H), 2.55-2.38 (m, 2H), 2.23-2.13 (m, 2H), 2.06-1.91 (m, 2H), 1.82 (ddd, J=13.6, 9.9, 5.4 Hz, 1H), 1.37 (t, J=7.1 Hz, 3H); $^{13}$C NMR (101 MHz, CDCl$_3$) δ 200.9, 175.0, 172.1, 171.9, 135.8, 132.0, 128.2, 128.2, 62.4, 55.8, 46.6, 39.9, 31.5, 27.8, 20.2, 14.3; IR (Neat Film, NaCl) 2924, 2853, 2727, 1723, 1704, 1681, 1601, 1449, 1391, 1348, 1275, 1195, 1174, 1150, 1062, 1023, 959, 916, 856, 824, 796, 726, 695, 659; HRMS (MM) m/z calc'd for C$_{18}$H$_{22}$NO$_5$ [M+H]$^+$: 332.1492, found 332.1483.

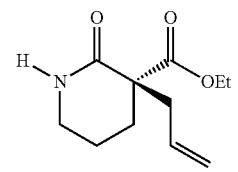

11

Ethyl (S)-3-allyl-2-oxopiperidine-3-carboxylate (11)

To a flame dried vial under argon was added NaOEt (17.4 mg, 0.26 mmol) and ethanol (1.3 mL). Lactam 5aa (63.1 mg, 0.20 mmol) was added and the resulting mixture was stirred for 48 h at 65° C. The reaction was quenched with citric acid (154 mg, 0.80 mmol) and the EtOH was removed in vacuo. The resulting oil was then diluted with water (2 mL) and extracted with chloroform. The combined organic layers were dried with Na$_2$SO$_4$ and the solvent was removed in vacuo. The product was purified by column chromatography (80% EtOAc in hexanes) to afford amide 11 as a colorless oil (35.6 mg, 84% yield). $[\alpha]_D^{25}$+36.162 (c 0.89, CHCl$_3$); $^1$H NMR (400 MHz, CDCl$_3$) δ 6.40 (s, 1H), 5.76 (dddd, J=16.8, 10.2, 8.1, 6.5 Hz, 1H), 5.20-5.05 (m, 2H), 4.29-4.10 (m, 2H), 3.40-3.18 (m, 2H), 2.78 (ddt, J=13.8, 6.5, 1.3 Hz, 1H), 2.66-2.50 (m, 1H), 2.14-2.04 (m, 1H), 1.93-1.68 (m, 3H), 1.26 (t, J=7.1 Hz, 3H); 3C NMR (101 MHz, CDCl$_3$) δ 172.7, 170.8, 133.7, 119.2, 61.6, 53.5, 42.5, 40.0, 29.4, 19.6, 14.3; IR (Neat Film, NaCl) 3213, 3077, 2978, 2941, 2873, 1732, 1668, 1490, 1469, 1417, 1392, 1356, 1326, 1314, 1297, 1282, 1241, 1193, 1153, 1116, 1094, 1026, 1005, 921, 856, 812, 763, 719, 663; HRMS (MM) m/z calc'd for C$_{11}$H$_{11}$NO$_3$ [M+H]$^+$: 212.1281, found 212.1280.

TABLE 8

Determination of Enantiomeric Excess

| entry | compound | SFC analytic conditions | ee (%) |
|---|---|---|---|
| 1 | 3aa | Chiralpak IC, λ = 210 nm, 25% IPA/CO$_2$, 2.5 mL/min, t$_R$ (min) major 2.66, minor 3.29 | 86 |
| 2 | 3ba | Chiralpak IC, λ = 210 nm, 20% IPA/CO$_2$, 2.5 mL/min, t$_R$ (min) major 3.35, minor 3.99 | 86 |
| 3 | 3ca | Chiracel OB-H, λ = 210 nm, 5% IPA/CO$_2$, 2.5 mL/min, t$_R$ (min) minor 2.22, major 2.64 | 64 |
| 4 | 3ab | Chiralpak AD-H, λ = 254 nm, 10% IPA/CO$_2$, 2.5 mL/min, t$_R$ (min) major 5.49, minor 6.31 | 90 |
| 5 | 3ac | Chiralpak AD-H, λ = 254 nm, 10% IPA/CO$_2$, 2.5 mL/min, t$_R$ (min) major 6.47, minor 7.71 | 90 |
| 6 | 3ad | Chiralpak AD-H, λ = 254 nm, 15% IPA/CO$_2$, 2.5 mL/min, t$_R$ (min) major 5.37, minor 6.37 | 88 |
| 7 | 3ae | Chiralpak AD-H, λ = 254 nm, 10% IPA/CO$_2$, 2.5 mL/min, t$_R$ (min) major 5.12, minor 5.95 | 88 |
| 8 | 3af | Chiralpak AD-H, λ = 254 nm, 30% IPA/CO$_2$, 2.5 mL/min, t$_R$ (min) major 2.29, minor 2.57 | 87 |

TABLE 8-continued

Determination of Enantiomeric Excess

| entry | compound | SFC analytic conditions | ee (%) |
|---|---|---|---|
| 9 | 3ag | Chiralpak AD-H, λ = 254 nm, 10% IPA/CO$_2$, 2.5 mL/min, t$_R$ (min) major 4.02, minor 4.72 | 86 |
| 10 | 3ah | Chiralpak AD-H, λ = 254 nm, 5% IPA/CO$_2$, 3 mL/min, t$_R$ (min) minor 9.68, major 11.56 | 88 |
| 11 | 3ai | Chiralpak AD-H, λ = 254 nm, 30% IPA/CO$_2$, 2.5 mL/min, t$_R$ (min) major 3.36, minor 4.24 | 88 |
| 12 | 3aj | Chiralcel OD-H, λ = 254 nm, 10% IPA/CO$_2$, 2.5 mL/min, t$_R$ (min) minor 9.05, major 9.85 | 90 |
| 13 | 3ak | Chiralpak AD-H, λ = 254 nm, 10% IPA/CO$_2$, 2.5 mL/min, t$_R$ (min) major 3.97, minor 4.62 | 88 |
| 14 | 3al | Chiralpak AD-H, λ = 254 nm, 10% IPA/CO$_2$, 2.5 mL/min, t$_R$ (min) major 6.33, minor 7.51 | 88 |
| 15 | 3am | Chiralpak IC, λ = 210 nm, 25% IPA/CO$_2$, 2.5 mL/min, t$_R$ (min) major 2.87, minor 3.69 | 78 |
| 16 | 3an | Chiralpak AD-H, λ = 254 nm, 15% IPA/CO$_2$, 2.5 mL/min, t$_R$ (min) major 5.30, minor 6.23 | 88 |
| 17 | 5aa | Chiralpak IC, λ = 254 nm, 20% IPA/CO$_2$, 2.5 mL/min, t$_R$ (min) major 3.77, minor 4.39 | 90 |

TABLE 8-continued

Determination of Enantiomeric Excess

| entry | compound | SFC analytic conditions | ee (%) |
|---|---|---|---|
| 18 | 5ba | Chiralpak AD-H, $\lambda$ = 254 nm, 10% IPA/CO$_2$, 2.5 mL/min, $t_R$ (min) minor 3.96 major 4.53 | 90 |
| 19 | 5ab | Chiralpak AD-H, $\lambda$ = 254 nm, 30% IPA/CO$_2$, 2.5 mL/min, $t_R$ (min) minor 2.56, major 2.95 | 90 |
| 20 | 7 | Chiralpak IC, $\lambda$ = 210 nm, 10% IPA/CO$_2$, 2.5 mL/min, $t_R$ (min) major 7.14, minor 7.64 | 86 |

X-Ray Crystal Structure Data for Allylated Product 3af

The alpha-quaternary lactone product 3af (87% ee) was crystallized from chloroform at −30° C. to provide crystals suitable for X-ray analysis (data and crystal structure not shown).

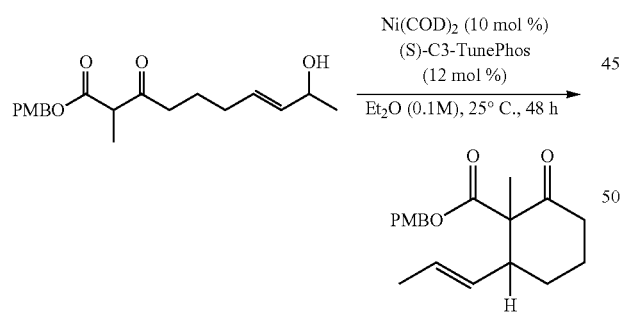

In a nitrogen-filled glovebox, to an oven-dried 4 mL vial equipped with a stir bar was added (S)—C$_3$-TunePhos (14.3 mg, 0.024 mmol, 12 mol %), Ni(COD)$_2$ (5.5 mg, 0.02 mmol, 10 mol %) and Et$_2$O (1.0 mL). The vial was capped with a PTFE-lined cap and stirred at room temperature for 30 min. A solution of the substrate (66.9 mg, 0.20 mmol) in Et$_2$O (0.5 mL) was then added to the catalyst mixture. The substrate vial was rinsed with additional Et$_2$O (0.5 mL) and added to the catalyst mixture. The reaction vial was sealed with a PTFE-lined cap, removed from the glovebox, and stirred at 25° C. for 48 h. The crude reaction mixture was filtered through a silica plug, rinsed with Et$_2$O, and concentrated under vacuum. The crude residue was subjected to a filtration over silica gel (20% EtOAc in hexanes) to remove unreacted starting material. After evaporation of solvents, the product was isolated as a mixture of diastereoisomeres (24.0 mg, 0.07 mmol, 37% yield, 83:17 dr). Enantiomeric excess=70% ee (Chiralpak IC, 15% IPA in C$_{O2}$).

Based on literature reference for the corresponding Et-ester (Kates. S. A.; Dombroski, M. A.; Snider, B. B. *J. Org. Chem.* 1990, 55, 2427-2436.), preliminary assignment for major diastereoisomer is shown below:

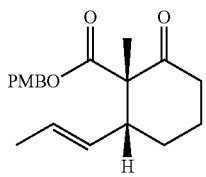

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

We claim:

1. A method of preparing a compound of Formula (XI):

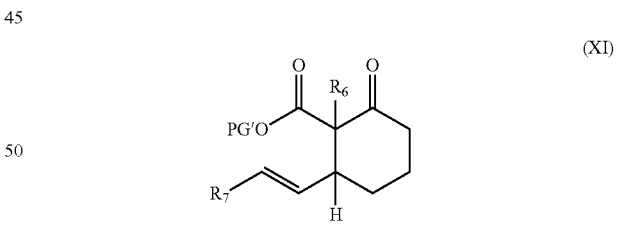

comprising treating a compound of Formula (XII)

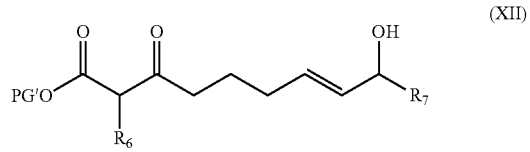

in an organic solvent
in the presence of a complex formed by contacting a Ni(0) source with a ligand, wherein
PG' is an oxygen protecting group;
$R_6$ is $C_{1-5}$ alkyl;
$R_7$ is $C_{1-5}$ alkyl;
the organic solvent is toluene, diethyl ether, methyl t-butyl ether, tetrahydrofuran, or dioxane, or a mixture thereof; and
the compound of Formula (XI) is enantioenriched.

2. The method of claim 1, wherein:
the Ni(0) source is Ni(COD)$_2$;
the ligand is (S)-C3-TunePhos; and
the organic solvent is diethyl ether.

3. The method of claim 1, wherein:
$R_6$ is methyl; and
$R_7$ is methyl.

4. The method of claim 2, wherein:
$R_6$ is methyl; and
$R_7$ is methyl.

5. A method of synthesizing a pharmaceutical agent, comprising preparing a compound of Formula (XI):

(XI)

the preparing comprising treating a compound of Formula (XII)

(XII)

in an organic solvent
in the presence of a complex formed by contacting a Ni(0) source with a ligand,
wherein
PG' is an oxygen protecting group;
$R_6$ is $C_{1-5}$ alkyl;
$R_7$ is $C_{1-5}$ alkyl; and
the organic solvent is toluene, diethyl ether, methyl t-butyl ether, tetrahydrofuran, or dioxane, or a mixture thereof.

6. The method of claim 5, wherein:
the Ni(0) source is Ni(COD)$_2$;
the ligand is (S)-C3-TunePhos; and
the organic solvent is diethyl ether.

7. The method of claim 5, wherein:
$R_6$ is methyl; and
$R_7$ is methyl.

8. The method of claim 6, wherein:
$R_6$ is methyl; and
$R_7$ is methyl.

* * * * *